US012759995B2

(12) United States Patent
Aube et al.

(10) Patent No.: US 12,759,995 B2
(45) Date of Patent: Oct. 13, 2026

(54) INHIBITORS OF RNA-BINDING PROTEINS, COMPOSITIONS THEREOF, AND THERAPEUTIC USES THEROF

(71) Applicants: The University of North Carolina at Chapel Hill, Chapel Hill, NC (US); University of Kansas, Lawrence, KS (US)

(72) Inventors: Jeff Aube, Chapel Hill, NC (US); Sudeshna Roy, Lawrence, KS (US); Liang Xu, Lawrence, KS (US); Xiaoqing Wu, Lawrence, KS (US); Lan Lan, Lawrence, KS (US)

(73) Assignees: The University of North Carolina, Chapel Hill, NC (US); University of Kansas, Lawrence, KS (US)

(*) Notice: Subject to any disclaimer, the term of this patent is extended or adjusted under 35 U.S.C. 154(b) by 1067 days.

(21) Appl. No.: 17/607,003

(22) PCT Filed: May 1, 2020

(86) PCT No.: PCT/US2020/031058
§ 371 (c)(1),
(2) Date: Oct. 27, 2021

(87) PCT Pub. No.: WO2020/242719
PCT Pub. Date: Dec. 3, 2020

(65) Prior Publication Data

US 2022/0213052 A1 Jul. 7, 2022

Related U.S. Application Data

(60) Provisional application No. 62/841,600, filed on May 1, 2019.

(51) Int. Cl.
*C07D 333/60* (2006.01)
*A61P 35/00* (2006.01)
(Continued)

(52) U.S. Cl.
CPC ............ *C07D 333/60* (2013.01); *A61P 35/00* (2018.01); *C07D 209/42* (2013.01); *C07D 409/12* (2013.01)

(58) Field of Classification Search
CPC .. C07D 333/60; C07D 209/42; C07D 409/12; A61P 35/00
See application file for complete search history.

(56) References Cited

U.S. PATENT DOCUMENTS 5,843,937 A 12/1998 Wang et al.
6,153,642 A 11/2000 Cozzi et al.
(Continued)

FOREIGN PATENT DOCUMENTS

CN 10168940 A 2/2010
CN 101648940 A 2/2010
(Continued)

OTHER PUBLICATIONS

National Center for Biotechnology Information. "PubChem Compound Summary for CID 46424910, Ethyl 5-(pyridine-2-carbonylamino)-1-benzothiophene-2-carboxylate" PubChem, https://pubchem.ncbi.nlm.nih.gov/compound/46424910. Accessed Oct. 7, 2024. (Year: 2024).*
(Continued)

*Primary Examiner* — Clinton A Brooks
*Assistant Examiner* — Kendall Nicole Heitmeier
(74) *Attorney, Agent, or Firm* — Foley & Lardner LLP

(57) ABSTRACT

The present technology is directed to compounds that inhibit of the interaction of RNA-binding proteins with RNA, intermediates thereof, compositions thereof, and methods of treatment utilizing such compounds, where the compounds are of Formula I, where $Z^1$ is aryl, heteroaryl, cycloalkyl; L' is absent, $—CH_2—$, $—CH_2—CH_2—$, or —CH≡CH—; $X^1$ is
(Continued)

O, NH, or S; and $X^2$ is OH, $NH_2$, NH—OH, NH—$NH_2$, or O—($C_1$-$C_6$ alkyl).

(I)

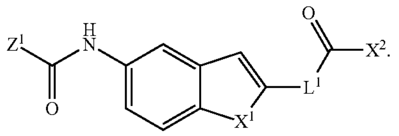

19 Claims, 19 Drawing Sheets

(51) Int. Cl.

| | |
|---|---|
| ***C07D 209/18*** | (2006.01) |
| ***C07D 209/42*** | (2006.01) |
| ***C07D 333/70*** | (2006.01) |
| ***C07D 401/12*** | (2006.01) |
| ***C07D 409/12*** | (2006.01) |

(56) References Cited

U.S. PATENT DOCUMENTS

| | | | | |
|---|---|---|---|---|
| 7,432,304 | B2 | 10/2008 | Wang et al. | |
| 2004/0204339 | A1 | 10/2004 | Dimartino | |
| 2005/0137234 | A1* | 6/2005 | Bressi | C07D 235/18 514/370 |
| 2006/0084647 | A1 | 4/2006 | Wang et al. | |
| 2010/0145036 | A1 | 6/2010 | Sufi et al. | |
| 2011/0028507 | A1 | 2/2011 | Kim et al. | |
| 2011/0207767 | A1* | 8/2011 | Beusker | C07D 403/14 548/200 |
| 2015/0231142 | A1 | 8/2015 | Van Goor et al. | |
| 2016/0271105 | A1* | 9/2016 | Hadida-Ruah | A61K 31/407 |
| 2018/0117166 | A1 | 5/2018 | Getts et al. | |
| 2022/0213052 | A1 | 7/2022 | Aube et al. | |

FOREIGN PATENT DOCUMENTS

| | | | |
|---|---|---|---|
| WO | WO-2010/062171 | A2 | 6/2010 |
| WO | WO-2020/242719 | A2 | 12/2020 |

OTHER PUBLICATIONS

Registry (STN) [online], Jun. 17, 2010 [Date of Search Jan. 27, 2025], CAS Registry Nos. 1227962-52-8 and 1227962-53-9. (Year: 2010).*

American Chemical Society. Chemical Abstract Service. RN 2215026-67-6, SR Chemical Catalog Supplier; Aurora Fine Chemicals. Entered into STN Apr. 18, 2018 (Year: 2018).*

Manzoni, L. et al. J. Med. Chem. 2018, 61, 1483-1498 (Year: 2018).*

Extended European Search Report issued for EP Appl. Ser. No. 20813936.0 dated Aug. 18, 2022 (12 pages).

International Search Report and Written Opinion issued for Appl. Ser. No. PCT/US2021/023410 dated Jun. 8, 2021 (6 pages).

Pubmed Compound Record for CID 45138015, 'Ethyl (E)-3-[5-((4-methylphenyl)sulfonylamino]-1-benzothiophen-2-yl]prop-2-enoate', U.S. National Library of Medicine, Apr. 26, 2010, pp. 1-6 (https://pubchem.ncbi.nlm.nih.gov/compound/45138015).

Pubmed Compound Record for CID 45138018, '(e)-3-(5-((4-(t-Butyl)phenyl) sulfonamido)benzo[b]thiophen-2-yl)-N-hydroxyacrylamide', U.S. National Library of Medicine, Apr. 26, 2010, pp. 1-9 (https://pubchem.ncbi.nlm.nih.gov/compound/45138018).

Allan et al. "N-Benzyl-1-heteroaryl-3-(trlfluoromethyl)-1 H-pyrazole-5-carboxamides as inhibitors of co-activator associated arginine methyltransfarase 1 (CARM1 )", Bioorganic and Medicinal Chemistry Letters. 2009. vol. 19, pp. 1218-1223.

International Search Report and Written Opinion mailed in PCT/US2020/031058 on Jan. 14, 2021 (17 pgs).

Invitation to Pay Additional Fees and, Where Applicable, Protest Fee mailed in PCT/US2020/031058 on Nov. 3, 2020 (2 pgs).

PubChem-CID-137990205, Create Date: Apr. 26, 2019 (Apr. 26, 2019), p. 2, Fig. (8 pgs).

PubChem-CID-46424910, Create Date: Jul. 23, 2010 (Jul. 23, 2010) (7 pgs).

Baraldi et al., "benzoyl and cinnamoyl nitrogen mustard derivatives of benzoheterocyclic analogues of the tallimustine: synthesis and antitumour activity", Bioorganic & Medicinal Chemistry , vol. 10, No. 5, 2002, pp. 1611-1618.

Extended European Search Report on EP20813936.0 dtd May 19, 2022 (11 pages).

Hu et al., "Synthesis, structure-activity relationship studies and biological evaluation of novel 2, 5-disubstituted indole derivatives as anticancer agents", Chemical Biology & Drug Design, vol. 88, No. 5, 2016, pp. 766-778.

Manzoni et al., "Interfering with HuR-RNA Interaction : Design, Synthesis and Biological Characterization of Tanshinone Mimics as Novel, Effective HuR Inhibitors", Journal of Medicinal Chemistry, vol. 61, No. 4, 2018 (16 pages).

Wu et al., "The RNA Binding Protein HuR: A Promising Drug Target for Anticancer Therapy", Curr. Cancer Drug Treatments, 2019, vol. 19, p. 382-399.

Xiaoqing et al., "Identification and Validation of Novel Small Molecule Disruptors of HuR-mRNA Interaction", ACS Chemical Biology, vol. 10, No. 6, 2015, pp. 1476-1484.

Non-Final Office Action on U.S. Appl. No. 17/914,287 mailed May 23, 2025.

Allegri et al., "Effects of HuR downregulation on anaplastic thyroid cancer cells", Oncology Letters, 15, 2018 pp. 575-579.

Brown, "Bioisosteres in Medicinal Chemistry", 2012, Wiley-VCH Verlag Gmbh & Co. KGaA.

Wang et al. "Cytoplasmic HuR expression correlates with angiogenesis, lymphangiogenesis, and poor outcome in lung cancer", Med Oncol, 28, 2011, pp. S577-S585, DOI 10.1007/s12032-010-9734-6.

* cited by examiner

INHIBITORS OF RNA-BINDING PROTEINS, COMPOSITIONS THEREOF, AND THERAPEUTIC USES THEROF

This application is a U.S. National Phase Application under 35 U.S.C. 371 of International Application No. PCT/US2020/031058, filed May 1, 2020, which claims the benefit of and priority to U.S. Provisional Appl. No. 62/841,600, filed May 1, 2019, the entire contents of each of which are incorporated herein by reference.

U.S. GOVERNMENT RIGHTS

This invention was made with government support under CA178831, CA191785, and CA243445 awarded by National Institutes of Health, and under W81XWH-16-1-0729 awarded by the Department of Defense. The government has certain rights in the invention.

FIELD

The present technology is directed to compounds (as well as intermediates thereof), compositions, and methods related to inhibition of the interaction between RNA-binding proteins—such as Hu antigen R (HuR)—and the cellular targets of such RNA-binding proteins. The technology is suited to treat varying types of cancer.

SUMMARY

In an aspect, the present technology provides a compound according to Formula I (I)

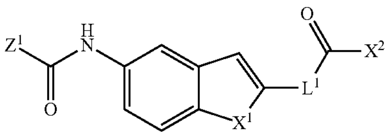

or a pharmaceutically acceptable salt thereof, wherein $Z^1$ is aryl, heteroaryl, or cycloalkyl;

$L^1$ is absent, $—CH_2—$, $—CH_2—CH_2—$, or $—CH{=}CH—$;

$X^1$ is O, NH, or S; and $X^2$ is OH, $NH_2$, NH—OH, NH—$NH_2$, or O—($C_1$-$C_6$ alkyl).

In a related aspect, a method is provided the includes administering a compound of Formula I to a subject. In any embodiment herein, it may be the subject is suffering from a condition, where the condition is a hyperproliferative disease with HuR overexpression. The hyperproliferative disease with HuR overexpression may include one or more of a colon cancer, a prostate cancer, a breast cancer, a brain cancer, an ovarian cancer, a pancreatic cancer, or a lung cancer.

DESCRIPTION OF THE DRAWINGS

FIG. 6 shows that at the concentrations of utilized KH-39, KH-56, and KH-58, KH-39 and KH-58 at least partially block HuR pull-down of target mRNAs in MDA-MB-231 cells; while KH-56 at the concentration utilized did not provide results statistically distinguishable from vehicle control, this is consistent with the data provided in this disclosure showing that KH-56 is less potent against MDA-MB-231 cells than both KH-39 and KH-58.

FIG. 9 shows that 10 μM KH-39 and 5 μM KH-58 clearly inhibited MDA-MB-231 cell invasion. While KH-56 at the concentration used did not provide a statistically significant difference in the image as compared to the DMSO control, this is consistent with the data provided in this disclosure showing that KH-56 is less potent against MDA-MB-231 cells than both KH-39 and KH-58.

FIG. 11 illustrates that mice in KH-39 treated group gain bodyweight with similar trend to those in vehicle control group, indicating that KH-39 is well-tolerated in vivo.

DETAILED DESCRIPTION

Figure 1A:
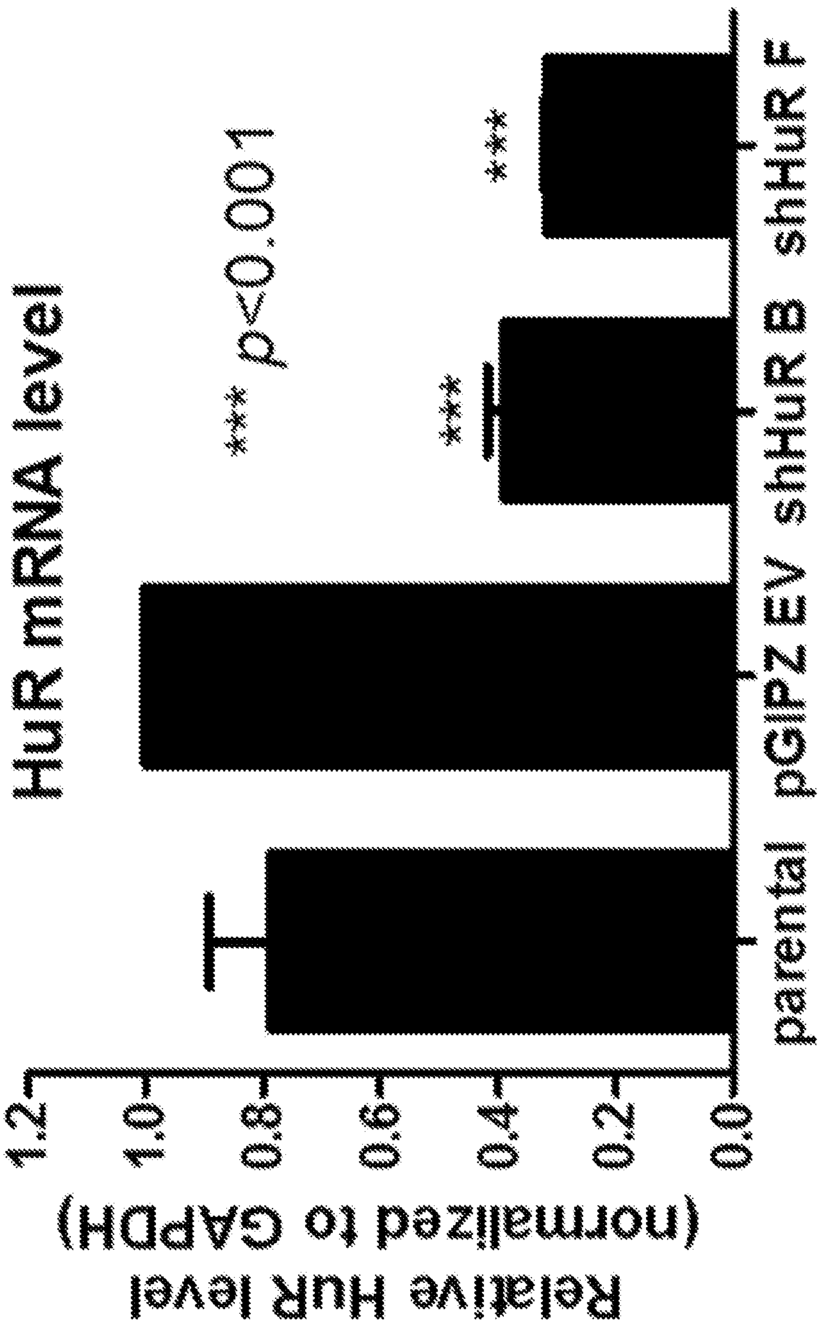
FIGS. 1A-F provide the results of studies illustrating RNA-binding protein Hu antigen R (HuR) is involved in chemo/radiation-induced tumor response. HuR knock-down by shRNAs in PC3 cells (FIG. 1A) resulted in reduced cell growth and colony formation (FIG. 1*i*). Docetaxel (TXT) treatment increased the mRNA levels of HuR target Musashi 2 (Msi2) in PC3 cells (FIG. 1C), but not in PC3 with HuR knock-down (FIG. 1D), indicating that HuR is required for chemo-induced response. X-ray radiation also increased the mRNA level of HuR target Msi2 (FIG. 1E). HuR knock-down by siRNA sensitized cancer cells to X-ray radiation, with an enhancement ratio (ER) of 1.5 versus the negative control (NC) siRNA (FIG. 1F).
Figure 1B:
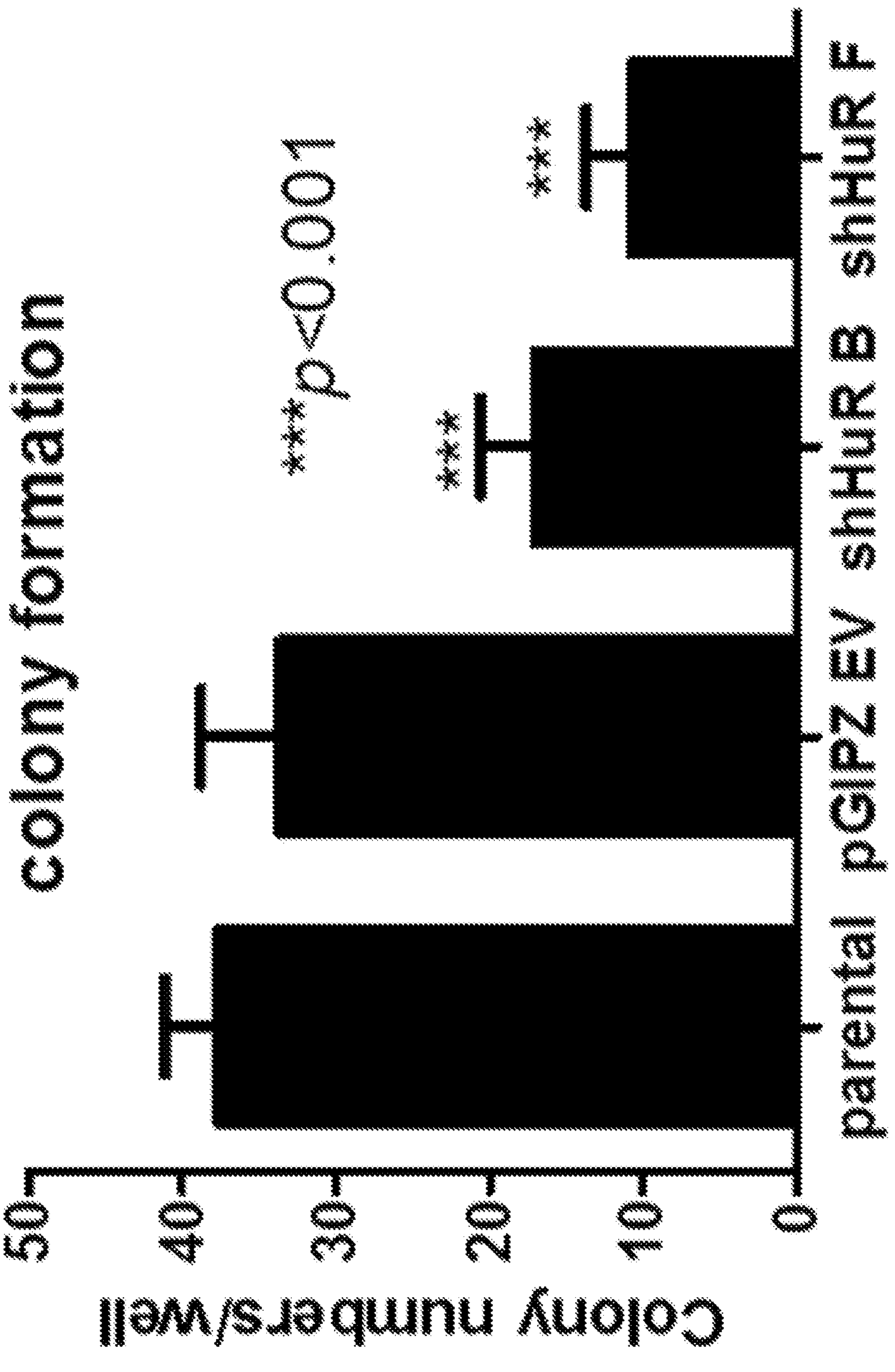
Figure 1C:
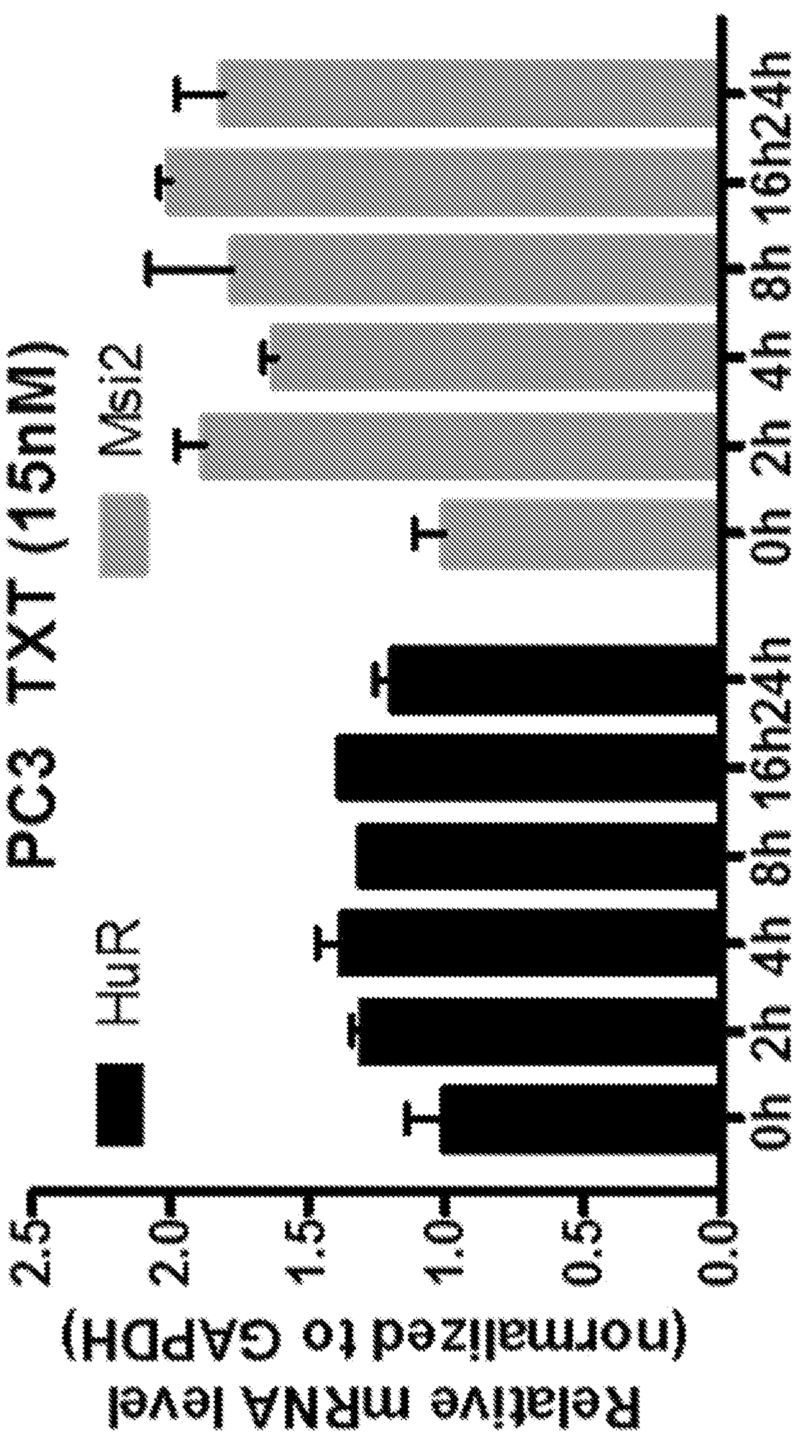
Figure 1D:
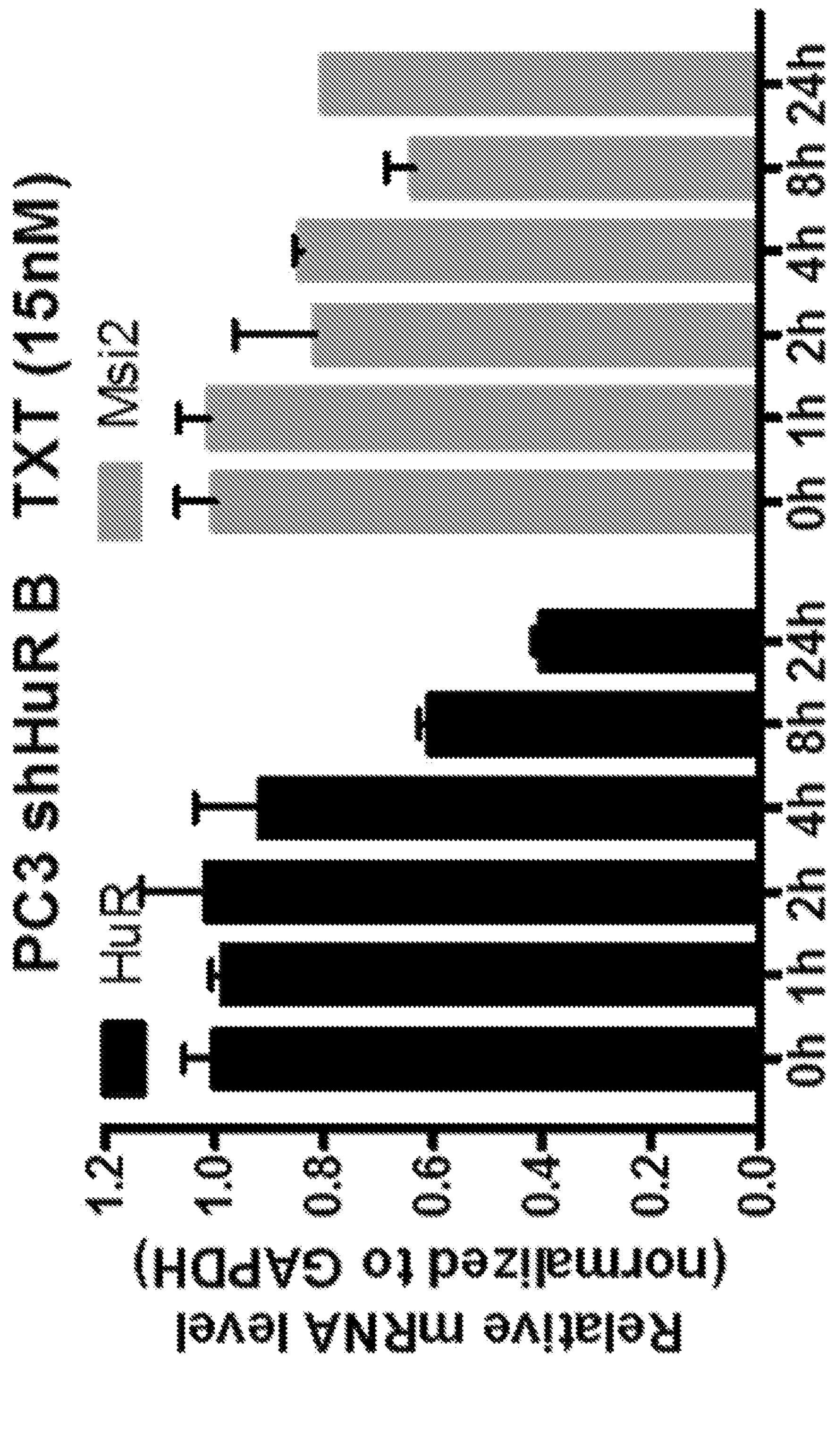
Figure 1E:
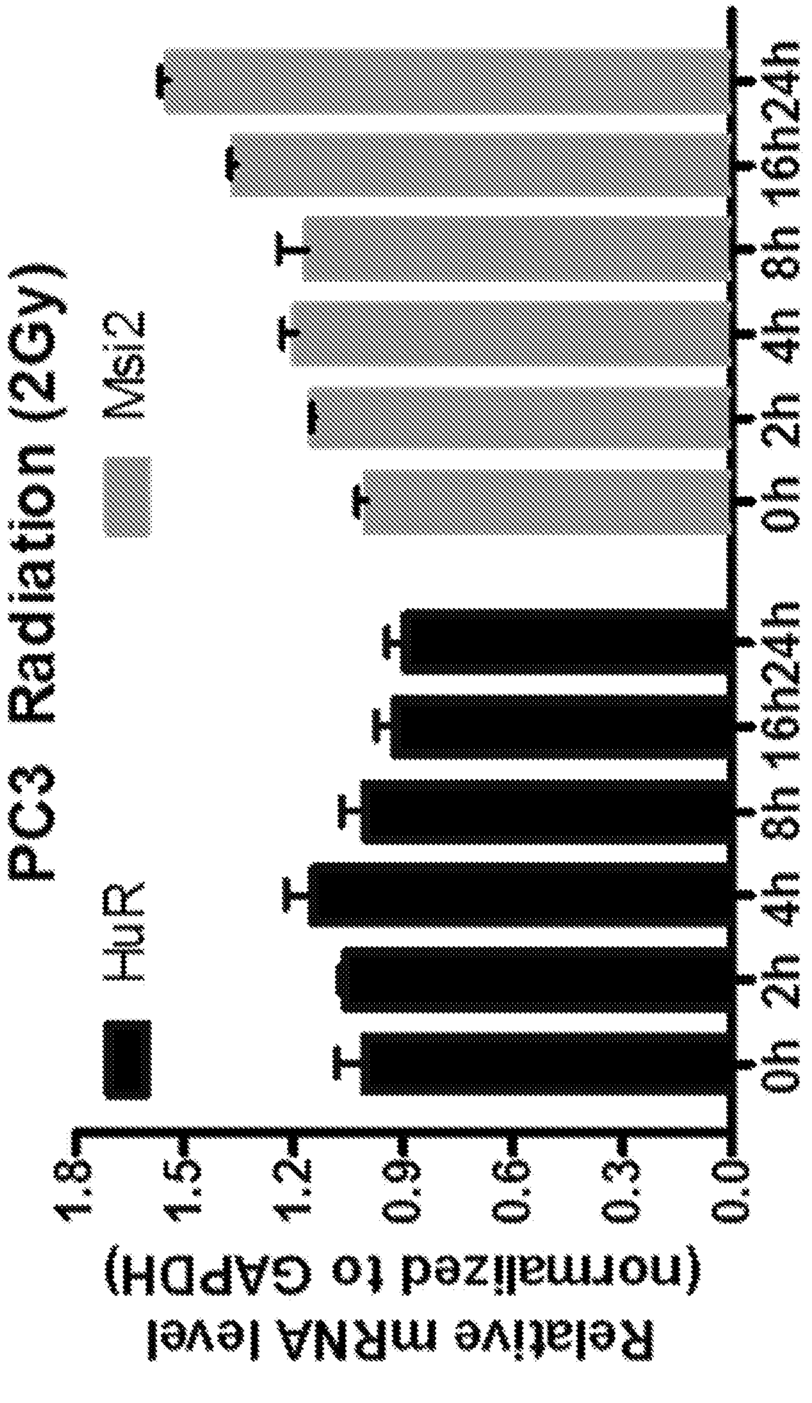
Figure 1F:
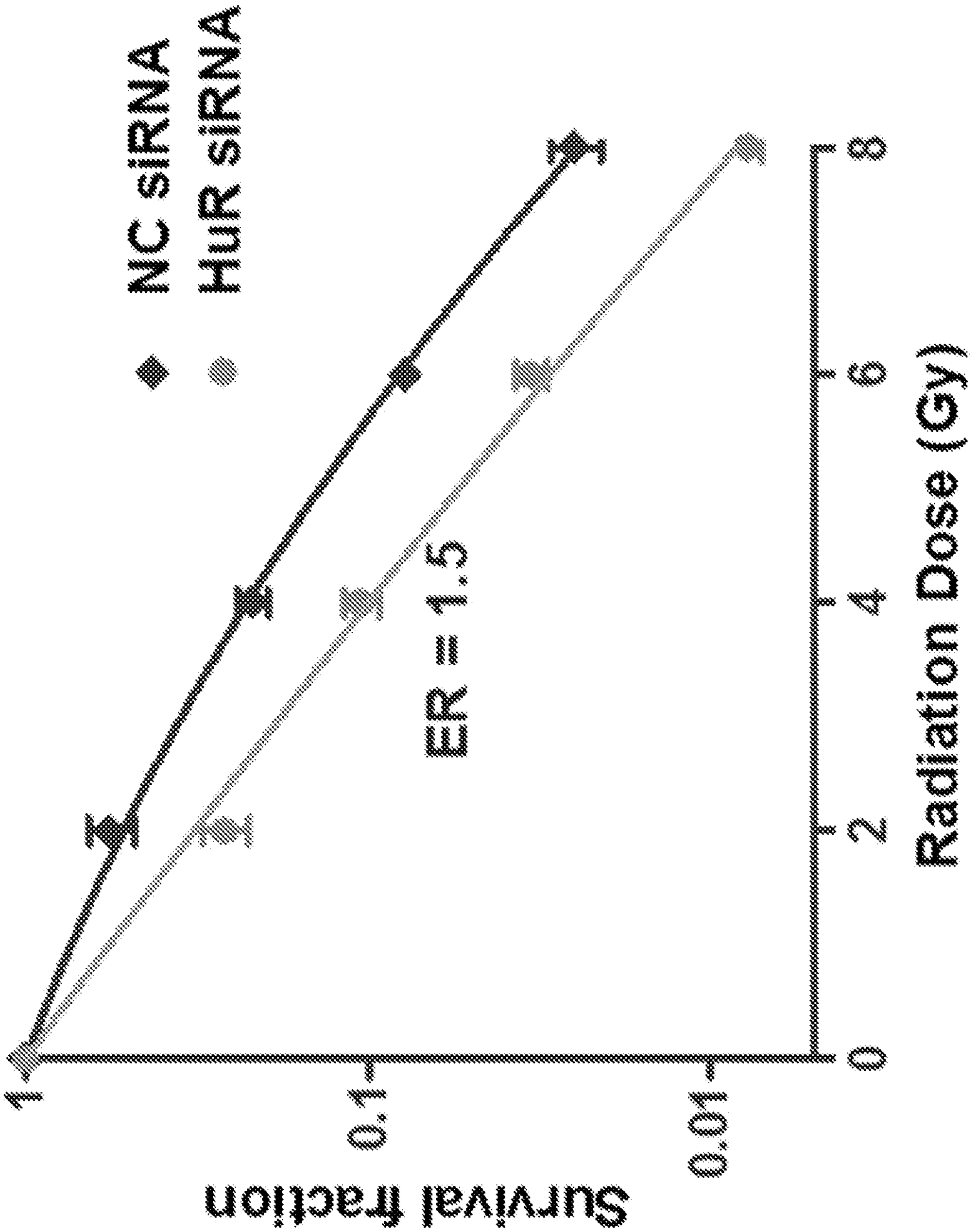

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would be understood to mean "9 wt. % to 11 wt. %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; alkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi—and tricyclic ring systems include both bridged cycloalkyl groups and fused rings, such as, but not limited to, bicyclo[2.1.1]hexane, adamantyl, decalinyl, and the like. Cycloalkyl groups may be substituted or unsubstituted. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Cycloalkylalkyl groups may be substituted or unsubstituted. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, among others. Alkenyl groups may be substituted or unsubstituted. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl. Cycloalkenyl groups may be substituted or unsubstituted.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to $-C{\equiv}CH$, $-C{\equiv}CCH_3$, $-CH_2C{\equiv}CCH_3$, $-C{\equiv}CCH_2CH(CH_2CH_3)_2$, among others. Alkynyl groups may be substituted or unsubstituted. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Aryl groups may be substituted or unsubstituted. Representative substituted aryl groups may be mono-substituted or substituted more than once. For example, mono-substituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Heterocyclyl groups may be substituted or unsubstituted. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, thiazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds. Heteroaryl groups may be substituted or unsubstituted. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Aryloxy and arylalkoxy groups may each be may be substituted or unsubstituted. Representative substituted aryloxy and arylalkoxy groups may be substituted one or more times with substituents such as those listed above.

The term "carboxylate" as used herein refers to a —COOH group.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is $NH_2$, methylamino, dimethylamino, ethylamino, diethylamino, propylamino, isopropylamino, phenylamino, or benzylamino.

The term "sulfonamido" includes S- and N-sulfonamide groups, i.e., $—SO_2NR^{78}R^{79}$ and $—NR^{78}SO_2R^{79}$ groups, respectively. $R^{78}$ and $R^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups ($—SO_2NH_2$). In some embodiments herein, the sulfonamido is $—NHSO_2$-alkyl and is referred to as the "alkylsulfonylamino" group.

The term "thiol" refers to —SH groups, while "sulfides" include $—SR^{80}$ groups, "sulfoxides" include $—S(O)R^{81}$ groups, "sulfones" include $—SO_2R^{82}$ groups, and "sulfonyls" include $—SO_2OR^{83}$. $R^{80}$, $R^{81}$, $R^{82}$, and $R^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to $—NR^{84}—C(O)—NR^{85}R^{86}$ groups. $R^{84}$, $R^{85}$, and $R^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to $—C(NR^{87})NR^{88}R^{89}$ and $—NR^{87}C(NR^{88})R^{89}$, wherein $R^{87}$, $R^{88}$, and $R^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to $—NR^{90}C(NR^{91})NR^{92}R^{93}$, wherein $R^{90}$, $R^{91}$, $R^{92}$ and $R^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to $—C(R^{94})=C(R^{95})NR^{96}R^{97}$ and $—NR^{94}C(R^{95})=C(R^{96})R^{97}$, wherein $R^{94}$, $R^{95}$, $R^{96}$ and $R^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, $—O^-$. A "hydroxyalkyl" group is a hydroxyl-substituted alkyl group, such as $HO—CH_2—$.

The term "imide" refers to $—C(O)NR^{98}C(O)R^{99}$, wherein $R^{98}$ and $R^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to $—CR^{100}(NR^{101})$ and $—N(CR^{100}R^{101})$ groups, wherein $R^{100}$ and $R^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that $R^{100}$ and $R^{101}$ are not both simultaneously hydrogen.

The term "nitro" as used herein refers to an $—NO_2$ group.

The term "trifluoromethyl" as used herein refers to $—CF_3$.

The term "trifluoromethoxy" as used herein refers to $—OCF_3$.

The term "azido" refers to $—N_3$.

The term "trialkyl ammonium" refers to a $—N(alkyl)_3$ group. A trialkylammonium group is positively charged and thus typically has an associated anion, such as halogen anion.

The term "isocyano" refers to —NC.

The term "isothiocyano" refers to —NCS.

The term "pentafluorosulfanyl" refers to $—SF_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms. The phrase "and/or" as used in this paragraph and the present disclosure will be understood to mean any one of the recited members individually or a combination of any two or more thereof—for example, "A, B, and/or C" would mean "A, B, C, A and B, A and C, or B and C."

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

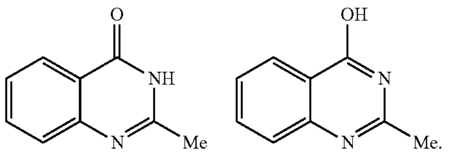

As another example, guanidines may exhibit the following isomeric forms in protic organic solution, also referred to as tautomers of each other:

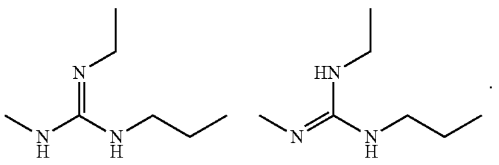

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided preceding the claims. The disclosures of these publications, patents and published patent specifications are hereby incorporated by reference into the present disclosure.

The Present Technology

Post-transcriptional gene regulation occurs at the levels of pre-mRNA splicing and maturation, as well as mRNA transport, editing, storage, stability, and translation. This level of gene regulation is essential for normal development, but when dysregulated, has many implications in disease conditions, including cancer. These functions are mediated by RNA-binding proteins (RBPs), which thus present targets for cancer therapy.

The RBP Hu antigen R ("HuR") is a member of the embryonic lethal abnormal vision ("ELAV") family that binds to adenine- and uridine-rich elements (collectively, "ARE") located in the 3'- or 5'-untranslated region ("UTR") of target mRNAs. [1] HuR is elevated in a broad range of cancer tissues compared with the corresponding normal tissues[2] In early reports, upregulated HuR in brain and colon cancers was linked to the enhanced expression of COX-2, VEGF, TGF-β, IL-8, and other cancer-associated proteins[3, 4]. Subsequent studies revealed that HuR was broadly overexpressed in virtually all malignancies tested, including cancers of the colon[2, 5, 6], prostate[7, 8], breast[9], brain[3], ovaries[10] pancreas[11], and lung[12]. Elevated cytoplasmic accumulation of HuR correlates with high-grade malignancy and serves as a prognostic factor of poor clinical outcome in those cancers[13-15].

Moreover, HuR is proposed to play a causal role in tumor development/progression. Cancer cells with elevated HuR produced significantly larger tumors than those arising from control populations in a mouse xenograft model[2], while reduced HuR level led to decreased tumor size[16].

HuR contains three RNA recognition motifs ("RRM"), of which RRM1 and RRM2 are involved in RNA binding, whereas RRM3 does not contribute to RNA binding but is needed for cooperative assembly of HuR oligomers on RNA.[17] Recently the crystal structure of two N-terminal RRM domains (namely, RRM1 and RRM2) of HuR complexed with RNA was reported.[18] HuR target mRNAs bear AREs in their 3'- or 5'-UTRs. Many cytokine and proto-oncogene mRNAs have been identified as containing AREs within their 3'-UTRs, which confer a short mRNA half-life.[19] Cytoplasmic binding of HuR to these ARE-containing mRNAs is generally accepted to lead to mRNA stabilization and increased translation[20, 21]. HuR promotes tumorigenesis by interacting with a subset of mRNAs which encode proteins implement in different tumor processes including cell proliferation, cell survival, angiogenesis, invasion, and metastasis[13-15]. HuR also promotes the translation of several target mRNAs encoding proteins that are involved in cancer treatment resistance[15, 22, 23]. HuR up-regulates the oncogenic Musashi1 (Msi1)[2], Musashi2 (Msi2)[25, 26] and anti-apoptotic proteins, Bcl-2[22] and XIAP[23], via binding AREs and promoting mRNA stability and translation, thus leading to activation of Wnt/Notch signaling pathways and inhibition of apoptosis. Wnt/Notch pathways are involved in cancer stem cells (CSCs)[27-30].

Figure 2:
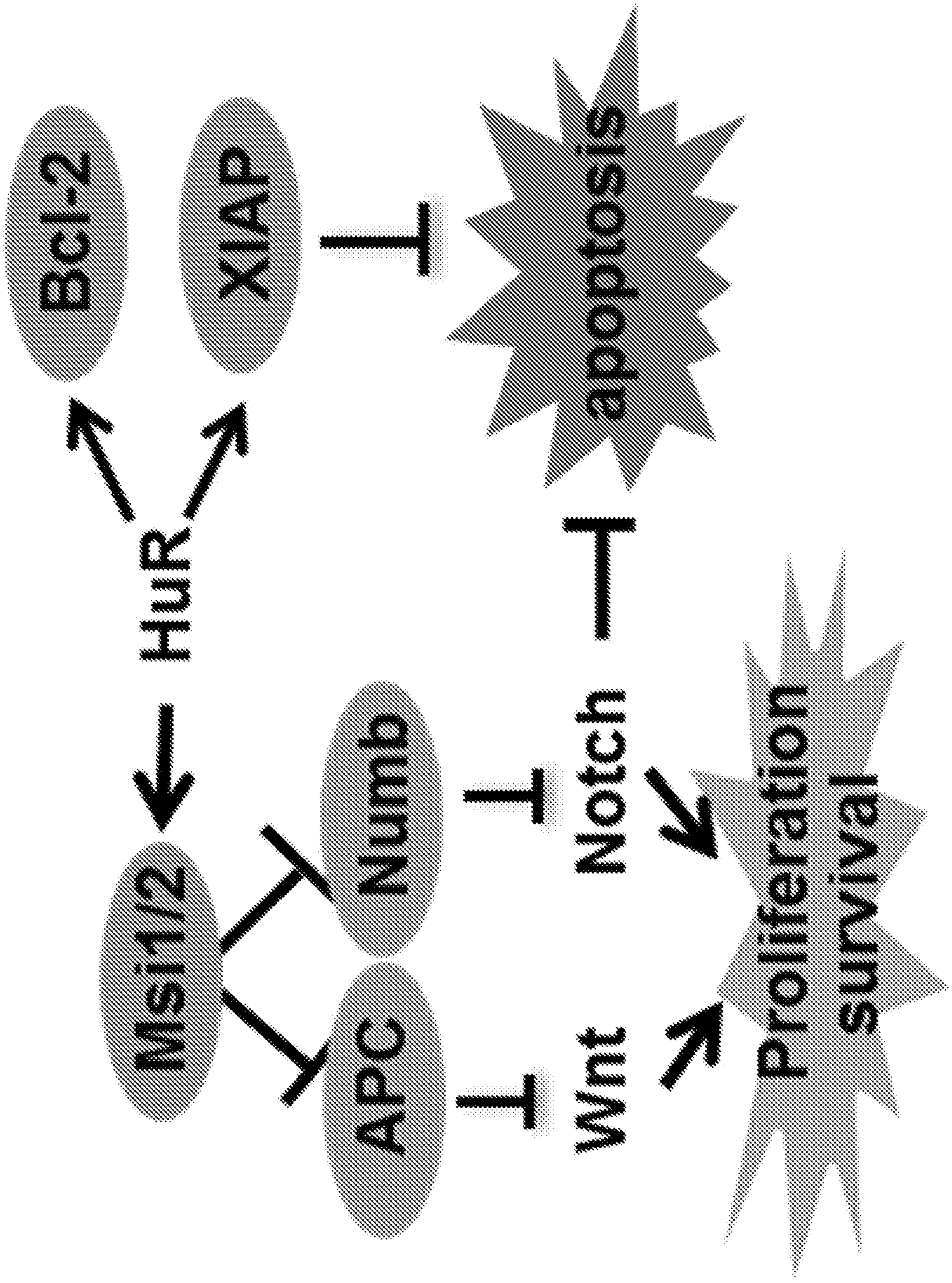
FIG. 2 provides a schematic of the proposed influence of HuR on apoptosis and Notch/Wnt signaling pathways. Musashi 1 and Musashi 2 (Msil/2) act through Notch and Wnt signaling to stimulate cell proliferation and survival and inhibit apoptosis. HuR is implicated in both pathways via increasing stability and translation of Msil/2 mRNA. HuR also inhibits apoptosis by up-regulating anti-apoptotic genes Bcl-2 and XIAP.

Consistent with the literature, our preliminary studies presently disclosed here (FIG. 1) also show that HuR knock-down resulted in inhibition of tumor cell growth/colony formation and sensitization to chemo/radiation, and chemo/radiation led to the HuR-mediated upregulation of Msi1/2, followed with Wnt/Notch activation. Without being bound by theory, it appears cancer cells use HuR, a master switch of multiple oncogenic mRNAs, as a response to counter chemo/radiation and to promote survival, thus rendering the cancer cells with HuR overexpression resistant to chemo/radiotherapy (See FIG. 2). Furthermore, among the HuR downstream signaling pathways, HuR-Bcl-2/XIAP and HuR-Msi1/2 pathways appear to be involved in the HuR-mediated chemo/radioresistance. Taken together, the published studies and our work indicate that HuR is a cancer therapy target.

Although there are many examples of compounds which specifically interfere with protein-protein interactions, there is limited success of drug discovery for protein-RNA interactions, especially for HuR.

The present technology is directed to compounds and compositions that inhibit the binding of RNA and HuR, as well as methods of using such compounds and compositions for inducing preferential inhibition and death of the cells with HuR overexpression and/or downstream signaling dysregulation, and for sensitizing such cells to the induction of cell death and/or growth inhibition by the conventional therapies.

In an aspect, the present technology provides a compound according to Formula I (I)

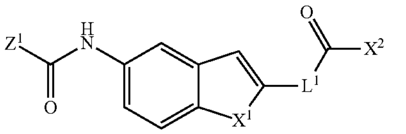

or a pharmaceutically acceptable salt thereof, where $Z^1$ is aryl, heteroaryl, or cycloalkyl; $L^1$ is absent, —$CH_2$—, —$CH_2$—$CH_2$—, or —CH═CH—; $X^1$ is O, NH, or S; and $X^2$ is OH, $NH_2$, NH—OH, NH—$NH_2$, or O—($C_1$-$C_6$ alkyl). In any embodiment disclosed herein, it may be that $Z^1$ is

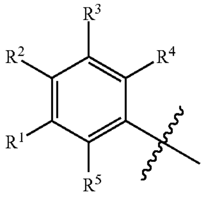
,
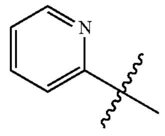
, or
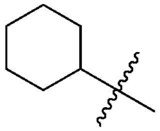
, where $R^1$, $R^2$, $R^3$, $R^4$, and $R^5$ are each independently H, halo, hydroxy, amino, cyano, trifluoromethyl, thiol, alkylthio, sulfoxide, sulfone, nitro, pentafluorosulfanyl, carboxylate, amide, ester, $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, or aryloyloxy group, where any two adjacent $R^1$, $R^2$, $R^3$, $R^4$, and $R^5$ may join to form a 5-membered alkyl, heteroalkyl, aryl or heteroaryl. In any embodiment herein, it may be that $R^1$, $R^2$, $R^3$, $R^4$, and $R^5$ are each independently H, halo, hydroxy, amino, cyano, trifluoromethyl, thiol, nitro, pentafluorosulfanyl, or $C_1$-$C_6$ alkyl, where any two adjacent $R^1$, $R^2$, $R^3$, $R^4$, and $R^5$ may join to form a 5-membered or 6-membered alkyl or aryl. In any embodiment herein, it may be that $R^1$, $R^2$, $R^3$, $R^4$, and $R^5$ are each independently H, halo, amino, trifluoromethyl, nitro, pentafluorosulfanyl, or $C_1$-$C_4$ alkyl, where any two adjacent $R^1$, $R^2$, $R^3$, $R^4$, and $R^5$ may join to form a 5-membered or 6-membered alkyl or aryl.

In any embodiment herein, it may be that the compound is of Formula IA (IA)

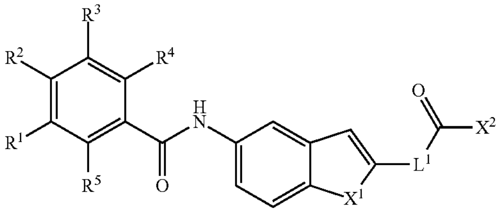

or a pharmaceutically acceptable salt thereof, where

Li is absent, —$CH_2$—, —$CH_2$—$CH_2$—, or —CH═CH—;

$R^1$, $R^2$, $R^3$, $R^4$, and $R^5$ are each independently H, halo, hydroxy, amino, cyano, trifluoromethyl, thiol, alkylthio, sulfoxide, sulfone, nitro, pentafluorosulfanyl, carboxylate, amide, ester, $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, or aryloyloxy group, where any two adjacent $R^1$, $R^2$, $R^3$, $R^4$, and $R^5$ may join to form a 5-membered alkyl, heteroalkyl, aryl or heteroaryl, and provided that at least one of $R^1$, $R^2$, $R^3$, $R^4$, and $R^5$ is not H;

$X^1$ is O, NH, or S; and $X^2$ is OH, $NH_2$, NH—OH, NH—$NH_2$, or O—($C_1$-$C_6$ alkyl).

In any embodiment herein, it may be that $R^1$, $R^2$, $R^3$, $R^4$, and $R^5$ are each independently H, halo, hydroxy, amino, cyano, trifluoromethyl, thiol, nitro, pentafluorosulfanyl, or $C_1$-$C_6$ alkyl, where any two adjacent $R^1$, $R^2$, $R^3$, $R^4$, and $R^5$ may join to form a 5-membered or 6-membered alkyl or aryl, and provided that at least one of $R^1$, $R^2$, $R^3$, $R^4$, and $R^5$ is not H. In any embodiment herein, it may be that $R^1$, $R^2$, $R^3$, $R^4$, and $R^5$ are each independently H, halo, amino, trifluoromethyl, nitro, pentafluorosulfanyl, or $C_1$-$C_4$ alkyl, where any two adjacent $R^1$, $R^2$, $R^3$, $R^4$, and $R^5$ may join to form a 5-membered or 6-membered alkyl or aryl, and provided that at least one of $R^1$, $R^2$, $R^3$, $R^4$, and $R^5$ is not H.

In any embodiment herein, it may be that the compound is of Formula IB (IB)

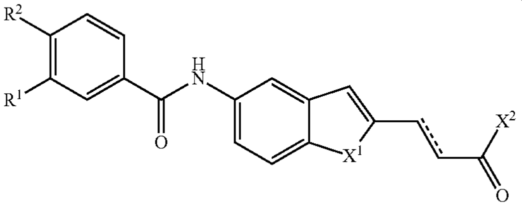

or a pharmaceutically acceptable salt thereof, wherein ------ is a single bond or a double bond; and provided that at least one of $R^1$ and $R^2$ is not H. Compounds of Formulas I, IA, and IB (as well as pharmaceutically acceptable salts thereof) will collectively be referred to as compounds of the present technology.

In any embodiment herein, it may be that $X^1$ is S. In any embodiment herein, it may be that $L^1$ is —CH═CH— in Formula I. In any embodiment herein, it may be that $L^1$ is —CH═CH— in Formula IA. In any embodiment herein, it may be that ------ is a double bond in Formula IB.

In any embodiment herein, it may be that $X^2$ is OH, $NH_2$, NH—OH, or NH—$NH_2$. It should be noted that compounds where $X^2$ is O—($C_1$-$C_6$ alkyl) are especially suited as intermediates in the synthesis of active compounds where $X^2$ is OH, $NH_2$, NH—OH, or NH—$NH_2$, as illustrated in the working examples. However, compounds where $X^2$ is O—($C_1$-$C_6$ alkyl) may themselves be used as pro-drug compounds (for example, where esterases in a subject will convert $X^2$ in vivo into OH).

In a related aspect of the present technology, a composition is provided that includes any embodiment disclosed herein of a compound of the present technology and a pharmaceutically acceptable carrier, excipient, filler, or agent (collectively referred to as "pharmaceutically acceptable carrier" unless otherwise indicated and/or specified). In a related aspect, a pharmaceutical composition is provided, the pharmaceutical composition including an effective amount of a compound of the present technology for treating a condition; and where the condition is a hyperproliferative disease with HuR overexpression. The hyperproliferative disease with HuR overexpression may include one or more of a colon cancer, a prostate cancer, a breast cancer (e.g., triple negative breast cancer), a brain cancer, an ovarian cancer, a pancreatic cancer, or a lung cancer.

In a further related aspect, a method is provided the includes administering a compound of the present technology to a subject. It may be the subject is suffering from a condition, where the condition is a hyperproliferative disease with HuR overexpression. The hyperproliferative disease with HuR overexpression may include one or more of a colon cancer, a prostate cancer, a breast cancer (e.g., triple negative breast cancer), a brain cancer, an ovarian cancer, a pancreatic cancer, or a lung cancer. It may be the method includes administering an effective amount of a compound of the present technology. Administration of a compound of the present technology may be via administration a pharmaceutical composition (as described herein) that includes a compound of the present technology.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of a hyperproliferative disease with HuR overexpression. Another example of an effective amount includes amounts or dosages that reduce the size of tumors associated with one or more of a colon cancer, a prostate cancer, a breast cancer (e.g., triple negative breast cancer), a brain cancer, an ovarian cancer, a pancreatic cancer, or a lung cancer that exhibit HuR overexpression. As used herein, a "subject" or "patient" is a mammal, such as a cat, dog, rodent or primate. Typically the subject is a human, and, preferably, a human suffering from or suspected of suffering from an addiction. The term "subject" and "patient" can be used interchangeably.

Thus, the instant present technology provides pharmaceutical compositions and medicaments comprising one or more compounds of the present technology and a pharmaceutically acceptable carrier or one or more excipients or fillers. The compositions may be used in the methods and treatments described herein. Such compositions and medicaments include a therapeutically effective amount of any compound as described herein, including but not limited to a compound of Formula I and/or a compound of Formula IA and/or a compound of Formula IB. The pharmaceutical composition may be packaged in unit dosage form. The unit dosage form is effective in treating a hyperproliferative disease with HuR overexpression when administered to a subject in need thereof.

The pharmaceutical compositions and medicaments may be prepared by mixing one or more compounds of the present technology with pharmaceutically acceptable carriers, excipients, binders, diluents or the like to prevent and treat a hyperproliferative disease with HuR overexpression. The compounds and compositions described herein may be used to prepare formulations and medicaments that prevent or treat a variety of disorders associated with a hyperproliferative disease with HuR overexpression. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount, such as by simply administering a compound of the present technology to a patient in increasing amounts until the progression of the condition/disease state is decreased or stopped. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

The compounds of the present technology may also be administered to a patient along with other conventional therapeutic agents that may be useful in the treatment a hyperproliferative disease with HuR overexpression. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially or synergistically be effective for the treatment of a hyperproliferative disease with HuR overexpression.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

The terms “associated” and/or “binding” can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to “binding” or “affinity” as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology. The examples herein are also presented in order to more fully illustrate the preferred aspects of the present technology. The examples should in no way be construed as limiting the scope of the present technology, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

EXAMPLES

All solvents and reagents were used as received from commercial suppliers, unless noted otherwise. $^1H$ and $^{13}C$ NMR spectra were recorded on a Bruker AM or Varian 400 spectrometer (operating at 400 and 101 MHz respectively) or a Bruker AVIII spectrometer (operating at 500 and 126 MHz respectively) in $CDCl_3$ with 0.03% TMS as an internal standard. The chemical shifts (6) reported are given in parts per million (ppm) and the coupling constants (J) are in Hertz (Hz). The spin multiplicities are reported as s=singlet, d=doublet, t=triplet, q=quartet, dd=doublet of doublet, ddd=doublet of doublet of doublet, dt=doublet of triplet, td=triplet of doublet, and m=multiplet. Microwave reactions were carried out using a Biotage Initiator Classic. Column chromatography separations were performed using the Teledyne Isco CombiFlash Rf using RediSep Rf silica gel columns. The analytical RPLC method used an Agilent 1200 RRLC system with UV detection (Agilent 1200 DAD SL) and mass detection (Agilent 6224 TOF). The analytical method conditions included a Waters Aquity BEH C18 column (2.1×50 mm, 1.7 μm) and elution with a linear gradient of 5% acetonitrile in pH 9.8 buffered aqueous ammonium formate to 100% acetonitrile at 0.4 mL/min flow rate. Automated preparative RP HPLC purification was performed using an Agilent 1200 Mass-Directed Fractionation system (Prep Pump G1361 with gradient extension, make-up pump G1311A, pH modification pump G1311A, HTS PAL autosampler, UV-DAD detection G1315D, fraction collector G1364B, and Agilent 6120 quadrupole spectrometer G6120A). The preparative chromatography conditions included a Waters X-Bridge C18 column (19×150 mm, 5 um, with 19×10-mm guard column), elution with a water and acetonitrile gradient, which increases 20% in acetonitrile content over 4 min at a flow rate of 20 mL/min (modified to pH 9.8 through addition of NH4OH by auxiliary pump), and sample dilution in DMSO. The preparative gradient, triggering thresholds, and UV wavelength were selected according to the analytical RP HPLC analysis of each crude sample. Compound purity was measured on the basis of peak integration (area under the curve) from UV-Vis absorbance at 214 nm, and compound identity was determined on the basis of mass spectral and NMR analyses.

An exemplary synthetic protocol for benzothiophene-containing esters, amides, carboxylic acids, hydroxamic acids, and acyl hydrazides is illustrated in Scheme 1.

Scheme 1.

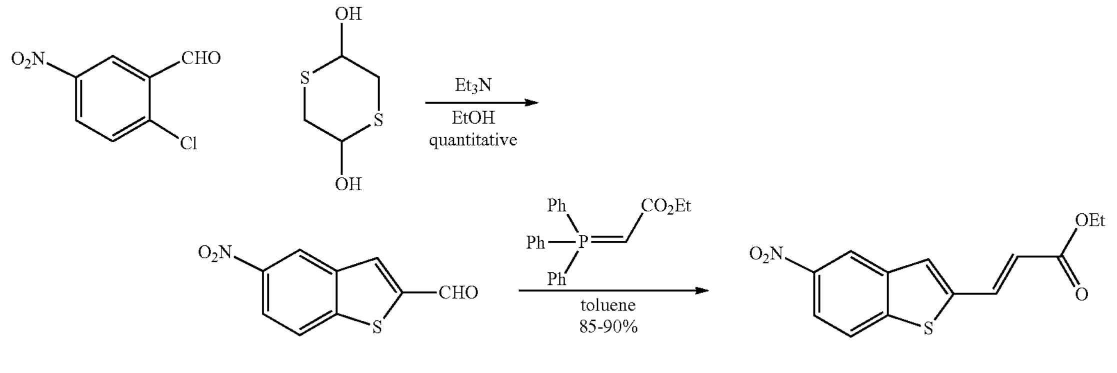

-continued
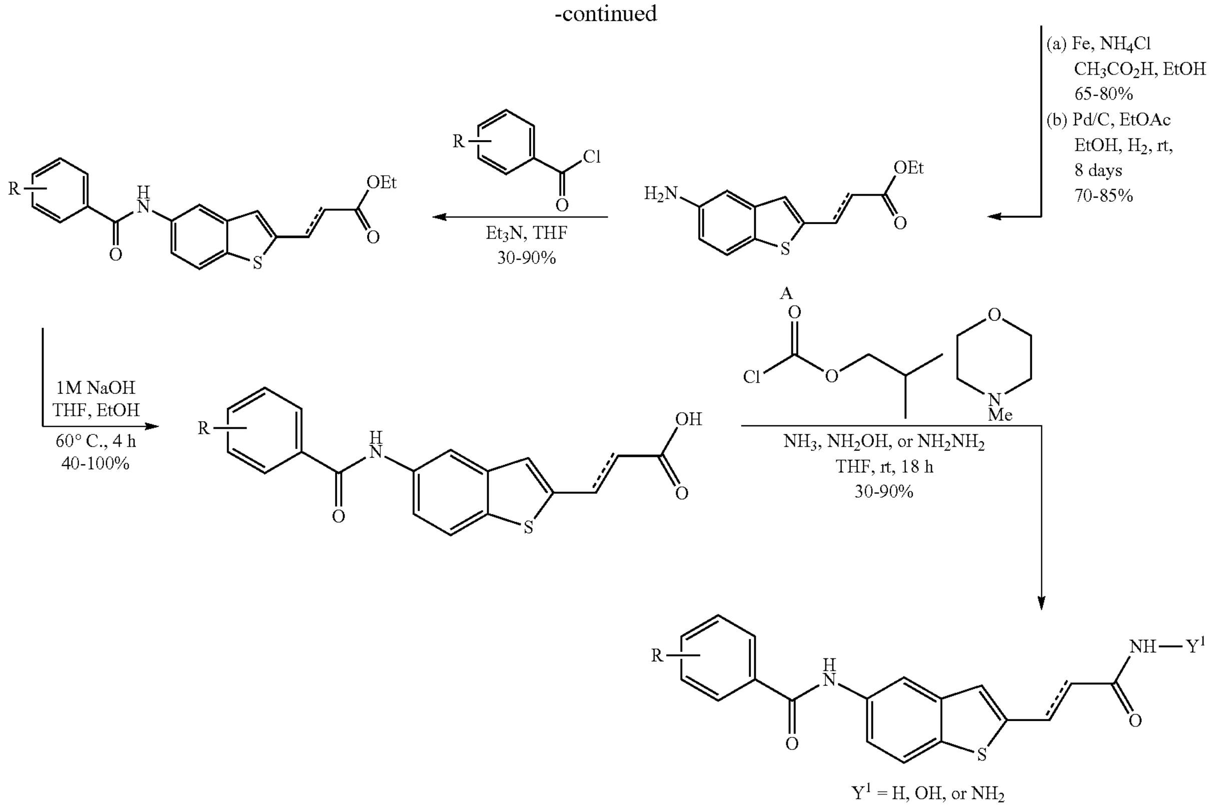
An exemplary synthetic protocol for indole-containing esters, amides, carboxylic acids, hydroxamic acids, and acyl hydrazides is illustrated in Scheme 2.

Scheme 2.
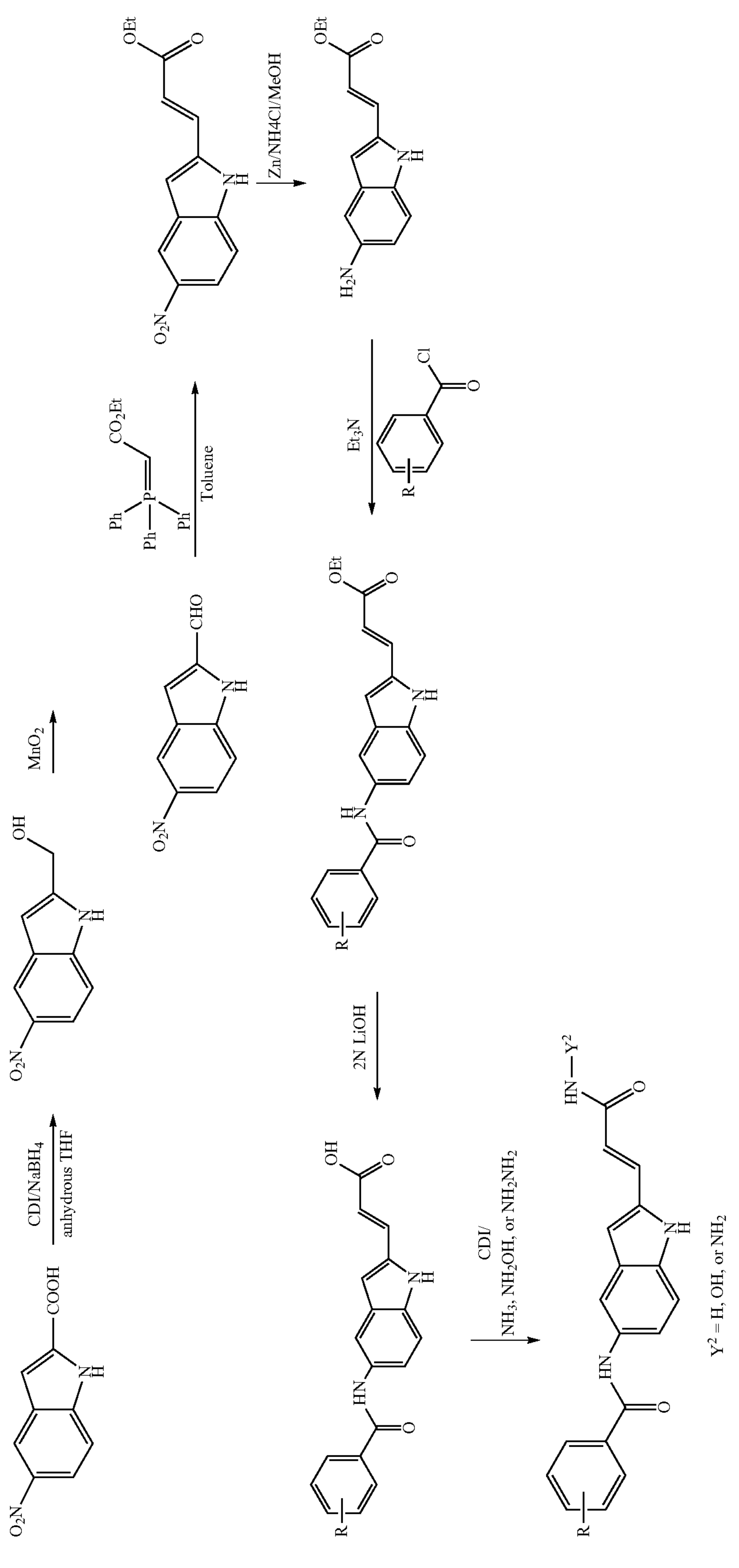
$Y^2$ = H, OH, or $NH_2$

Further exemplary synthetic protocols for benzothiophene-containing esters, amides, carboxylic acids, hydroxamic acids, and acyl hydrazides and for indole-containing esters, amides, carboxylic acids, hydroxamic acids, and acyl hydrazides are illustrated in Scheme 3.

Scheme 3.

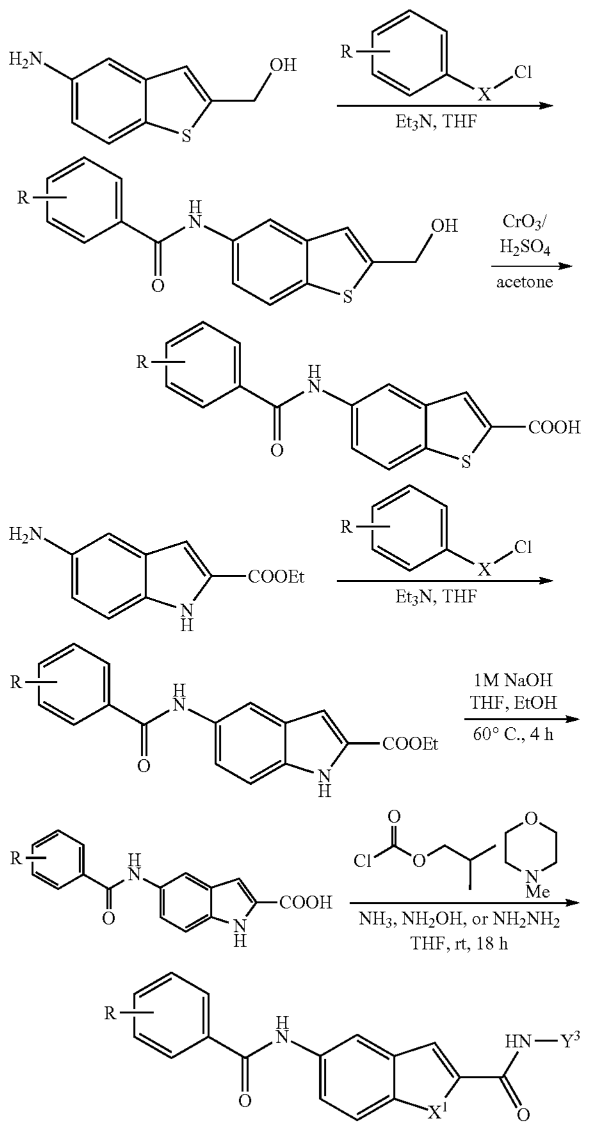

$X^1$ = S or NH
$Y^3$ = H, OH, or $NH_2$

Representative Procedure for Synthesis including Amide Coupling: To a solution of the aniline A (0.802 mmol, 1 eq.) in THE (4.27 mL) was added the corresponding benzoyl chloride (1.203 mmol, 1.5 eq.) followed by triethylamine (2.005 mmol, 3 eq.). The reaction mixture was stirred at 60° C. or rt for 16 h. Upon completion the reaction mixture was quenched with 1 N HCl and extracted with EtOAc (×3) and dried over anhydrous $Na_2SO_4$. The evaporated residue was purified via silica gel chromatography (normal phase combiflash using hexanes and ethyl acetate). Isolated the corresponding anilide as off-white solid.

Exemplary Synthesis: (E)-ethyl 3-(5-((4-((E)-(4-(dimethylamino)phenyl)diazenyl)phenyl)sulfonamido) benzo[b] thiophen-2-yl)acrylate (KH-16B; not of the present technology)

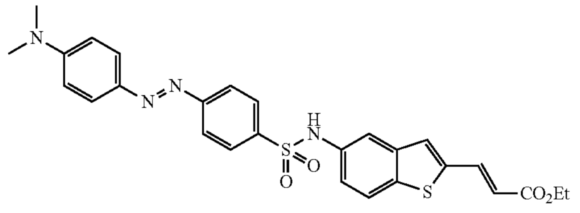 [SMILES: CCOC(=O)/C=C/c1cc2cc(NS(=O)(=O)c3ccc(/N=N/c4ccc(N(C)C)cc4)cc3)ccc2s1]

To a mixture of (E)-ethyl 3-(5-aminobenzo[b]thiophen-2-yl)acrylate (200 mg, 0.809 mmol) and $Et_3N$ (135 μL, 0.970 mmol) in tetrahydrofuran (4 mL), was added (E)-4-((4-(dimethylamino)phenyl)diazenyl)benzene-1-sulfonyl chloride (314 mg, 0.970 mmol). The mixture was stirred at 60° C. for 16 h. The reaction was cooled and solvent was removed. The residue was dissolved in EtOAc, washed with 1N NaOH, brine, dried over $MgSO_4$. The evaporated residue was purified via silica gel chromatography (EtOAc/hexanes=1:2, $R_f$=0.3) to afford a red solid (337.8 mg, 0.632 mmol, 78% yield). $^1$H NMR (400 MHz, DMSO-$d_6$) δ 10.46 (s, 1H), 7.92-7.68 (m, 9H), 7.59 (d, J=2.2 Hz, 1H), 7.19 (dd, J=8.7, 2.2 Hz, 1H), 6.88-6.76 (m, 2H), 6.26 (d, J=15.8 Hz, 1H), 4.17 (q, J=7.1 Hz, 2H), 3.05 (s, 6H), 1.23 (t, J=7.1 Hz, 3H). $^{13}$C NMR (101 MHz, DMSO) δ 165.5, 154.8, 153.2, 142.6, 140.1, 139.9, 138.9, 137.4, 135.7, 135.1, 129.3, 128.1, 125.5, 123.5, 122.2, 120.6, 119.3, 115.8, 111.6, 60.3, 39.8, 14.2. HRMS (m/z): calcd for $C_{27}H_{27}N_4O_4S_2$ ([M]$^+$+H) 535.1468; found 535.1508.

Exemplary Synthesis: (E)-3-(5-(4-((E)-(4-(dimethylamino)phenyl)diazenyl)phenylsulfonamido)benzo[b] thiophen-2-yl)acrylic acid (KH-16A; not of the Present Technology)

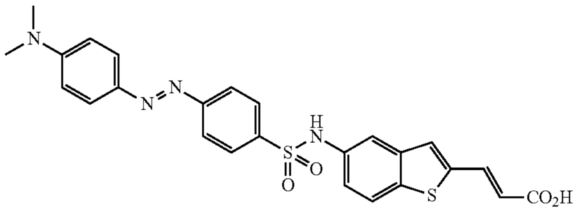 [SMILES: CN(C)c1ccc(/N=N/c2ccc(S(=O)(=O)Nc3ccc4sc(/C=C/C(=O)O)cc4c3)cc2)cc1]

To a solution of (E)-ethyl 3-(5-(4-((E)-(4-(dimethylamino)phenyl)diazenyl)phenylsulfonamido)benzo[b]thiophen-2-yl)acrylate (204.5 mg, 0.382 mmo) in tetrahydrofuran (1.9 mL), was added sodium hydroxide (10%, 1.1 mL, 2.68 mmol). The mixture was stirred at rt for 2 days. The reaction mixture was diluted with 30 mL water, extracted with EtOAc. The aqueous phase was acidified with HCl to pH=3, then extracted with EtOAc (50 mL×2). The combined organic phase was washed with brine, dried over $MgSO_4$. Solvent was removed under vacuo to give a red solid (194 mg, 0.382 mmol, 100% yield). $^1$H NMR (400 MHz, DMSO-$d_6$) δ 10.61 (s, 1H), 7.92-7.70 (m, 9H), 7.60 (d, J=2.1 Hz, 1H), 7.21 (dd, J=8.7, 2.1 Hz, 1H), 6.87-6.78 (m, 2H), 6.21 (d, J=15.7 Hz, 1H), 3.06 (s, 6H). $^{13}$C NMR (101 MHz, DMSO) δ 166.9, 154.8, 153.2, 142.7, 140.4, 139.9, 138.9, 137.0, 135.6, 135.1, 128.9, 128.1, 125.5, 123.5, 122.2, 120.5, 120.5, 115.8, 111.6, 39.8. HRMS (m/z): calcd for $C_{25}H_{23}N_4O_4S_2$ ([M]$^+$+H) 507.1155; found 507.1147.

Compounds KH-19A and KH-20A (each of the present technology) were synthesized using a similar procedure described for KH-16A, with the exception that for compounds KH-19A and KH-20A a reaction time of 5 days instead of 2 days was applied.

Exemplary Synthesis: (E)-3-(5-(4-((E)-(4-(dimethylamino)phenyl)diazenyl)phenylsulfonamido)benzo[b]thiophen-2-yl)-N-hydroxyacrylamide (KH-16; not of the Present Technology)

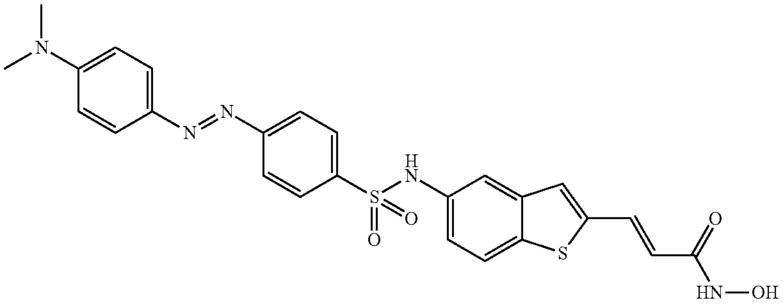 [SMILES: CN(C)c1ccc(/N=N/c2ccc(S(=O)(=O)Nc3ccc4sc(/C=C/C(=O)NO)cc4c3)cc2)cc1]

To a solution of (E)-3-(5-(4-((E)-(4-(dimethylamino)phenyl)diazenyl)phenylsulfonamido)benzo[b]thiophen-2-yl) acrylic acid (110.9 mg, 0.219 mmol) and 4-methylmorpholine (31.3 μL, 0.285 mmol) in tetrahydrofuran (1.1 mL), was added isobutyl carbonochloridate (34.1 μL, 0.263 mmol). The mixture was stirred at 0° C. for 30 min. The filtrate was added to the hydroxyamine solution formed by mixing a solution of hydroxylamine hydrochloride (45.6 mg, 0.657 mmol) in MeOH (1 mL) with potassium hydroxide (43.3 mg, 0.657 mmol) in MeOH (0.5 mL) for 15 min and then filtered. The reaction mixture was allowed to stir at rt for 30 min. Solvents were removed under vacuo and residue was purified via silica gel chromatography (DCM/MeOH=10:1, $R_f$=0.5) to give an orange solid (16.5 mg, 0.032 mmol, 14% yield). $^1$H NMR (400 MHz, DMSO-$d_6$) δ δ 7.88-7.81 (m, 2H), 7.81-7.72 (m, 4H), 7.67-7.59 (m, 2H), 7.52 (s, 1H), 7.42 (d, J=2.1 Hz, 1H), 7.06 (dd, J=8.6, 2.2 Hz, 1H), 6.86-6.77 (m, 2H), 6.20 (d, J=15.5 Hz, 1H), 3.05 (s, 6H). $^{13}$C NMR (101 MHz, DMSO) δ 162.0, 153.8, 152.9, 142.6, 140.2, 140.2, 131.9, 127.8, 127.7, 125.1, 122.5, 121.8, 121.3, 120.1, 114.7, 111.5, 39.8. HRMS (m/z): calcd for $C_{25}H_{24}N_5O_4S_2$ ([M]$^+$+H) 522.1264; found 522.1318.

Compounds KH-19 and KH-20 (each of the present technology) were synthesized using a similar procedure as described for KH-16.

(E)-4-(tert-butyl)-N-(2-(3-(hydroxyamino)-3-oxoprop-1-en-1-yl)benzo[b]thiophen-5-yl)benzamide (KH-19)

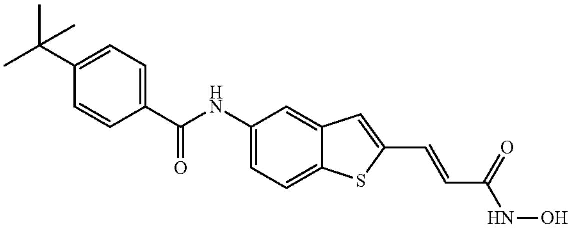 [SMILES: CC(C)(C)c1ccc(C(=O)Nc2ccc3sc(/C=C/C(=O)NO)cc3c2)cc1]

Yellow solid (28.7 mg, 0.073 mmol, 44% yield). $^1$H NMR (400 MHz, DMSO-$d_6$) δ 10.32 (s, 1H), 8.37 (d, J=2.0 Hz, 1H), 7.95-7.87 (m, 3H), 7.75-7.71 (m, 3H), 7.59-7.51 (m, 2H), 6.29 (d, J=15.5 Hz, 1H), 1.32 (s, 9H). $^{13}$C NMR (101 MHz, DMSO) δ 165.6, 161.9, 154.4, 140.6, 139.8, 136.7, 133.8, 132.2, 131.8, 128.0, 127.5, 125.1, 122.5, 120.5, 119.8, 115.0, 34.77, 30.9. HRMS (m/z): calcd for $C_{22}H_{23}N_2O_3S$ ([M]$^+$+H) 395.1424; found 395.1426.

(E)-N-hydroxy-3-(5-pivalamidobenzo[b]thiophen-2-yl)acrylamide (KH-20)

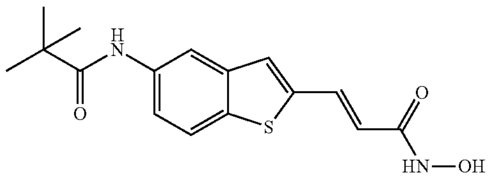 [SMILES: CC(C)(C)C(=O)Nc1ccc2sc(/C=C/C(=O)NO)cc2c1]

White solid (77.2 mg, 0.242 mmol, 74% yield). $^1$H NMR (400 MHz, DMSO-$d_6$) δ 9.32 (s, 1H), 8.20 (d, J=2.1 Hz, 1H), 7.83 (d, J=8.7 Hz, 1H), 7.76-7.64 (m, 2H), 7.60 (dd, J=8.8, 2.1 Hz, 1H), 6.27 (d, J=15.5 Hz, 1H), 1.24 (s, 9H). $^{13}$C NMR (101 MHz, DMSO) δ 176.6, 162.0, 140.5, 139.8, 136.8, 133.5, 131.9, 128.0, 122.3, 120.4, 120.0, 115.1, 39.2, 27.2. HRMS (m/z): calcd for $C_{16}H_{19}N_2O_{43}S$ ([M]$^+$+H) 319.1111; found 319.1109.

(E)-3-(5-(4-(tert-butyl)benzamido)benzo[b]thiophen-2-yl)acrylic acid (KH-19A)

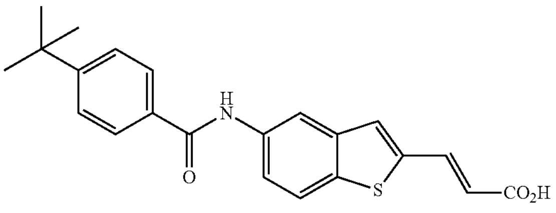 [SMILES: CC(C)(C)c1ccc(C(=O)Nc2ccc3sc(/C=C/C(=O)O)cc3c2)cc1]

White solid (89.4 mg, 0.236 mmol, 82% yield). $^1$H NMR (400 MHz, DMSO-$d_6$) δ 10.33 (s, 1H), 8.39 (d, J=2.1 Hz, 1H), 7.95-7.83 (m, 4H), 7.82 (s, 1H), 7.74 (dd, J=8.8, 2.1 Hz, 1H), 7.59-7.52 (m, 2H), 6.23 (d, J=15.7 Hz, 1H), 1.32 (s, 9H). $^{13}C$ NMR (101 MHz, DMSO) δ 167.0, 165.88, 154.6, 139.9, 139.8, 137.3, 136.8, 134.6, 132.2, 129.4, 127.6, 125.3, 122.7, 120.4, 120.2, 115.3, 34.8, 31.0. HRMS (m/z): calcd for $C_{22}H_{22}NO_3S$ ($[M]^+$+H) 380.1315; found 380.1314.

(E)-3-(5-pivalamidobenzo[b]thiophen-2-yl)acrylic acid (KH-20A)

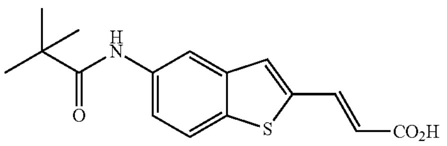 [SMILES: CC(C)(C)C(=O)Nc1ccc2sc(/C=C/C(=O)O)cc2c1]

White solid (169.4 mg, 0.558 mmol, 84% yield). $^1H$ NMR (400 MHz, DMSO-$d_6$) δ 12.53 (s, 1H), 9.33 (s, 1H), 8.25 (d, J=2.0 Hz, 1H), 7.90-7.80 (m, 2H), 7.78 (s, 1H), 7.62 (dd, J=8.8, 2.1 Hz, 1H), 6.21 (dd, J=15.7, 0.5 Hz, 1H), 1.25 (s, 9H). $^{13}C$ NMR (101 MHz, DMSO) δ 176.5, 166.8, 139.58, 139.56, 137.2, 136.8, 134.1, 129.3, 122.3, 120.4, 120.0, 115.2, 39.1, 27.2. HRMS (m/z): calcd for $C_{16}H_{18}NO_3S$ ($[M]^+$+H) 304.1002; found 304.1006.

Exemplary Synthesis: (E)-3-(5-((4-(tert-butyl)phenyl)sulfonamido)benzo[b]thiophen-2-yl)acrylamide (KH-3C; not of the Present Technology)

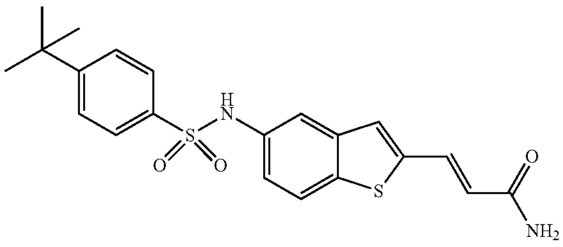 [SMILES: CC(C)(C)c1ccc(S(=O)(=O)Nc2ccc3sc(/C=C/C(N)=O)cc3c2)cc1]

To a solution of (E)-3-(5-(4-(tert-butyl)phenylsulfonamido)benzo[b]thiophen-2-yl)acrylic acid (100 mg, 0.241 mmol) and 4-methylmorpholine (66.1 µl, 0.602 mmol) in tetrahydrofuran (1.2 mL), was added isobutyl carbonochloridate (78 µl, 0.602 mmol). The mixture was stirred at 0° C. for 30 min. The filtrate was added to ammonium hydroxide (28%, 344 µl, 2.407 mmol). The reaction mixture was allowed to stir at rt for 16 h. Solvents were removed under vacuo and residue was purified via reverse phase purification (MeCN/water: 10%→100%) to give a white solid (61.5 mg, 0.148 mmol, 62% yield). $^1H$ NMR (400 MHz, DMSO-$d_6$) δ 7.80 (d, J=8.6 Hz, 1H), 7.75-7.68 (m, 2H), 7.68-7.58 (m, 3H), 7.57-7.53 (m, 3H), 7.22-7.13 (m, 2H), 6.41 (d, J=15.6 Hz, 1H), 1.22 (s, 9H). $^{13}C$ NMR (101 MHz, DMSO) δ 165.9, 155.8, 141.2, 140.1, 136.8, 135.4, 134.4, 132.6, 127.7, 126.5, 126.1, 123.9, 123.3, 119.4, 114.5, 34.8, 30.7. HRMS (m/z): calcd for $C_{21}H_{23}N_2O_3S_2$ ($[M]^+$+H) 415.1145; found 415.1149.

Compounds KH-19C, KH-22C, and KH-19E (each of the present technology) were synthesized using a similar procedure as described for KH-3C.

(E)-N-(2-(3-amino-3-oxoprop-1-en-1-yl)benzo[b]thiophen-5-yl)-4-(tert-butyl)benzamide (KH-19C)

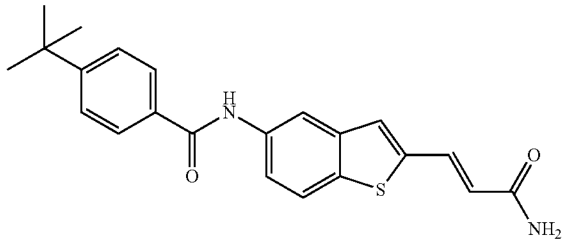 [SMILES: CC(C)(C)c1ccc(C(=O)Nc2ccc3sc(/C=C/C(N)=O)cc3c2)cc1]

White solid (18.8 mg, 0.050 mmol, 63% yield). $^1H$ NMR (400 MHz, DMSO-$d_6$) δ 10.31 (s, 1H), 8.36 (d, J=2.1 Hz, 1H), 7.92-7.89 (m, 3H), 7.77-7.63 (m, 4H), 7.55 (d, J=8.2 Hz, 2H), 7.20 (s, 1H), 6.45 (d, J=15.5 Hz, 1H), 1.32 (s, 9H). $^{13}C$ NMR (101 MHz, DMSO) δ 166.0, 165.6, 154.4, 140.7, 139.8, 136.7, 133.9, 132.8, 132.2, 128.0, 127.5, 125.1, 123.6, 122.5, 119.8, 115.0, 34.7, 30.9. HRMS (m/z): calcd for $C_{22}H_{23}N_2O_2S$ ($[M]^+$+H) 379.1475; found 379.1473.

(E)-4-(tert-butyl)-N-(2-(3-hydrazinyl-3-oxoprop-1-en-1-yl)benzo[b]thiophen-5-yl)benzamide (KH-19E)

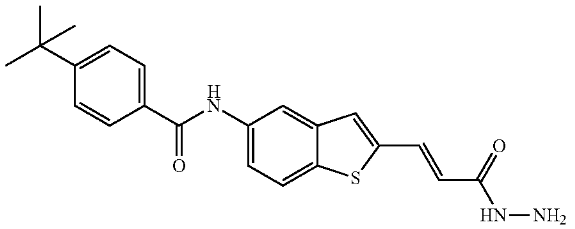 [SMILES: CC(C)(C)c1ccc(C(=O)Nc2ccc3sc(/C=C/C(=O)NN)cc3c2)cc1]

White solid (16.9 mg, 0.043 mmol, 54% yield). $^1H$ NMR (400 MHz, DMSO-$d_6$) δ 10.31 (s, 1H), 9.46 (s, 1H), 8.35 (d, J=2.0 Hz, 1H), 7.92-7.89 (m, 3H), 7.75-7.67 (m, 3H), 7.59-7.52 (m, 2H), 6.38 (d, J=15.5 Hz, 1H), 4.51 (s, 2H), 1.32 (s, 9H). $^{13}C$ NMR (101 MHz, DMSO) δ 165.7, 163.8, 154.5, 140.8, 139.9, 136.7, 133.9, 132.2, 131.8, 128.0, 127.6, 125.2, 122.6, 121.6, 119.9, 115.1, 34.7, 31.0. HRMS (m/z): calcd for $C_{22}H_{24}N_3O_2S$ ($[M]^+$+H) 394.1584; found 394.1562.

N-(2-(3-amino-3-oxopropyl)benzo[b]thiophen-5-yl)-4-(tert-butyl)benzamide (KH-22C)

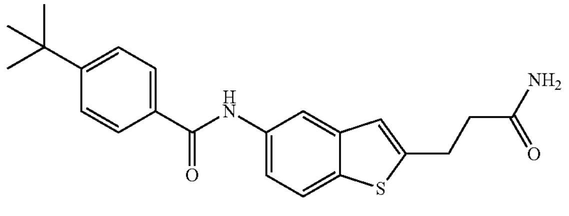 [SMILES: CC(C)(C)c1ccc(C(=O)Nc2ccc3sc(CCC(N)=O)cc3c2)cc1]

Off-white solid (0.011 g, 61.0% yield). $^1H$ NMR (400 MHz, DMSO-$d_6$) δ 10.23 (s, 1H), 8.23 (d, J=2.0 Hz, 1H), 7.94-7.87 (m, 2H), 7.81 (d, J=8.6 Hz, 1H), 7.61 (dd, J=8.7, 2.1 Hz, 1H), 7.57-7.51 (m, 2H), 7.40 (s, 1H), 7.15 (s, 1H), 6.86 (s, 1H), 3.10 (t, J=7.3 Hz, 3H), 2.50 (t, J=7.1 Hz, 2H), 1.33 (s, 9H). $^{13}$C NMR (101 MHz, DMSO-$d_6$) δ 172.8, 165.5, 154.3, 146.2, 140.0, 136.1, 133.7, 132.3, 127.5, 125.2, 122.1, 121.0, 117.6, 114.0, 36.1, 34.7, 31.0, 26.0.

Representative Procedure for Synthesis of Carboxylic Acids:

To a solution of ester (0.127 mmol, 1 eq.) in a mixture of EtOH (0.740 mL) and THE (0.740 mL) (ratio volume, 1:1) was added 1M sodium hydroxide (0.254 mmol, 0.254 mL, 2 eq.) and the reaction was refluxed (65° C.) for 4 h. Upon completion, the reaction mixture was concentrated and diluted with 1N HCl. The aqueous layer was extracted with EtOAc (×3). The combined layer was washed with brine, dried over anhydrous $Na_2SO_4$, and concentrated in vacuo to provide corresponding carboxylic acids as off-white solid. As additional step of reverse phase chromatography (using water and acetonitrile, 0 to 100% gradient) could be employed should it prove necessary for further purification.

3-(5-(4-(tert-Butyl)benzamido)benzo[b]thiophen-2-yl)propanoic acid (KH-22A)

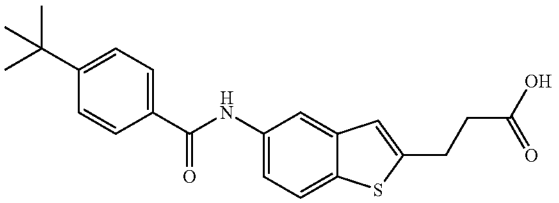 [SMILES: CC(C)(C)c1ccc(C(=O)Nc2ccc3sc(CCC(=O)O)cc3c2)cc1]

This compound was prepared following Representative Procedure for Synthesis of Carboxylic Acids using ethyl 3-(5-(4-(tert-butyl)benzamido)benzo[b]thiophen-2-yl)propanoate (0.127 mmol, 0.052 g) and 1 M sodium hydroxide (0.254 mmol, 0.254 mL). Yield: 52 mg (100%), off-white solid; $^1$H NMR (400 MHz, DMSO-$d_6$) δ 12.33 (s, 0H), 10.23 (s, 1H), 8.23 (d, J=1.9 Hz, 1H), 7.95-7.86 (m, 2H), 7.82 (d, J=8.7 Hz, 1H), 7.61 (dd, J=8.7, 2.1 Hz, 1H), 7.59-7.51 (m, 2H), 7.17 (d, J=0.6 Hz, 2H), 3.12 (t, J=7.1 Hz, 2H), 2.69 (d, J=7.3 Hz, 2H), 1.33 (s, 9H). $^{13}$C NMR (101 MHz, DMSO-$d_6$) δ 173.3, 165.5, 154.3, 145.5, 140.0, 136.1, 133.7, 132.3, 127.5, 125.1, 122.1, 121.3, 117.7, 114.1, 34.8, 34.7, 31.0, 25.6.

3-(5-(4-Methylbenzamido)benzo[b]thiophen-2-yl)propanoic acid (KH-27A)

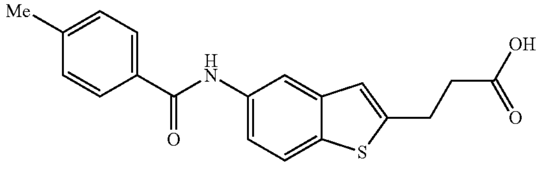 [SMILES: Cc1ccc(C(=O)Nc2ccc3sc(CCC(=O)O)cc3c2)cc1]

This compound was prepared following Representative Procedure for Synthesis of Carboxylic Acids using ethyl 3-(5-(4-methylbenzamido)benzo[b]thiophen-2-yl)propanoate (0.669 mmol, 0.246 g) and 1 M sodium hydroxide (1.339 mmol, 1.339 mL). Yield: 0.200 g (74%), off-white solid; $^1$H NMR (400 MHz, DMSO-$d_6$) δ 10.20 (s, 1H), 8.22 (d, J=2.0 Hz, 1H), 7.92-7.84 (m, 2H), 7.80 (d, J=8.7 Hz, 1H), 7.60 (dd, J=8.7, 2.1 Hz, 1H), 7.37-7.26 (m, 2H), 7.15 (d, J=0.9 Hz, 1H), 3.14-3.04 (m, 2H), 2.66 (t, J=7.3 Hz, 2H), 2.38 (s, 3H). $^{13}$C NMR (101 MHz, DMSO-$d_6$) δ 173.7, 165.8, 146.0, 141.9, 140.4, 136.6, 134.1, 132.6, 129.3, 128.1, 122.5, 121.7, 118.2, 114.6, 35.3, 26.0, 21.5.

3-(5-(3-(tert-butyl)benzamido)benzo[b]thiophen-2-yl)propanoic acid (KH-30A)

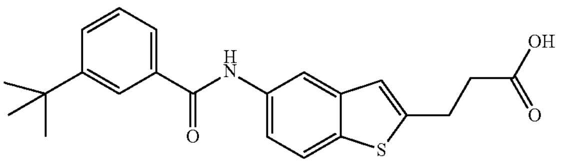 [SMILES: CC(C)(C)c1cccc(C(=O)Nc2ccc3sc(CCC(=O)O)cc3c2)c1]

This compound was prepared following Representative Procedure for Synthesis of Carboxylic Acids using ethyl 3-(5-(3-(tert-butyl)benzamido)benzo[b]thiophen-2-yl)propanoate (0.618 mmol, 0.253 g) and 1 M sodium hydroxide (1.236 mmol, 1.236 mL). Yield: 0.103 g (44%), off-white solid; $^1$H NMR (400 MHz, DMSO-$d_6$) δ 10.27 (s, 1H), 8.21 (d, J=2.0 Hz, 1H), 7.95 (t, J=1.9 Hz, 1H), 7.83 (d, J=8.7 Hz, 1H), 7.79 (dt, J=7.7, 1.4 Hz, 1H), 7.67-7.57 (m, 2H), 7.46 (t, J=7.8 Hz, 1H), 7.18 (d, J=1.0 Hz, 1H), 3.12 (t, J=7.2 Hz, 3H), 2.68 (t, J=7.3 Hz, 2H), 1.35 (s, 9H). $^{13}$C NMR (101 MHz, DMSO-$d_6$) δ 173.3, 165.8, 150.9, 145.6, 140.0, 136.0, 134.8, 133.8, 128.5, 128.1, 124.8, 124.3, 122.1, 121.2, 117.9, 114.4, 34.8, 34.6, 31.1, 25.6.

3-(5-(4-Fluorobenzamido)benzo[b]thiophen-2-yl)propanoic acid (KH-28A)

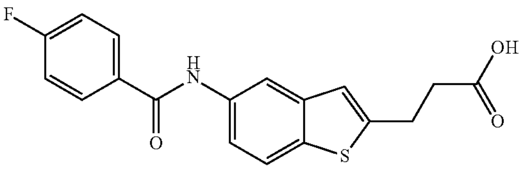 [SMILES: O=C(O)CCc1cc2cc(NC(=O)c3ccc(F)cc3)ccc2s1]

This compound was prepared following Representative Procedure for Synthesis of Carboxylic Acids using ethyl 3-(5-(4-fluorobenzamido)benzo[b]thiophen-2-yl)propanoate (0.606 mmol, 0.225 g) and 1 M sodium hydroxide (1.212 mmol, 1.212 mL). Yield: 0.192 g (79%), off-white solid; $^1$H NMR (400 MHz, DMSO-$d_6$) δ 12.30 (s, 1H), 10.32 (s, 1H), 8.22 (d, J=2.0 Hz, 1H), 8.11-7.99 (m, 2H), 7.83 (d, J=8.7 Hz, 1H), 7.61 (dd, J=8.7, 2.1 Hz, 1H), 7.42-7.31 (m, 2H), 7.18 (d, J=0.5 Hz, 1H), 3.12 (t, J=7.2 Hz, 3H), 2.68 (t, J=7.3 Hz, 2H). $^{13}$C NMR (101 MHz, DMSO-$d_6$) δ 173.25, 164.38, 164.02 (d, J=248.9 Hz), 145.60, 139.99, 135.93, 133.87, 131.41 (d, J=3.0 Hz), 130.35 (d, J=9.1 Hz), 121.69 (d, J=88.5 Hz), 117.71, 115.42, 115.20, 114.22, 34.81, 25.56.

(E)-3-(5-(3-(tert-Butyl)benzamido)benzo[b]thiophen-2-yl)acrylic acid (KH-31A)

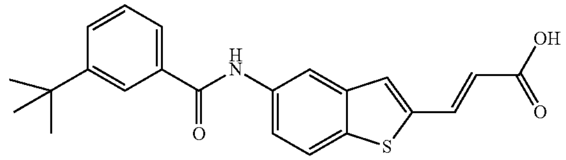 [SMILES: CC(C)(C)c1cccc(C(=O)Nc2ccc3sc(/C=C/C(=O)O)cc3c2)c1]

This compound was prepared following Representative Procedure for Synthesis of Carboxylic Acids using ethyl (E)-3-(5-(3-(tert-butyl)benzamido)benzo[b]thiophen-2-yl) acrylate (0.206 mmol, 0.084 g) and 1 M sodium hydroxide (0.412 mmol, 0.412 mL). Yield: 0.038 g (49%), off-white solid; $^1$H NMR (400 MHz, DMSO-$d_6$) δ 10.36 (s, 1H), 8.38 (d, J=1.9 Hz, 1H), 7.97-7.91 (m, 2H), 7.89-7.82 (m, 2H), 7.80 (dt, J=7.7, 1.3 Hz, 1H), 7.75 (dd, J=8.8, 2.1 Hz, 1H), 7.64 (ddd, J=7.9, 2.1, 1.1 Hz, 1H), 6.24 (d, J=15.9 Hz, 1H), 1.35 (s, 9H). $^{13}$C NMR (101 MHz, DMSO-$d_6$) δ 167.4, 166.5, 151.4, 140.3, 140.1, 137.1, 135.1, 135.0, 129.8, 129.0, 128.6, 125.3, 124.8, 123.1, 120.9, 120.7, 116.7, 115.9, 35.1, 31.5.

(E)-3-(5-(4-Fluorobenzamido)benzo[b]thiophen-2-yl)acrylic acid (KH-23A)

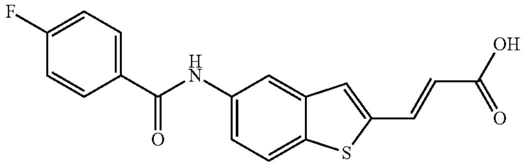 [SMILES: O=C(O)/C=C/c1cc2cc(NC(=O)c3ccc(F)cc3)ccc2s1]

This compound was prepared following Representative Procedure for Synthesis of Carboxylic Acids using ethyl (E)-3-(5-(4-fluorobenzamido)benzo[b]thiophen-2-yl)acrylate (0.241 mmol, 0.089 g) and 1 M sodium hydroxide (0.482 mmol, 0.482 mL). Yield: 0.039 g (47%), off-white solid; $^1$H NMR (400 MHz, DMSO-$d_6$) δ 10.42 (s, 1H), 8.38 (d, J=2.0 Hz, 1H), 8.13-8.01 (m, 2H), 7.93 (d, J=8.7 Hz, 1H), 7.87-7.77 (m, 2H), 7.73 (dd, J=8.8, 2.1 Hz, 1H), 7.47-7.26 (m, 2H), 6.24 (d, J=15.7 Hz, 1H).

(E)-3-(5-(4-(Trifluoromethyl)benzamido)benzo[b]thiophen-2-yl)acrylic acid (KH-32A)

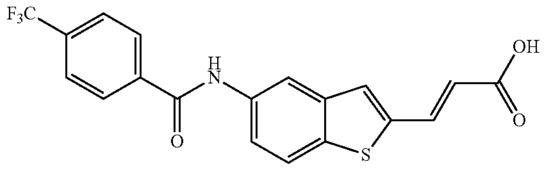 [SMILES: O=C(O)/C=C/c1cc2cc(NC(=O)c3ccc(C(F)(F)F)cc3)ccc2s1]

This compound was prepared following Representative Procedure for Synthesis of Carboxylic Acids using ethyl (E)-3-(5-(4-(trifluoromethyl)benzamido)benzo[b]thiophen-2-yl)acrylate (0.191 mmol, 0.08 g) and 1 M sodium hydroxide (0.381 mmol, 0.381 mL). Yield: 0.044 g (59%), off-white solid; $^1$H NMR (400 MHz, DMSO-$d_6$) δ 10.62 (s, 1H), 8.41 (d, J=2.0 Hz, 1H), 8.23-8.11 (m, 2H), 8.00-7.89 (m, 3H), 7.85 (t, J=7.8 Hz, 2H), 7.75 (dd, J=8.8, 2.1 Hz, 1H), 6.24 (d, J=15.7 Hz, 1H).

(E)-3-(5-(4-(pentafluoro-$\lambda^6$-sulfanyl)benzamido)benzo[b]thiophen-2-yl)acrylic acid (KH-33A)

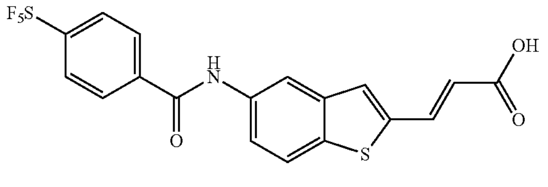

This compound was prepared following Representative Procedure for Synthesis of Carboxylic Acids using ethyl (E)-3-(5-(4-(pentafluoro-16-sulfanyl)benzamido)benzo[b]thiophen-2-yl)acrylate (0.276 mmol, 0.132 g) and 1 M sodium hydroxide (0.553 mmol, 0.553 mL). Yield: 0.044 g (59%), off-white solid; $^{19}$F NMR (376 MHz, DMSO-$d_6$) δ 86.21 (p, J=151.7 Hz), 63.76 (d, J=150.5 Hz); $^1$H NMR (400 MHz, DMSO-$d_6$) δ 10.65 (s, 1H), 8.40 (d, J=2.0 Hz, 1H), 8.21-8.13 (m, 2H), 8.13-8.06 (m, 2H), 7.95 (d, J=8.8 Hz, 1H), 7.89-7.81 (m, 2H), 7.74 (dd, J=8.8, 2.1 Hz, 1H), 6.25 (d, J=15.8 Hz, 1H).

3-(5-(4-(pentafluoro-$\lambda^6$-sulfanyl)benzamido)benzo[b]thiophen-2-yl)propanoic acid (KH-34A)

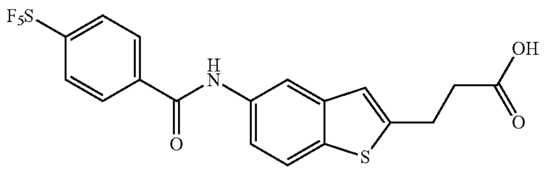

This compound was prepared following Representative Procedure for Synthesis of Carboxylic Acids using ethyl 3-(5-(4-(pentafluoro-16-sulfanyl)benzamido)benzo[b]thiophen-2-yl)propanoate (0.273 mmol, 0.131 g) and 1 M sodium hydroxide (0.546 mmol, 0.546 mL). Yield: 0.074 g (60%), off-white solid; $^{19}$F NMR (376 MHz, DMSO-$d_6$) δ 86.27 (p, J=150.5 Hz), 63.77 (d, J=150.3 Hz); $^1$H NMR (400 MHz, DMSO-$d_6$) δ 10.57 (s, 1H), 8.24 (d, J=2.0 Hz, 1H), 8.19-8.13 (m, 2H), 8.12-8.03 (m, 2H), 7.85 (d, J=8.7 Hz, 1H), 7.61 (dd, J=8.7, 2.1 Hz, 1H), 7.20 (s, 1H), 3.12 (t, J=7.2 Hz, 2H), 2.68 (t, J=7.3 Hz, 2H).

(E)-3-(5-(4-(Dimethylamino)benzamido)benzo[b]thiophen-2-yl)acrylic acid (KH-36A)

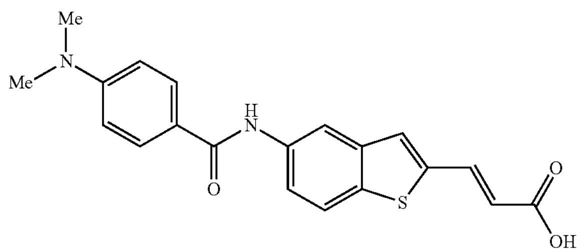 [SMILES: CN(C)c1ccc(C(=O)Nc2ccc3sc(/C=C/C(=O)O)cc3c2)cc1]

This compound was prepared following Representative Procedure for Synthesis of Carboxylic Acids using ethyl (E)-3-(5-(4-(dimethylamino)benzamido)benzo[b]thiophen-2-yl)acrylate (35 mg), and provided as the hydrochloride salt. Yield: 31% (10 mg). Pale brown solid. IR 2921, 1683, 1652 $cm^{-1}$; $^{1}H$ NMR (400 MHz, DMSO-$d_6$) δ 10.01 (s, 1H), 8.39 (m, 1H), 7.91-7.88 (complex, 3H), 7.83 (d, J=8.0 Hz, 2H), 7.75 (dd, J=8.8, 2.0 Hz, 1H), 6.78 (d, J=9.1 Hz, 2H), 6.22 (d, J=15.8 Hz, 1H), 3.01 (s, 6H) ppm; $^{13}C$ NMR (100 MHz, DMSO-$d_6$) δ 167.0, 165.3, 152.4, 139.7, 139.6, 137.34, 137.27, 134.0, 129.5, 129.2, 122.5, 120.9, 120.4, 119.9, 115.0, 110.8, 39.8 ppm; HRMS (ESI): Calcd. for $C_{20}H_{19}N_2O_3S$ $(M+H)^+$: 367.1116; found 367.1115.

3-(5-(4-(Dimethylamino)benzamido)benzo[b]thiophen-2-yl)propanoic acid (KH-38A)

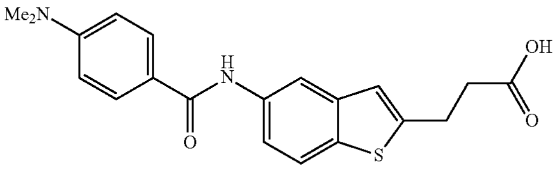 [SMILES: CN(C)c1ccc(C(=O)Nc2ccc3sc(CCC(=O)O)cc3c2)cc1]

This compound was prepared following Representative Procedure for Synthesis of Carboxylic Acids using ethyl 3-(5-(4-(dimethylamino)benzamido)benzo[b]thiophen-2-yl) propanoate (0.207 mmol, 0.082 g) and 1 M sodium hydroxide (0.414 mmol, 0.414 mL), and provided as the hydrochloride salt. Yield: 0.192 g (79%), off-white solid; $^{1}H$ NMR (400 MHz, DMSO-$d_6$) δ 9.92 (s, 1H), 8.22 (d, J=2.0 Hz, 1H), 7.91-7.85 (m, 2H), 7.78 (d, J=8.7 Hz, 1H), 7.61 (dd, J=8.8, 2.1 Hz, 1H), 7.15 (s, 1H), 6.86-6.70 (m, 2H), 3.14-3.02 (m, 2H), 3.01 (s, 6H), 2.67 (t, J=7.3 Hz, 2H). $^{13}C$ NMR (101 MHz, DMSO-$d_6$) δ 173.4, 165.2, 152.4, 145.5, 140.0, 136.6, 133.2, 129.1, 121.9, 121.2, 121.1, 117.7, 114.0, 110.8, 39.8, 35.0, 25.7.

3-(5-(4-Isopropylbenzamido)benzo[b]thiophen-2-yl) propanoic acid (KH-37A)

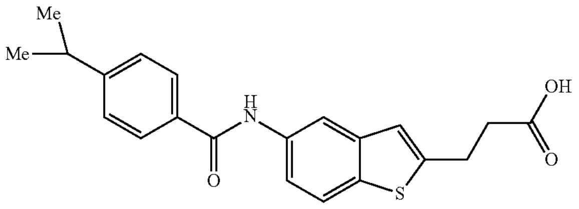 [SMILES: CC(C)c1ccc(C(=O)Nc2ccc3sc(CCC(=O)O)cc3c2)cc1]

This compound was prepared following Representative Procedure for Synthesis of Carboxylic Acids using ethyl 3-(5-(4-isopropylbenzamido)benzo[b]thiophen-2-yl)propanoate (0.212 mmol, 0.084 g) and 1 M sodium hydroxide (0.425 mmol, 0.425 mL). Yield: 0.075 g (96%), off-white solid; $^{1}H$ NMR (400 MHz, DMSO-$d_6$) δ 10.22 (s, 1H), 8.23 (d, J=2.0 Hz, 1H), 7.93-7.86 (m, 2H), 7.81 (d, J=8.7 Hz, 1H), 7.61 (dd, J=8.7, 2.1 Hz, 1H), 7.44-7.33 (m, 2H), 7.17 (d, J=0.9 Hz, 1H), 3.11 (t, J=7.3 Hz, 2H), 2.98 (sep, J=6.7 Hz, 2H), 2.66 (t, J=7.3 Hz, 2H), 1.24 (d, J=6.9 Hz, 6H). $^{13}C$ NMR (101 MHz, DMSO-$d_6$) δ 173.4, 165.2, 152.4, 145.5, 140.0, 136.6, 133.2, 129.1, 121.9, 121.2, 173.3, 165.4, 152.2, 145.6, 140.0, 136.1, 133.7, 132.7, 127.8, 126.3, 122.1, 121.2, 117.6, 114.1, 35.0, 33.4, 25.6, 23.7.

5-(4-(tert-butyl)benzamido)-1H-indole-2-carboxylic acid (KH-39A)

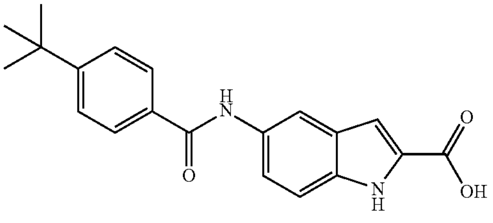 [SMILES: CC(C)(C)c1ccc(C(=O)Nc2ccc3[nH]c(C(=O)O)cc3c2)cc1]

This compound was prepared following Representative Procedure for Synthesis of Carboxylic Acids using ethyl 5-(4-(tert-butyl)benzamido)-1H-indole-2-carboxylate (0.55 mmol, 0.02 g), and 1 M sodium hydroxide (1.1 mmol, 1.1 mL). Yield: 0.11 g (57%), off-white solid; $^{1}H$ NMR (400 MHz, DMSO-$d_6$) δ 12.93 (brs, 1H), 11.72 (s, 1H), 10.09 (s, 1H), 8.13 (m, 1H), 7.91 (d, J=8.8 Hz, 2H), 7.54 (m, 3H), 7.40 (d, J=8.9 Hz, 1H), 7.08 (s, 1H), 1.38 (s, 9H).

5-(4-(tert-butyl)benzamido)benzo[b]thiophene-2-carboxylic acid (KH-43A)

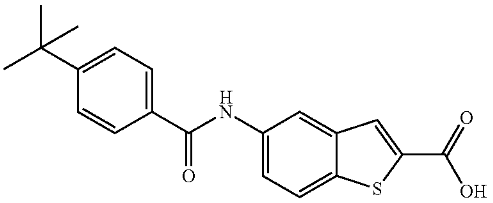 [SMILES: CC(C)(C)c1ccc(C(=O)Nc2ccc3sc(C(=O)O)cc3c2)cc1]

This compound was prepared following Representative Procedure for Synthesis of Carboxylic Acids using methyl 5-(4-(tert-butyl)benzamido)benzo[b]thiophene-2-carboxylate (200 mg). Yield: 90% (173 mg). Beige solid. IR 3300 (broad peak), 2961, 1683, 1651 $cm^{-1}$; $^{1}H$ NMR (400 MHz, DMSO-$d_6$) δ 13.44 (br. s, 1H), 10.35 (s, 1H), 8.51 (s, 1H), 8.10 (s, 1H), 8.00 (d, J=8.8 Hz, 1H), 7.96-7.89 (complex, 2H), 7.81 (dd, J=8.8, 2.1 Hz, 1H), 7.56 (d, J=8.4 Hz, 2H), 1.33 (s, 9H) ppm; $^{13}C$ NMR (100 MHz, DMSO-$d_6$) δ 167.0, 165.3, 152.4, 139.7, 139.6, 137.34, 137.27, 134.0, 129.5, 129.2, 122.5, 120.9, 120.4, 119.9, 115.0, 110.8, 39.8 ppm; HRMS (ESI): Calcd. for $C_{20}H_{19}N_2O_3S$ $(M+H)^+$: 367.1116; found 367.1115.

(E)-3-(5-(cyclohexanecarboxamido)benzo[b]thiophen-2-yl)acrylic acid (KH-46A)

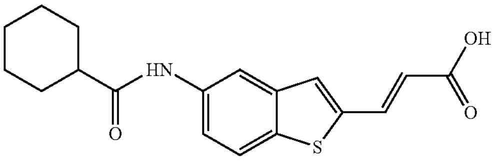 [SMILES: O=C(O)/C=C/c1cc2cc(NC(=O)C3CCCCC3)ccc2s1]

This compound was prepared following Representative Procedure for Synthesis of Carboxylic Acids using ethyl (E)-3-(5-(cyclohexanecarboxamido) benzo[b]thiophen-2-yl)acrylate. $^1$H NMR (400 MHz, $CD_3OD$) δ 8.12 (d, J=1.9 Hz, 1H), 7.81 (d, J=15.6 Hz, 1H), 7.67 (d, J=8.6 Hz, 1H), 7.45-7.40 (complex, 2H), 6.22 (d, J=15.6 Hz, 1H), 2.37-2.26 (m, 1H), 1.93-1.77 (m, 4H), 1.72-1.65 (m, 1H), 1.58-1.45 (m, 2H), 1.37-1.20 (m, 3H), N—H not captured; $^{13}$C NMR (101 MHz, $CD_3OD$) δ 177.5, 169.5, 141.2, 141.0, 138.9, 137.0, 136.5, 129.6, 123.2, 120.8, 120.3, 116.1, 46.9, 30.4, 26.52, 26.46.

(E)-3-(5-(picolinamido)benzo[b]thiophen-2-yl) acrylic acid hydrochloride (KH-47A)

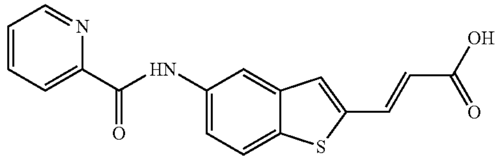 [SMILES: O=C(O)/C=C/c1cc2cc(NC(=O)c3ccccn3)ccc2s1]

This compound was prepared following Representative Procedure for Synthesis of Carboxylic Acids using ethyl (E)-3-(5-(picolinamido)benzo[b]thiophen-2-yl)acrylate to provide the title compound as the hydrochloride salt. $^1$H NMR (400 MHz, DMSO-$d_6$) δ 10.81 (s, 1H), 8.76 (d, J=4.4 Hz, 1H), 8.55-8.53 (m, 1H), 8.19 (d, J=7.8 Hz, 1H), 8.09 (td, J=7.7, 0.9 Hz, 1H), 7.97-7.80 (m, 4H), 7.70 (s, 1H), 6.24 (d, J=15.7 Hz, 1H); $^{13}$C NMR (101 MHz, DMSO-$d_6$) δ 167.0, 162.6, 149.85, 148.5, 140.0, 139.7, 138.2, 137.0, 135.92, 134.8, 129.3, 127.0, 122.8, 122.4, 120.5, 120.2, 115.1.

5-(picolinamido)-1H-indole-2-carboxylic acid hydrochloride (KH-56A)

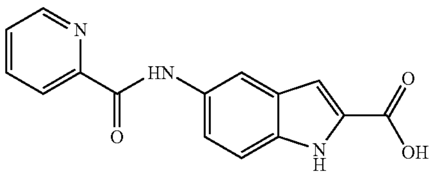 [SMILES: O=C(Nc1ccc2[nH]c(C(=O)O)cc2c1)c1ccccn1]

This compound was prepared following Representative Procedure for Synthesis of Carboxylic Acids using ethyl 5-(picolinamido)-1H-indole-2-carboxylate (100 mg) to provide the title compound as the hydrochloride salt. Yield: 90% (82 mg). Light brown solid. IR 3332 (broad peak), 2917, 1671, 1597 cm$^{-1}$; $^1$H NMR (400 MHz, DMSO-$d_6$) δ 12.91 (s, 1H), 11.73 (s, 1H), 10.51 (s, 1H), 8.74 (d, J=6.2 Hz, 1H), 8.26 (s, 1H), 8.17 (d, J=7.8 Hz, 1H), 8.07 (m, 1H), 7.71-7.63 (complex, 2H), 7.41 (d, J=8.8 Hz, 1H), 7.08 (s, 1H) ppm; $^{13}$C NMR (100 MHz, DMSO-$d_6$) δ 162.7, 162.0, 150.1, 148.3, 138.2, 134.4, 131.2, 129.0, 126.73, 126.65, 122.2, 119.4, 112.7, 112.4, 107.4 ppm; HRMS (ESI): Calcd. for $C_{15}H_{12}N_3O_3$ $(M+H)^+$: 282.0879; found 282.0872.

5-(4-(dimethylamino)benzamido)-1H-indole-2-carboxylic acid (KH-57A)

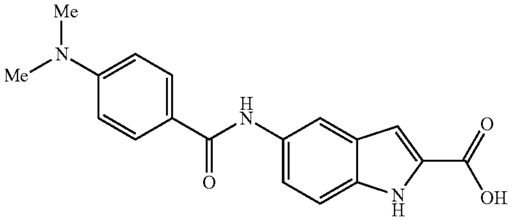 [SMILES: CN(C)c1ccc(C(=O)Nc2ccc3[nH]c(C(=O)O)cc3c2)cc1]

This compound was prepared following Representative Procedure for Synthesis of Carboxylic Acids using ethyl 5-(4-(dimethylamino)benzamido)-1H-indole-2-carboxylate (400 mg), providing the compound as the hydrochloride salt. Yield: 91% (125 mg). Light brown solid. IR 3291 (broad peak), 2959, 1690, 1603 cm$^{-1}$; $^1$H NMR (400 MHz, DMSO-$d_6$) δ 12.84 (br.s, 1H), 11.66 (s, 1H), 9.78 (s, 1H), 8.08 (s, 1H), 7.88 (d, J=8.4 Hz, 2H), 7.53 (d, J=8.9 Hz, 1H), 7.37 (d, J=8.8 Hz, 1H), 7.05 (s, 1H), 6.76 (d, J=8.5 Hz, 2H), 3.00 (s, 6H) ppm; $^{13}$C NMR (100 MHz, DMSO-$d_6$) δ 165.0, 162.8, 152.2, 134.2, 132.4, 129.0, 128.8, 126.7, 121.5, 119.9, 112.9, 112.1, 110.8, 107.3, 39.8 ppm; HRMS (ESI): Calcd. for $C_{18}H_{18}N_3O_3$ $(M+H)^+$: 324.1348; found 324.1342.

5-(4-(Dimethylamino)benzamido)benzo[b]thiophene-2-carboxylic acid (KH-58A)

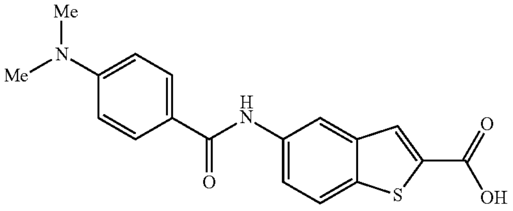 [SMILES: CN(C)c1ccc(C(=O)Nc2ccc3sc(C(=O)O)cc3c2)cc1]

This compound was prepared following Representative Procedure for Synthesis of Carboxylic Acids using methyl 5-(4-(dimethylamino)benzamido)benzo[b]thiophene-2 -carboxylate (400 mg), providing the compound as the hydrochloride salt. Yield: 76% (321 mg). Yellow solid. IR 2919, 1683, 1662 cm$^{-1}$; $^1$H NMR (400 MHz, DMSO-$d_6$) δ 13.41 (br.s, 1H), 10.05 (s, 1H), 8.50 (d, J=2.0 Hz, 1H), 8.08 (s, 1H), 7.97 (d, J=8.8 Hz, 1H), 7.93-7.87 (complex, 2H), 7.82 (dd, J=8.8, 2.1 Hz, 1H), 6.85-6.69 (complex, 2H), 3.01 (s, 6H) ppm; $^{13}$C NMR (100 MHz, DMSO-$d_6$) δ 165.4, 163.7, 152.4, 139.1, 137.2, 136.0, 135.9, 130.1, 129.2, 122.8, 121.3, 120.9, 116.0, 110.8, 39.8 ppm; HRMS (ESI): Calcd. for $C_{18}H_{17}N_2O_3S$ $(M+H)^+$: 341.0960; found 341.0954.

5-(Picolinamido)benzo[b]thiophene-2-carboxylic acid hydrochloride (KH-60A)

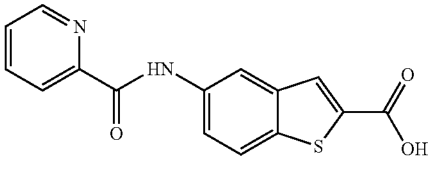 [SMILES: O=C(Nc1ccc2sc(C(=O)O)cc2c1)c1ccccn1]

This compound was prepared following Representative Procedure for Synthesis of Carboxylic Acids using methyl 5-(picolinamido)benzo[b]thiophene-2-carboxylate (400 mg) to provide the title compound as the hydrochloride salt. Yield: 68% (289 mg). Yellow solid. IR 3360 (broad peak), 2915, 1670 $cm^{-1}$; $^1H$ NMR (400 MHz, DMSO-$d_6$) δ 13.42 (br.s, 1H), 10.83 (s, 1H), 8.77 (d, J=4.7 Hz, 1H), 8.67 (s, 1H), 8.19 (d, J=7.8 Hz, 1H), 8.10-8.07 (complex, 2H), 8.02 (d, J=8.8 Hz, 1H), 7.95 (d, J=8.6 Hz, 1H), 7.70 (m, 1H) ppm; $^{13}C$ NMR (100 MHz, DMSO-$d_6$) δ 164.0, 162.6, 149.9, 148.5, 139.8, 139.4, 138.2, 136.7, 135.6, 128.4, 127.0, 123.0, 122.4, 120.4, 115.9 ppm; HRMS (ESI): Calcd. for $C_{15}H_{11}N_2O_3S$ $(M+H)^+$: 299.0490; found 299.0476.

(E)-3-(5-(4-(tert-butyl)benzamido)-1H-indol-2-yl) acrylic acid (KH-48A)

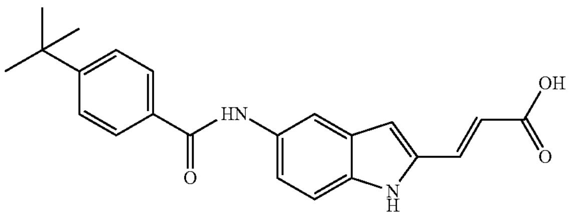 [SMILES: CC(C)(C)c1ccc(C(=O)Nc2ccc3[nH]c(/C=C/C(=O)O)cc3c2)cc1]

Ethyl (E)-3-(5-(4-(tert-butyl)benzamido)-1H-indol-2-yl) acrylate (0.39 g, 1 mmol) was added in a mixture of 2N LiOH solution (10 mL) and THE (10 mL) (ratio volume, 1:1) and the reaction was refluxed (40° C.) for 12 h. Upon completion, the reaction mixture was adjusted the pH=3 with 2N HCl. The reaction was then extracted with ethyl acetate (3*20 mL). The combined organic layers were washed by saturated $K_2CO_3$ solution, dried ($MgSO_4$), filtered, concentrated and purified by silica gel column chromatography ($CH_2Cl_2$: MeOH=25:1) to obtain the compound as a yellow solid (0.336 g, 92.8%). $^1H$ NMR (400 MHz, DMSO-$d_6$) δ 12.33 (s, 1H), 11.53 (d, 1H), 10.08 (s, 1H), 8.04 (d, 1H), 7.93 (m, 2H), 7.58 (m, 4H), 7.36 (d, 1H), 6.87 (d, 1H), 6.48 (d, 1H), 1.34 (d, 9H).

(E)-3-(5-(4-(dimethylamino)benzamido)-1H-indol-2-yl)acrylic acid (KH-52A)

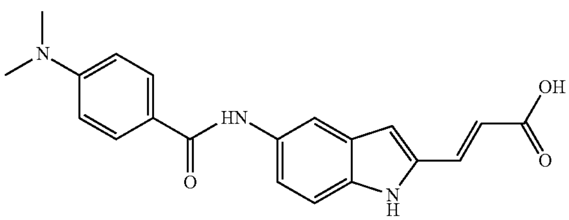 [SMILES: CN(C)c1ccc(C(=O)Nc2ccc3[nH]c(/C=C/C(=O)O)cc3c2)cc1]

This compound was prepared similar to the synthesis of KH-48A, but using Ethyl (E)-3-(5-(4-(dimethylamino)benzamido)-1H-indol-2-yl)acrylate (0.377 g, 1 mmol), 2N LiOH solution (10 mL) and THE (10 mL). Yield: 0.33 g (94.5%), yellow solid $^1H$ NMR (400 MHz, DMSO-$d_6$) δ 12.40 (br, 1H), 11.48 (s, 1H), 9.56 (s, 1H), 7.51 (m, 3H), 7.23 (m, 2H), 6.96 (d, 1H), 6.76 (s, 1H), 6.67 (d, 2H), 6.44 (d, 1H), 2.93 (s, 6H).

Representative Procedure for Synthesis of Hydroxamic Acids:

To the appropriate carboxylic acids, e.g., provided above, (0.047 mmol) in THE (0.5 mL) was added isobutyl chloroformate (0.094 mmol, 0.012 mL, 2 eq.) and N-methylmorpholine (0.094 mmol, 0.0103 mL, 2 eq.) at room temperature and the reaction was run for 1 h. Upon the formation of the activated anhydride, the reaction mixture was filtered first through a fritted filter followed by a syringe filter. Note, for small scale reactions (less than 0.1 mmol), filtration through syringe filter would suffice. 2×1 mL of THF was used for rinsing purpose. In a separate 2-dram vial containing a solution of hydroxylamine (50% in water, 0.469 mmol, 0.029 mL, 10 eq.) in THE (0.1 mL) was added the filtrate at room temperature and stirred for 18 h. Upon completion, solvents were removed in vacuo and the residue was dissolved in EtOAc (2 mL) and washed with saturated solution of $NH_4Cl$ or 1 N HCl. The aqueous layer was extracted with EtOAc (2 mL×3). The combined layer was washed with brine, dried over anhydrous $Na_2SO_4$, and concentrated in vacuo. The residue was purified via reverse phase chromatography (using water and acetonitrile, 0 to 100% gradient) to isolate the corresponding hydroxamic acids.

4-(tert-Butyl)-N-(2-(3-(hydroxyamino)-3-oxopropyl) benzo[b]thiophen-5-yl)benzamide (KH-22)

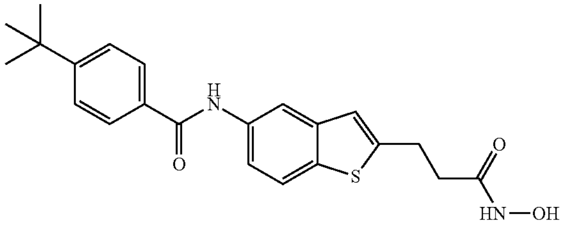 [SMILES: CC(C)(C)c1ccc(C(=O)Nc2ccc3sc(CCC(=O)NO)cc3c2)cc1]

This compound was prepared following Representative Procedure for Synthesis of Hydroxamic Acids using 3-(5-(4-(tert-butyl)benzamido)benzo[b]thiophen-2-yl)propanoic acid (0.102 mmol, 0.039 g), isobutyl chloroformate (0.204 mmol, 0.027 mL), N-methylmorpholine (0.204 mmol, 0.022 mL), and hydroxylamine (1.022 mmol, 0.063 mL). Yield: 20 mg (49%), off-white solid; $^1H$ NMR (400 MHz, DMSO-$d_6$) δ 10.47 (s, 1H), 10.23 (s, 1H), 8.78 (s, 1H), 8.24 (d, J=1.9 Hz, 1H), 7.93-7.88 (m, 2H), 7.81 (d, J=8.7 Hz, 1H), 7.61 (dd, J=8.7, 2.0 Hz, 1H), 7.57-7.51 (m, 2H), 7.15 (s, 1H), 3.12 (t, J=7.3 Hz, 2H), 2.40 (t, J=7.4 Hz, 2H), 1.33 (s, 9H). $^{13}C$ NMR (101 MHz, DMSO-$d_6$) δ 167.6, 165.5, 154.3, 145.6, 140.0, 136.1, 133.7, 132.3, 127.5, 125.1, 122.1, 121.2, 117.6, 114.1, 40.2, 39.9, 39.7, 39.5, 39.3, 39.1, 38.9, 34.7, 33.4, 30.6, 25.9.

3-(tert-Butyl)-N-(2-(3-(hydroxyamino)-3-oxopropyl) benzo[b]thiophen-5-yl)benzamide (KH-30)

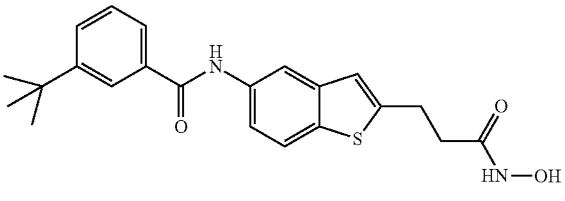 [SMILES: CC(C)(C)c1cccc(C(=O)Nc2ccc3sc(CCC(=O)NO)cc3c2)c1]

This compound was prepared following Representative Procedure for Synthesis of Hydroxamic Acids using 3-(5-(3-(tert-butyl)benzamido)benzo[b]thiophen-2-yl)propanoic acid (0.100 mmol, 0.038 g), isobutyl chloroformate (0.199 mmol, 0.026 mL), N-methylmorpholine (0.199 mmol, 0.022 mL), and hydroxylamine (0.996 mmol, 0.061 mL). Yield: 34 mg (84%), off-white solid; $^1$H NMR (400 MHz, DMSO-$d_6$) δ 10.48 (s, 1H), 10.28 (s, 1H), 8.78 (s, 1H), 8.22 (d, J=2.0 Hz, 1H), 7.96 (t, J=1.7 Hz, 1H), 7.83 (d, J=8.7 Hz, 1H), 7.81-7.77 (m, 1H), 7.65-7.56 (m, 2H), 7.46 (t, J=7.8 Hz, 1H), 7.16 (s, 1H), 3.13 (t, J=7.3 Hz, 2H), 2.41 (t, J=7.4 Hz, 2H), 1.35 (s, 9H). $^{13}$C NMR (101 MHz, DMSO-$d_6$) δ 167.6, 165.9, 150.9, 145.7, 140.0, 136.0, 134.8, 133.8, 128.5, 128.1, 124.8, 124.3, 122.1, 121.2, 117.9, 114.4, 34.6, 33.4, 31.1, 25.9.

N-(2-(3-(hydroxyamino)-3-oxopropyl)benzo[b]thiophen-5-yl)-4-(trifluoromethyl)benzamide (KH-29)

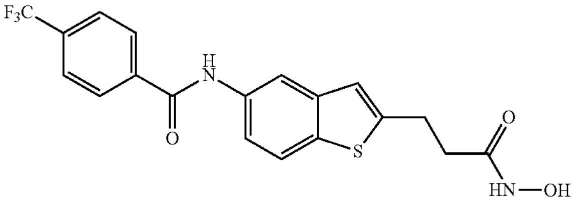

This compound was prepared following Representative Procedure for Synthesis of Hydroxamic Acids using 3-(5-(4-(trifluoromethyl)benzamido)benzo[b]thiophen-2-yl)propanoic acid (0.107 mmol, 0.042 g), isobutyl chloroformate (0.214 mmol, 0.028 mL), N-methylmorpholine (0.214 mmol, 0.023 mL) and hydroxylamine (1.068 mmol, 0.065 mL). Yield: 20 mg (46%), off-white solid; $^1$H NMR (400 MHz, DMSO-$d_6$) δ 10.53 (s, 1H), 10.48 (d, J=1.7 Hz, 1H), 8.78 (d, J=1.7 Hz, 1H), 8.25 (d, J=2.0 Hz, 1H), 8.20-8.13 (m, 2H), 7.97-7.89 (m, 2H), 7.85 (d, J=8.6 Hz, 1H), 7.61 (dd, J=8.7, 2.1 Hz, 1H), 7.17 (s, 1H), 3.13 (t, J=7.3 Hz, 2H), 2.41 (t, J=7.4 Hz, 2H).

N-(2-(3-(hydroxyamino)-3-oxopropyl)benzo[b]thiophen-5-yl)-4-methylbenzamide (KH-27)

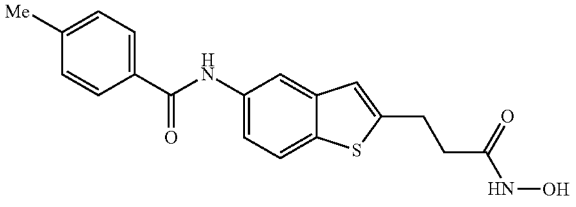 [SMILES: Cc1ccc(C(=O)Nc2ccc3sc(CCC(=O)NO)cc3c2)cc1]

This compound was prepared following Representative Procedure for Synthesis of Hydroxamic Acids using 3-(5-(4-methylbenzamido)benzo[b]thiophen-2-yl)propanoic acid (0.112 mmol, 0.038 g), isobutyl chloroformate (0.224 mmol, 0.029 mL), N-methylmorpholine (0.224 mmol, 0.025 mL) and hydroxylamine (1.120 mmol, 0.069 mL). Yield: 30 mg (76%), off-white solid; $^1$H NMR (400 MHz, DMSO-$d_6$) δ 10.47 (s, 1H), 10.21 (s, 1H), 8.77 (s, 1H), 8.24 (d, J=2.0 Hz, 1H), 7.94-7.85 (m, 2H), 7.81 (d, J=8.6 Hz, 1H), 7.61 (dd, J=8.7, 2.1 Hz, 1H), 7.38-7.28 (m, 2H), 7.15 (s, 1H), 3.12 (t, J=7.2 Hz, 2H), 2.40 (d, J=3.6 Hz, 5H). $^{13}$C NMR (101 MHz, DMSO-$d_6$) δ 168.1, 165.8, 146.1, 141.9, 140.5, 136.5, 134.1, 132.6, 129.3, 128.1, 122.5, 121.7, 118.1, 114.6, 33.8, 26.4, 21.5.

(E)-3-(tert-Butyl)-N-(2-(3-(hydroxyamino)-3-oxoprop-1-en-1-yl)benzo[b]thiophen-5-yl)benzamide (KH-31)

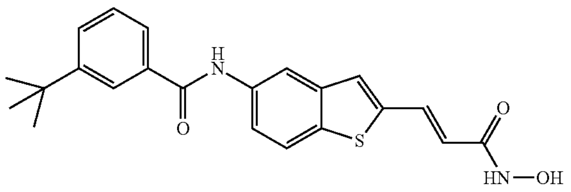 [SMILES: CC(C)(C)c1cccc(C(=O)Nc2ccc3sc(/C=C/C(=O)NO)cc3c2)c1]

This compound was prepared following Representative Procedure for Synthesis of Hydroxamic Acids using (E)-3-(5-(3-(tert-butyl)benzamido)benzo[b]thiophen-2-yl)acrylic acid (0.082 mmol, 0.031 g), isobutyl chloroformate (0.163 mmol, 0.021 mL), N-methylmorpholine (0.163 mmol, 0.018 mL), and hydroxylamine (0.817 mmol, 0.050 mL). Yield: 22 mg (68%), off-white solid; $^1$H NMR (400 MHz, DMSO-$d_6$) δ 10.35 (s, 1H), 8.34 (d, J=2.0 Hz, 1H), 7.95 (t, J=1.9 Hz, 1H), 7.92 (d, J=8.7 Hz, 1H), 7.82-7.76 (m, 1H), 7.75-7.68 (m, 3H), 7.64 (ddd, J=7.9, 2.0, 1.1 Hz, 1H), 7.47 (t, J=7.8 Hz, 1H), 6.29 (d, J=15.6 Hz, 1H), 1.35 (s, 9H). $^{13}$C NMR (101 MHz, DMSO-$d_6$) δ 166.0, 161.9, 150.9, 140.7, 139.8 (2C), 136.6, 134.7, 133.9, 131.9, 128.6, 128.2, 128.0, 124.9, 124.3, 122.6, 120.5, 120.1, 115.3, 34.6, 31.1.

N-(2-(3-(Hydroxyamino)-3-oxopropyl)benzo[b]thiophen-5-yl)-4-(pentafluoro-X$^6$-sulfanyl)benzamide (KH-34)

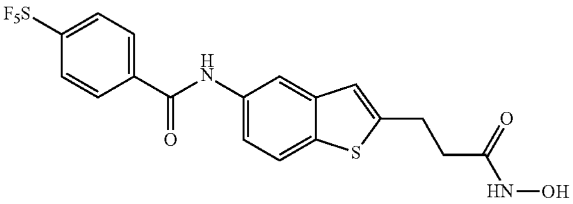

This compound was prepared following Representative Procedure for Synthesis of Hydroxamic Acids using 3-(5-(4-(pentafluoro-λ$^6$-sulfanyl)benzamido)benzo[b]thiophen-2-yl)propanoic acid (0.100 mmol, 0.045 g), isobutyl chloroformate (0.199 mmol, 0.026 mL), N-methylmorpholine (0.199 mmol, 0.022 mL), and hydroxylamine (0.997 mmol, 0.061 mL). Yield: 35 mg (75%), off-white solid; $^1$H NMR (400 MHz, DMSO-$d_6$) δ 10.56 (s, 1H), 10.47 (s, 1H), 8.78 (s, 1H), 8.24 (d, J=2.0 Hz, 1H), 8.20-8.02 (m, 4H), 7.85 (d, J=8.7 Hz, 1H), 7.60 (dd, J=8.7, 2.1 Hz, 1H), 7.17 (s, 1H), 3.13 (t, J=7.3 Hz, 2H), 2.41 (t, J=7.3 Hz, 2H).

(E)-4-(dimethylamino)-N-(2-(3-(hydroxyamino)-3-oxoprop-1-en-1-yl)benzo[b]thiophen-5-yl)benzamide (KH-36)

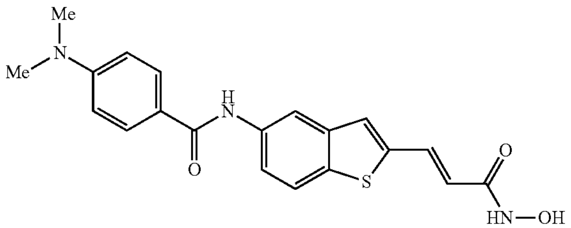 [SMILES: CN(C)c1ccc(C(=O)Nc2ccc3sc(/C=C/C(=O)NO)cc3c2)cc1]

To a solution of (E)-3-(5-(4-(dimethylamino)benzamido)benzo[b]thiophen-2-yl)acrylic acid hydrochloride (90 mg, 1.0 equiv) and O-tritylhydroxylamine (1.1 equivl) in DMF was added HATU (1.1 equivl), and N,N-Diisopropylethylamine (3 equiv). The reaction was stirred at room temperature for 5 h then poured over crushed ice to provide a solid that was filtered, washed with water, and dried under vacuum. The solid obtained (1 equiv) was dissolved in DCM. Trifluoroacetic acid (1.6 equiv) was added followed by triethylsilane (5.3 equiv). The reaction was stirred at room temperature for 6 h. The solvent was removed and the reaction mixture was washed with hexanes first. Then diethyl ether was added and triturated, filtered, washed with ether, and then dried. Yield: 40% (34 mg). Pale yellow solid. IR: 3276 (broad peak), 1699, 1683, 1668, 1652 $cm^{-1}$; $^{1}H$ NMR (400 MHz, DMSO-$d_6$) δ 10.81 (s, 1H), 9.99 (s, 1H), 9.12 (br. s, 1H), 8.35 (d, J=2.0 Hz, 1H), 7.90-7.86 (complex, 3H), 7.77-7.65 (complex, 3H), 6.79-6.76 (complex, 2H), 6.27 (d, J=15.4 Hz, 1H), 3.01 (s, 6H) ppm; $^{13}C$ NMR (100 MHz, DMSO-$d_6$) δ 165.5, 162.2, 152.5, 140.6, 140.0, 137.2, 133.4, 132.1, 129.3, 128.2, 122.6, 121.0, 120.4, 120.1, 115.0, 110.9, 39.8 ppm; HRMS (ESI): Calcd. for $C_{20}H_{20}N_3O_3S$ $(M+H)^+$: 382.1225; found 382.1222.

5-(4-(tert-butyl)benzamido)-N-hydroxy-1H-indole-2-carboxamide (KH-39)

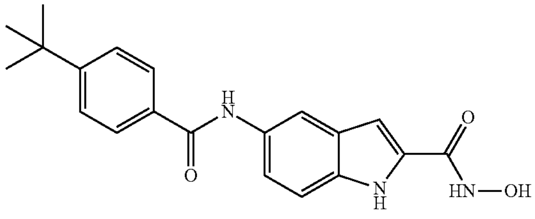 [SMILES: CC(C)(C)c1ccc(C(=O)Nc2ccc3[nH]c(C(=O)NO)cc3c2)cc1]

This compound was prepared following Representative Procedure for Synthesis of Hydroxamic Acids using 5-(4-(tert-butyl)benzamido)-1H-indole-2-carboxylic acid (45 mg). Yield: 43% (20 mg). White solid. IR 3360 (broad peak), 2959, 1641, 1622, 1610 $cm^{-1}$; $^{1}H$ NMR (400 MHz, DMSO-$d_6$) δ 11.60 (s, 1H), 11.23 (s, 1H), 10.06 (s, 1H), 9.12 (s, 1H), 8.08 (s, 1H), 7.91 (d, J=8.1 Hz, 2H), 7.53 (d, J=8.2 Hz, 2H), 7.47 (dd, J=8.8, 2.0 Hz, 1H), 7.38 (d, J=8.8 Hz, 1H), 6.98 (s, 1H), 1.32 (s, 9H) ppm; $^{13}C$ NMR (100 MHz, DMSO) δ 165.1, 159.6, 154.0, 133.4, 132.6, 131.8, 130.7, 127.4, 126.9, 125.1, 118.3, 112.6, 111.9, 101.5, 34.6, 31.0 ppm; HRMS (ESI): Calcd. for $C_{20}H_{22}N_3O_3$ $(M+H)^+$: 352.1661; found 352.1655.

5-(4-(tert-butyl)benzamido)-N-hydroxybenzo[b]thiophene-2-carboxamide (KH-43)

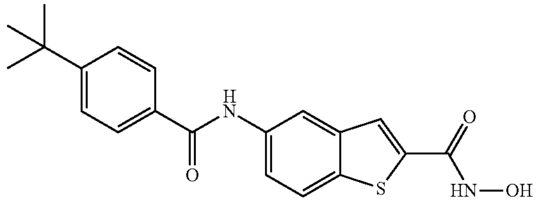 [SMILES: CC(C)(C)c1ccc(C(=O)Nc2ccc3sc(C(=O)NO)cc3c2)cc1]

This compound was prepared following Representative Procedure for Synthesis of Hydroxamic Acids using 5-(4-(tert-butyl)benzamido)benzo[b]thiophene-2-carboxylic acid (25 mg). Yield: 34% (17 mg). Yellow solid. IR 3387 (broad peak), 1646 $cm^{-1}$; $^{1}H$ NMR (400 MHz, DMSO-$d_6$) δ 11.46 (s, 1H), 10.33 (s, 1H), 9.27 (s, 1H), 8.45 (d, J=2.0 Hz, 1H), 7.98-7.91 (complex, 4H), 7.76 (dd, J=8.7, 2.0 Hz, 1H), 7.56 (d, J=8.2 Hz, 2H), 1.33 (s, 9H) ppm; $^{13}C$ NMR (100 MHz, DMSO-$d_6$) δ 165.6, 159.6, 154.5, 139.3, 138.2, 136.7, 134.9, 132.1, 127.5, 125.2, 124.2, 122.7, 120.1, 115.4, 34.7, 30.9 ppm; HRMS (ESI-TOF) m/z: $[M+H]^+$ calcd for $C_{20}H_{21}N_2O_3S$, 369.1273; found 369.1273.

(E)-N-(2-(3-(hydroxyamino)-3-oxoprop-1-en-1-yl)benzo[b]thiophen-5-yl) cyclohexanecarboxamide (KH-46)

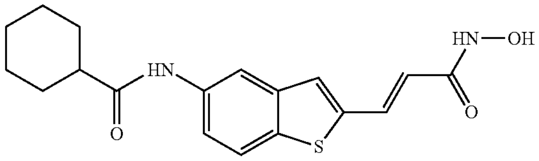 [SMILES: O=C(/C=C/c1cc2cc(NC(=O)C3CCCCC3)ccc2s1)NO]

This compound was prepared following Representative Procedure for Synthesis of Hydroxamic Acids using (E)-3-(5-(cyclohexanecarboxamido)benzo[b]thiophen-2-yl) acrylic acid. $^{1}H$ NMR (400 MHz, DMSO-$d_6$) δ 9.93 (s, 1H), 8.22 (s, 1H), 7.82 (d, J=8.3 Hz, 1H), 7.72-7.61 (m, 2H), 7.54-7.46 (m, 1H), 6.25 (d, J=15.6 Hz, 1H), 2.41-2.29 (m, 1H), 1.87-1.72 (m, 4H), 1.70-1.60 (m, 1H), 1.50-1.35 (m, 2H), 1.34-1.13 (m, 3H); $^{13}C$ NMR (100 MHz, DMSO-$d_6$) δ 174.4, 162.1, 140.7, 139.9, 136.9, 133.0, 131.3, 127.7, 122.6, 120.8, 118.7, 113.6, 44.9, 29.2, 25.4, 25.2.

(E)-N-(2-(3-(hydroxyamino)-3-oxoprop-1-en-1-yl)benzo[b]thiophen-5-yl) picolinamide hydrochloride (KH-47)

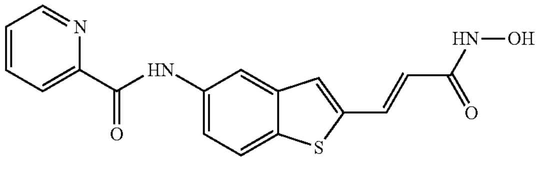 [SMILES: O=C(/C=C/c1cc2cc(NC(=O)c3ccccn3)ccc2s1)NO]

This compound was prepared similarly to the synthesis of KH-36 using (E)-3-(5-(picolinamido)benzo[b]thiophen-2-yl)acrylic acid hydrochloride to provide the title compound as the hydrochloride salt. $^1H$ NMR (400 MHz, DMSO-$d_6$) δ 10.79 (s, 1H), 8.76 (d, J=4.4 Hz, 1H), 8.52-8.48 (m, 1H), 8.19 (d, J=7.8 Hz, 1H), 8.09 (td, J=7.7, 1.6 Hz, 1H), 7.96-7.85 (m, 2H), 7.77-7.66 (m, 3H), 6.29 (d, J=15.6 Hz, 1H).

(E)-4-(tert-butyl)-N-(2-(3-(hydroxyamino)-3-oxoprop-1-en-1-yl)-1H-indol-5-yl)benzamide (KH-48)

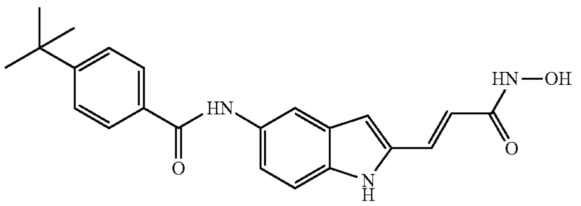 [SMILES: CC(C)(C)c1ccc(C(=O)Nc2ccc3[nH]c(/C=C/C(=O)NO)cc3c2)cc1]

CDI (0.144 g, 0.75 mmol, 1.5 eq) was added to a solution of (E)-3-(5-(4-(tert-butyl) benzamido)-1H-indol-2-yl) acrylic acid (KH-48A) (0.181 g, 0.5 mmol) in dry tetrahydrofuran (THF) (5 ml). The reaction mixture was stirred for 1 h. Powdered hydroxylamine hydrochloride (0.209 mg, 3 mmol) was added. The resulting mixture was stirred overnight (ca. 16 h). The mixture was diluted with 5% aq. $KHSO_4$ (10 ml) and extracted with EtOAc (2×30 mL). The combined organic phase was washed with brine (30 ml) and dried over $Na_2SO_4$. The extract was filtered and concentrated in vacuo to give the crude product, which was purified by silica gel chromatography ($CH_2Cl_2$:MeOH=25:1-10:1), yellow solid (17 mg, 9.44%). $^1H$ NMR (400 MHz, DMSO-$d_6$) δ 10.87 (s, 1H), 10.48 (s, 1H), 10.08 (s, 1H), 9.96 (s, 1H), 8.76 (s, 1H), 7.91 (m, 4H), 7.55 (m, 3H), 7.33 (dd, 1H), 7.24 (d, 1H), 6.13 (s, 1H), 1.34 (s, 9H).

(E)-4-(dimethylamino)-N-(2-(3-(hydroxyamino)-3-oxoprop-1-en-1-yl)-1H-indol-5-yl)benzamide (KH-52)

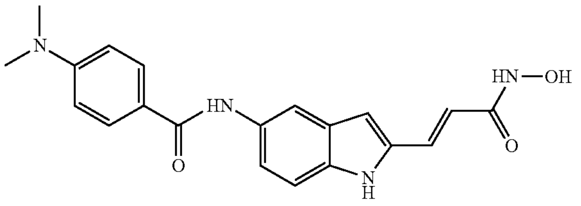 [SMILES: CN(C)c1ccc(C(=O)Nc2ccc3[nH]c(/C=C/C(=O)NO)cc3c2)cc1]

This compound was prepared similar to the synthesis of KH-48, but using (E)-3-(5-(4-(dimethylamino)benzamido)-1H-indol-2-yl)acrylic acid (0.175 g, 0.5 mmol), CDI (0.144 g, 0.75 mmol, 1.5 eq), hydroxylamine hydrochloride (0.209 mg, 3 mmol) and dry tetrahydrofuran (THF) (5 mL). Yield: 19 mg (10.4%), yellow solid $^1H$ NMR (400 MHz, DMSO-$d_6$) δ11.43 (s, 1H), 10.32 (s, 2H), 7.96 (s, 1H), 7.81 (s, 1H), 7.52 (m, 2H), 7.21 (m, 2H), 6.92 (d, 1H), 6.80 (d, 1H), 6.67 (d, 2H), 6.38 (m, 1H), 2.95 (s, 6H).

N-hydroxy-5-(picolinamido)-1H-indole-2-carboxamide hydrochloride (KH-56)

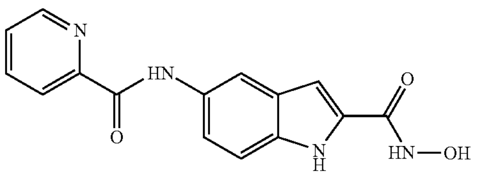 [SMILES: O=C(Nc1ccc2[nH]c(C(=O)NO)cc2c1)c1ccccn1]

To a solution of ethyl 5-(picolinamido)-1H-indole-2-carboxylate (100 mg, 1.0 equiv) in THF/ethanol/water (3:2:1 ratio), NaOH (3.0 equiv) was added and heated at 60° C. overnight. THE and ethanol was removed and the crude was acidified with 1N HCl and dissolved in minimal amount of DMSO. This product was further purified by reverse phase MPLC using a gradient of water and acetonitrile to provide the compound as the hydrochloride salt. Yield: 74% (80 mg). Beige solid. IR 3235 (broad peak), 1653, 1635 $cm^{-1}$; 1H NMR (400 MHz, DMSO-$d_6$) δ 11.63 (s, 1H), 11.25 (brs, 1H), 10.48 (s, 1H), 9.14 (brs, 1H), 8.73 (d, J=4.7 Hz, 1H), 8.35-8.12 (complex, 2H), 8.06 (t, J=7.4 Hz, 1H), 7.75-7.57 (complex, 2H), 7.40 (d, J=8.8 Hz, 1H), 6.99 (s, 1H) ppm; $^{13}C$ NMR (100 MHz, DMSO-$d_6$) δ 162.0, 159.5, 150.2, 148.4, 138.1, 133.6, 131.0, 130.3, 126.9, 126.7, 122.2, 118.1, 112.3, 112.2, 101.8 ppm; HRMS (ESI): Calcd. for $C_{15}H_{13}N_4O_3$ $(M+H)^+$: 297.0988; found 297.0981.

5-(4-(dimethylamino)benzamido)-N-hydroxy-1H-indole-2-carboxamide (KH-57)

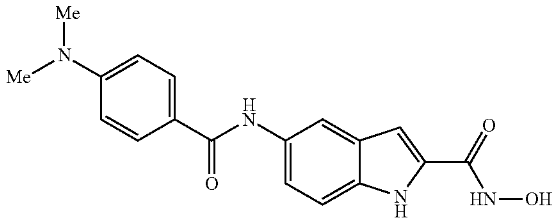 [SMILES: CN(C)c1ccc(C(=O)Nc2ccc3[nH]c(C(=O)NO)cc3c2)cc1]

To a solution of ethyl 5-(4-(dimethylamino)benzamido)-1H-indole-2-carboxylate (67 mg, 1.0 equiv) in THF/ethanol/water (3:2:1 ratio), NaOH (3.0 equiv) was added and heated at 60° C. overnight. THE and ethanol was removed and the crude was acidified with 1N HCl and dissolved in minimal amount of DMSO. This product was further purified by reverse phase MPLC using a gradient of water and acetonitrile to provide the compound as the hydrochloride salt. Yield: 39% (25 mg). Pale brown solid. IR 3400, 2920, 1696, 1668 $cm^{-1}$; $^1H$ NMR (400 MHz, DMSO-$d_6$) δ 11.54 (s, 1H), 11.18 (brs, 1H), 9.74 (s, 1H), 9.08 (brs, 1H), 8.02 (d, J=1.9 Hz, 1H), 7.88 (m, 2H), 7.45 (dd, J=8.8, 2.0 Hz, 1H), 7.34 (d, J=8.8 Hz, 1H), 6.93 (s, 1H), 6.76 (m, 2H), 3.00 (s, 6H) ppm; $^{13}C$ NMR (100 MHz, DMSO-$d_6$) δ 164.9, 159.6, 152.2, 133.2, 132.2, 130.2, 128.9, 126.9, 121.5, 118.6, 112.5, 111.8, 110.8, 109.5, 39.8 ppm; HRMS (ESI): Calcd. for $C_{18}H_{19}N_4O_3$ $(M+H)^+$: 339.1457; found 339.1445.

5-(4-(dimethylamino)benzamido)-N-hydroxybenzo[b]thiophene-2-carboxamide (KH-58)

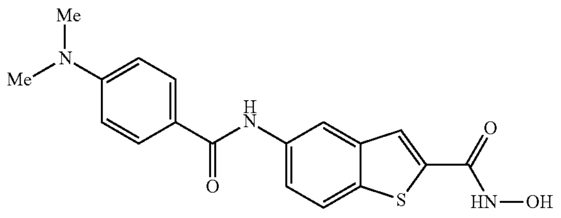 [SMILES: CN(C)c1ccc(C(=O)Nc2ccc3sc(C(=O)NO)cc3c2)cc1]

This compound was prepared following Representative Procedure for Synthesis of Hydroxamic Acids using 5-(4-(dimethylamino)benzamido)benzo[b]thiophene-2-carboxylic acid (100 mg). Yield: 42% (40 mg). Pale brown solid. IR 3300 (broad peak), 1690, 1658 $cm^{-1}$; $^1H$ NMR (400 MHz, DMSO-$d_6$) δ 11.43 (s, 1H), 10.01 (s, 1H), 9.26 (s, 1H), 8.43 (s, 1H), 7.95-7.86 (complex, 4H), 7.77 (m, 1H), 6.78 (d, J=8.6 Hz, 2H), 3.01 (s, 6H) ppm; $^{13}C$ NMR (100 MHz, DMSO-$d_6$) δ 165.3, 159.6, 152.4, 139.4, 138.0, 137.1, 134.4, 129.1, 124.2, 122.6, 120.9, 120.2, 115.3, 110.8 ppm; HRMS (ESI): Calcd. for $C_{18}H_{18}N_3O_3S$ $(M+H)^+$: 356.1069; found 356.1063. Note: in the $^{13}C$ NMR, the signal for the methyl groups of the dimethylamine ($NMe_2$) are subsumed by the signals for the methyl groups of the trace DMSO that is not per-deuterated.

N-(2-(hydroxycarbamoyl)benzo[b]thiophen-5-yl)picolinamide (KH-60)

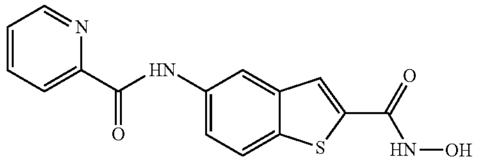 [SMILES: O=C(Nc1ccc2sc(C(=O)NO)cc2c1)c1ccccn1]

This compound was prepared following Representative Procedure for Synthesis of Hydroxamic Acids using 5-(picolinamido)benzo[b]thiophene-2-carboxylic acid (100 mg). Yield: 80% (75 mg). Beige solid. IR 3300 (broad peak), 2920, 1668, 1652 $cm^{-1}$; $^1H$ NMR (400 MHz, DMSO-$d_6$) δ 11.46 (s, 1H), 10.81 (s, 1H), 9.27 (s, 1H), 8.76 (m, 1H), 8.57 (s, 1H), 8.18 (m, 1H), 8.09 (tt, J=7.7, 1.7 Hz, 1H), 7.99 (d, J=8.8 Hz, 1H), 7.92 (dd, J=11.1, 2.1 Hz, 2H), 7.70 (m, 1H) ppm; $^{13}C$ NMR (100 MHz, DMSO-$d_6$) δ 162.7, 159.6 149.8, 148.5, 139.4, 138.4, 138.2, 135.8, 135.3, 127.0, 124.2, 122.9, 122.4, 120.1, 115.5 ppm; HRMS (ESI): Calcd. for $C_{15}H_{12}N_3O_3S$ $(M+H)^+$: 314.0599; found 314.0592.

Representative Procedure for Synthesis of Acyl Hydrazides: To the corresponding carboxylic acids (0.047 mmol, 0.016 g) in THE (0.5 mL) was added isobutyl chloroformate (0.094 mmol, 0.012 mL, 2 eq.) and N-methylmorpholine (0.094 mmol, 0.0103 mL, 2 eq.) at room temperature and the reaction was run for 1 h. Upon the formation of the activated anhydride, the reaction mixture was filtered first through a fritted filter followed by a syringe filter. Note, for small scale reactions (less than 0.1 mmol), filtration through syringe filter would suffice. 2×1 mL of THF was used for rinsing purpose. In a separate 2-dram vial containing a solution of hydrazine (65%, 0.469 mmol, 0.029 mL, 10 eq.) in THE (0.1 mL) was added the filtrate at room temperature and stirred for 18 h. Upon completion, solvents were removed in vacuo and the residue was dissolved in EtOAc (2 mL) and washed with saturated solution of $NH_4Cl$ or 1 N HCl. The aqueous layer was extracted with EtOAc (2 mL×3). The combined layer was washed with brine, dried over anhydrous $Na_2SO_4$, and concentrated in vacuo. The residue was purified via reverse phase chromatography (using water and acetonitrile, 0 to 100% gradient) to isolate the corresponding acyl hydrazides.

4-(tert-butyl)-N-(2-(3-hydrazinyl-3-oxopropyl)benzo[b]thiophen-5-yl)benzamide (KH-22E)

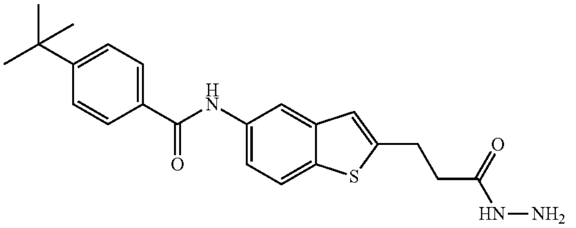 [SMILES: CC(C)(C)c1ccc(C(=O)Nc2ccc3sc(CCC(=O)NN)cc3c2)cc1]

This compound was prepared following Representative Procedure for Synthesis of Acyl Hydrazides using 3-(5-(4-(tert-butyl)benzamido)benzo[b]thiophen-2-yl)propanoic acid (0.152 mmol, 0.058 g), isobutyl chloroformate (0.304 mmol, 0.039 mL), N-methylmorpholine (0.304 mmol, 0.033 mL), and hydrazine (1.520 mmol, 0.048 mL). Yield: 35 mg (58%), off-white solid $^1H$ NMR (400 MHz, DMSO-$d_6$) δ 10.23 (s, 1H), 9.07 (s, 1H), 8.24 (d, J=2.0 Hz, 1H), 7.96-7.85 (m, 2H), 7.81 (d, J=8.6 Hz, 1H), 7.60 (dd, J=8.7, 2.1 Hz, 1H), 7.15 (s, 1H), 4.21 (s, 2H), 3.12 (t, J=7.4 Hz, 2H), 2.47 (t, J=7.5 Hz, 2H), 1.33 (s, 9H). $^{13}C$ NMR (101 MHz, DMSO-$d_6$) δ 170.1, 165.5, 154.3, 145.8, 140.0, 136.1, 133.7, 132.3, 127.5, 125.2, 122.1, 121.1, 117.61, 114.1, 34.7, 34.5, 31.0, 26.1.

4-(tert-butyl)-N-(2-(hydrazinecarbonyl)-1H-indol-5-yl)benzamide (KH-39E)

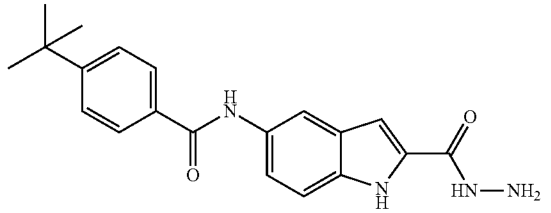 [SMILES: CC(C)(C)c1ccc(C(=O)Nc2ccc3[nH]c(C(=O)NN)cc3c2)cc1]

This compound was prepared following Representative Procedure for Synthesis of Acyl Hydrazides using 5-(4-(tert-butyl)benzamido)-1H-indole-2-carboxylic acid (0.15 mmol, 0.05 g), isobutyl chloroformate (0.30 mmol, 0.04 mL), N-methylmorpholine (0.30 mmol, 0.03 mL), and hydrazine (0.74 mmol, 0.06 mL). Yield: 16 mg (31%), off-white solid; $^1H$ NMR (400 MHz DMSO-$d_6$) δ 11.58 (s, 1H), 10.05 (s, 1H), 9.75 (s, 1H), 8.06 (m, 1H), 7.90 (d, J=8.2 Hz, 2H), 7.54 (d, J=8.3 Hz, 2H), 7.47-7.36 (m, 2H), 7.06 (s, 1H), 3.84 (s, 2H), 1.33 (s, 9H).

HuR Inhibitory Activity Via a Fuorescenese Polarization (FP) Assay

Figure 3:
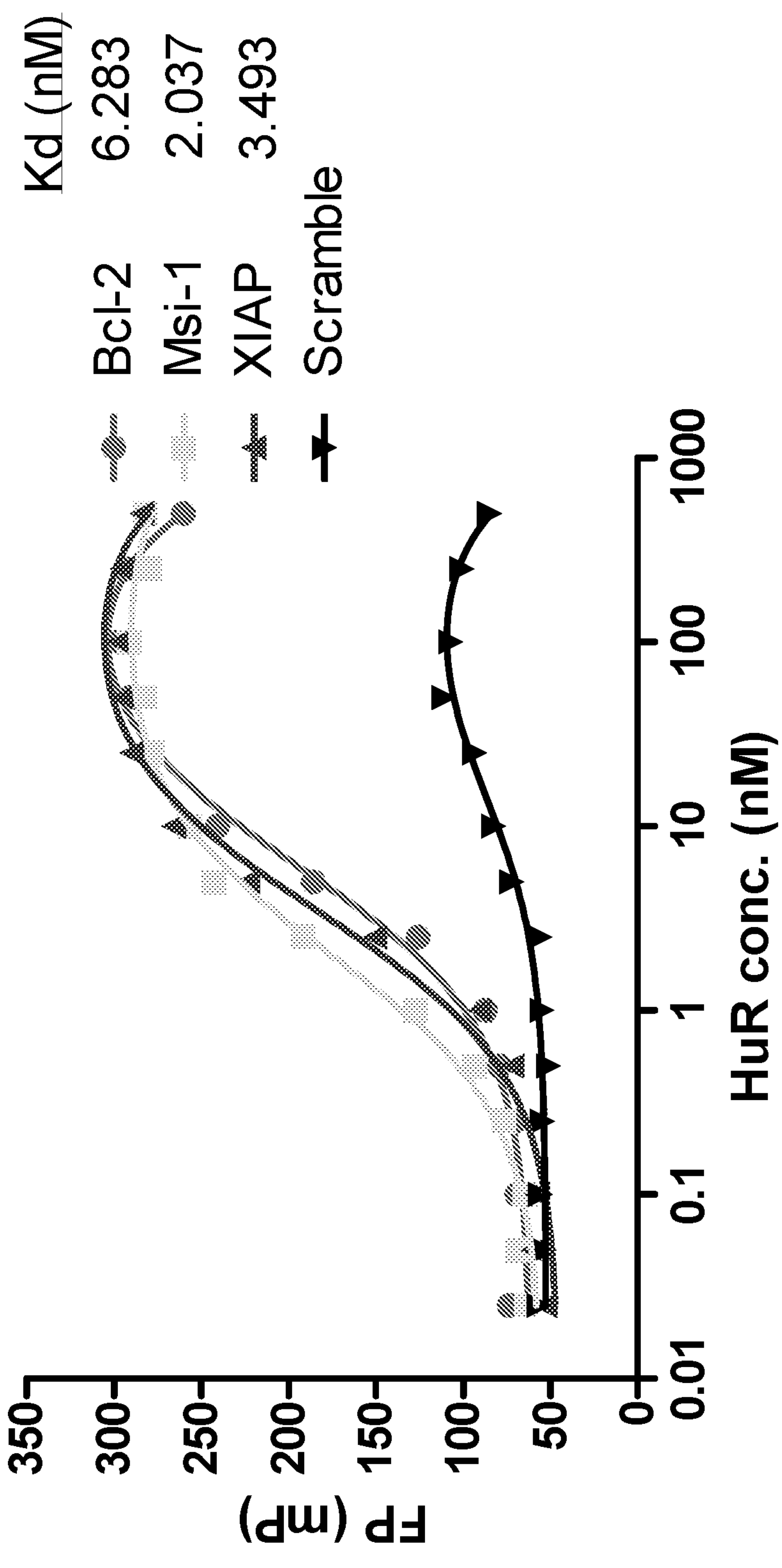
FIG. 3 provides the results of a fluorescence polarization (FP)-based binding assay, illustrating that full length HuR binds to FITC-Bcl-2, Msil, and XIAP RNA but not to scrambled oligo-FITC. The concentration of FITC-RNA used in the assay is 2 nM.

A fluorescence polarization (FP)-based binding assay was utilized to assess the inhibition of HuR protein interaction with the ARE site of Msi1 mRNA ("HuR-Msi1$^{ARE}$") by compounds of interest. Briefly, full-length human HuR protein was produced by the KU COBRE-PSF Protein Purification Group and Bcl2, Msi1 and XIAP mRNA sequences (16 nt) were designed based on literature precedent[23, 24, 31, 32]. Fluorescein labeled RNAs were purchased from Dharmacon with the following sequences: Msi1 RNA: 5'-GCUUUUAUUUAUUUUG-3'-fluorescein; Bcl-2 RNA: 5'-AAAAGAUUUAUUUAUU-3'-fluorescein; XIAP RNA: 5'-UAGUUAUUUUUA UGUC-3'-fluorescein, and a 16-nt degenerative RNA with 3'-fluorescein label was used as a negative control. FIG. 3 provides the results of these experiments, illustrating HuR binding with the above fluorescein-labeled target RNAs, with a Kd of 6.3, 2.0 and 3.5 nM for Bcl2, Msi1 and XIAP RNA oligos, respectively.

With the FP assay of HuR-Msi1ARE binding, the inhibition of the HuR-Msi1ARE interaction by various compounds of the present technology was assessed. Similar FP assays for Musashi 2 (Msi2) and for RNA-binding protein Lin-28 homolog B (LIN28B) were also performed on various compounds of the present technology. The results of such assays for HuR are provided in Table 1 alongside the compound structures as well as ID numbers for ease of reference; the results of such assays for Msi1, Msi2, and LIN28B are provided in Table 2.

The cytotoxicity of various compounds of the present technology in several cancer cell lines (pancreatic cancer cell line MIAPaCa-2, triple-negative breast cancer cell line MDA-MB-231, and colon cancer cell lines HCT116, HCT116 β/W, and RKO) was assessed by a cytotoxicity assay. Cells were seeded in 96-well culture plates (3,000-5,000 cells/well) and treated with titrated compounds in triplicate. After 96 h incubation, cell growth medium was removed and proliferation reagent WST-8 (Sigma) was added to each well and incubated at 37° C. for 1-3 h. Absorbance was then measured with a plate reader at 450 nm with correction at 650 nm. The results were expressed as the percentage of absorbance of treated wells versus that of vehicle control. $IC_{50}$, the drug concentration causing 50% growth inhibition, was calculated via sigmoid curve fitting using GraphPad Prism 5.0. The results for those compounds tested against MIAPaCa-2 and MDA-MB-231 are provided in Table 1; the results for those compounds tested against colon cancer cell lines HCT116, HCT116 β/W, and RKO are provided in Table 3.

TABLE 1

Results of HuR inhibitory activity in FP assay and cytotoxicity assays for compounds of the present technology

| ID | Structure | HuR Ki via FP assay (μM) | Cytotoxicity ($IC_{50}$, μM) MIAPaCa-2 | MDA-MB-231 |
|---|---|---|---|---|
| KH-19 | 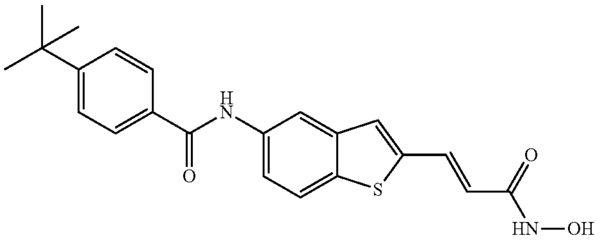 [SMILES: CC(C)(C)c1ccc(C(=O)Nc2ccc3sc(/C=C/C(=O)NO)cc3c2)cc1] | 0.15 | 2.338 | 1.331 |
| KH-20 | 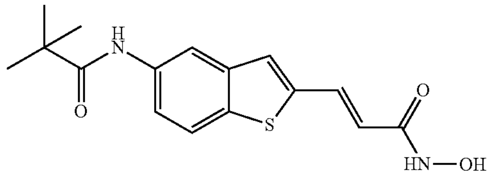 [SMILES: CC(C)(C)C(=O)Nc1ccc2sc(/C=C/C(=O)NO)cc2c1] | >20 | 3.981 | ND |
| KH-22 | 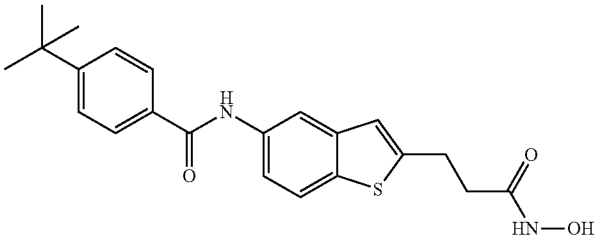 [SMILES: CC(C)(C)c1ccc(C(=O)Nc2ccc3sc(CCC(=O)NO)cc3c2)cc1] | 0.83 | ND | 3.478 |

TABLE 1-continued
Results of HuR inhibitory activity in FP assay and cytotoxicity assays for compounds of the present technology
| ID | Structure | HuR Ki via FP assay (μM) | Cytotoxicity ($IC_{50}$, μM) MIAPaCa-2 | MDA-MB-231 |
|---|---|---|---|---|
| KH-27 | 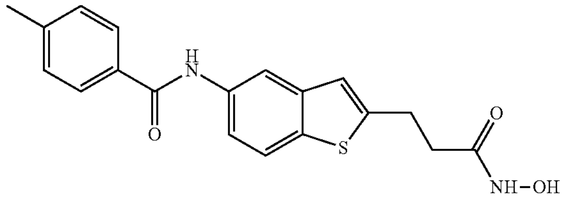 [SMILES: Cc1ccc(C(=O)Nc2ccc3sc(CCC(=O)NO)cc3c2)cc1] | 3.72 | ND | 9.344 |
| KH-29 | 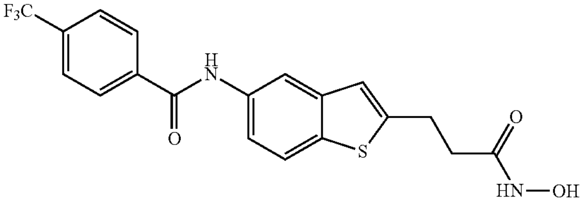 [SMILES: O=C(CCc1cc2cc(NC(=O)c3ccc(C(F)(F)F)cc3)ccc2s1)NO] | 2.51 | ND | 12.36 |
| KH-30 | 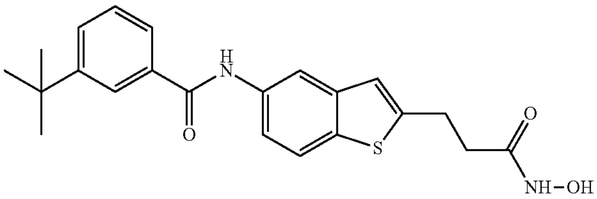 [SMILES: CC(C)(C)c1cccc(C(=O)Nc2ccc3sc(CCC(=O)NO)cc3c2)c1] | 4.98 | ND | 5.511 |
| KH-31 | 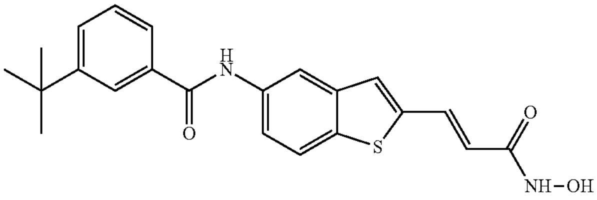 [SMILES: CC(C)(C)c1cccc(C(=O)Nc2ccc3sc(/C=C/C(=O)NO)cc3c2)c1] | 0.47 | ND | 9.741 |
| KH-32 | 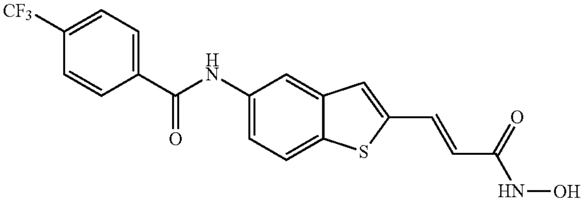 [SMILES: O=C(/C=C/c1cc2cc(NC(=O)c3ccc(C(F)(F)F)cc3)ccc2s1)NO] | 0.51 | ND | 2.618 |
| KH-34 | 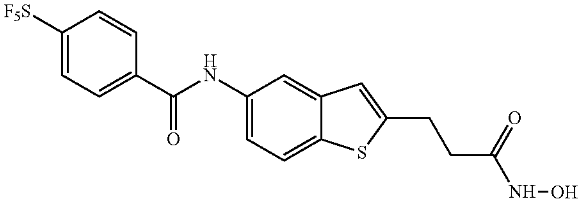 | 1.53 | ND | 3.965 |

TABLE 1-continued
| Results of HuR inhibitory activity in FP assay and cytotoxicity assays for compounds of the present technology | | | | |
|---|---|---|---|---|
| | | HuR Ki | Cytotoxicity ($IC_{50}$, μM) | |
| ID | Structure | via FP assay (μM) | MIAPaCa-2 | MDA-MB-231 |
| KH-36 | 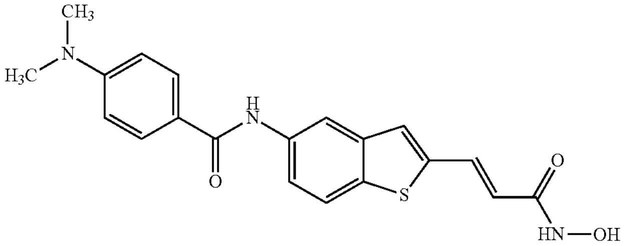 [SMILES: CN(C)c1ccc(C(=O)Nc2ccc3sc(/C=C/C(=O)NO)cc3c2)cc1] | 0.55 | ND | 4.02 |
| KH-38 | 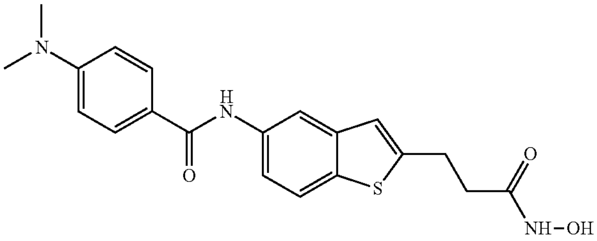 [SMILES: CN(C)c1ccc(C(=O)Nc2ccc3sc(CCC(=O)NO)cc3c2)cc1] | 2.88 | ND | 25.93 |
| KH-39 | 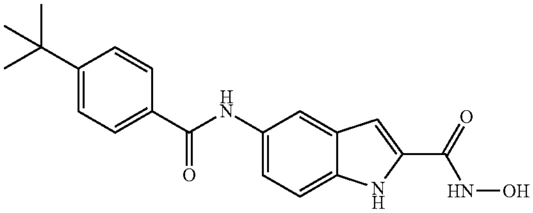 [SMILES: CC(C)(C)c1ccc(C(=O)Nc2ccc3[nH]c(C(=O)NO)cc3c2)cc1] | 0.65 | ND | 4.74 |
| KH-43 | 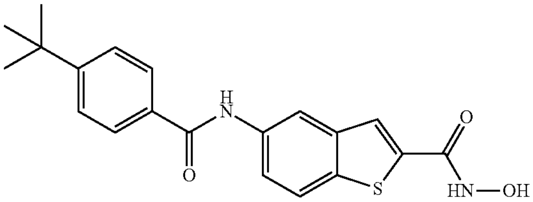 [SMILES: CC(C)(C)c1ccc(C(=O)Nc2ccc3sc(C(=O)NO)cc3c2)cc1] | 0.44 | ND | 3.71 |
| KH-46 | 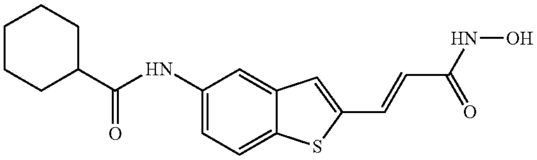 [SMILES: O=C(/C=C/c1cc2cc(NC(=O)C3CCCCC3)ccc2s1)NO] | 1.29 | ND | 3.501 |
| KH-47 | 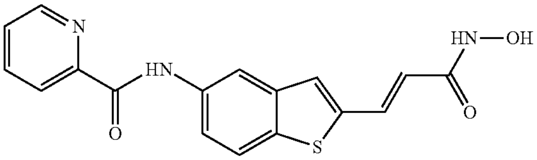 [SMILES: O=C(/C=C/c1cc2cc(NC(=O)c3ccccn3)ccc2s1)NO] | 4.44 | ND | 3.106 |

TABLE 1-continued
Results of HuR inhibitory activity in FP assay and cytotoxicity assays for compounds of the present technology
| ID | Structure | HuR Ki via FP assay (μM) | Cytotoxicity ($IC_{50}$, μM) MIAPaCa-2 | MDA-MB-231 |
|---|---|---|---|---|
| KH-48 | 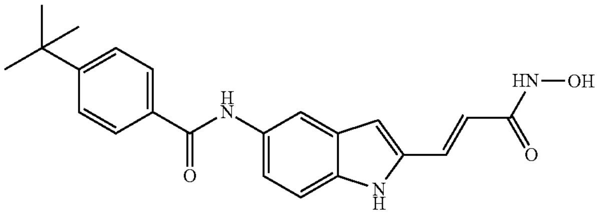 [SMILES: CC(C)(C)c1ccc(C(=O)Nc2ccc3[nH]c(/C=C/C(=O)NO)cc3c2)cc1] | 0.34 | ND | 2.236 |
| KH-52 | 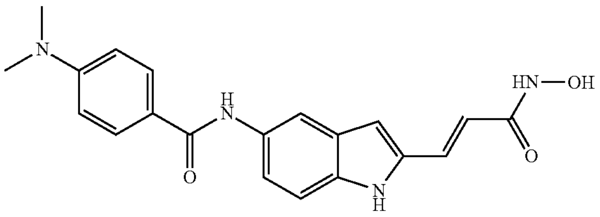 [SMILES: CN(C)c1ccc(C(=O)Nc2ccc3[nH]c(/C=C/C(=O)NO)cc3c2)cc1] | 0.69 | ND | 8.909 |
| KH-56 | 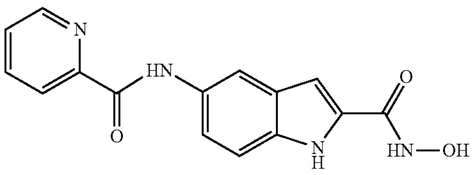 [SMILES: O=C(Nc1ccc2[nH]c(C(=O)NO)cc2c1)c1ccccn1] | >20 | ND | 75.31 |
| KH-57 | 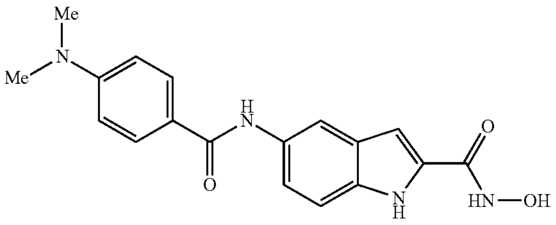 [SMILES: CN(C)c1ccc(C(=O)Nc2ccc3[nH]c(C(=O)NO)cc3c2)cc1] | 3.31 | ND | 11.31 |
| KH-58 | 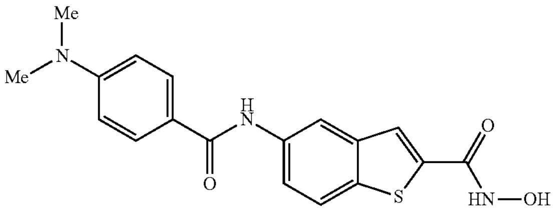 [SMILES: CN(C)c1ccc(C(=O)Nc2ccc3sc(C(=O)NO)cc3c2)cc1] | 0.61 | ND | 1.311 |
| KH-60 | 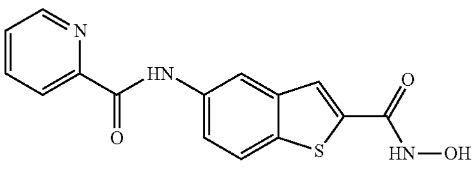 [SMILES: O=C(Nc1ccc2sc(C(=O)NO)cc2c1)c1ccccn1] | 3.23 | ND | 4.428 |

TABLE 1-continued
Results of HuR inhibitory activity in FP assay and cytotoxicity assays for compounds of the present technology
| ID | Structure | HuR Ki via FP assay (μM) | Cytotoxicity ($IC_{50}$, μM) MIAPaCa-2 | Cytotoxicity ($IC_{50}$, μM) MDA-MB-231 |
|---|---|---|---|---|
| KH-19A | 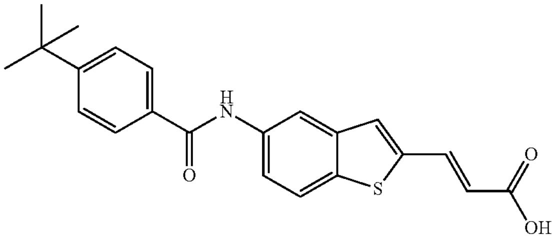 [SMILES: CC(C)(C)c1ccc(C(=O)Nc2ccc3sc(/C=C/C(=O)O)cc3c2)cc1] | 0.97 | 55.97 | 72.13 |
| KH-20A | 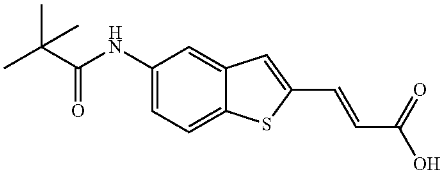 [SMILES: CC(C)(C)C(=O)Nc1ccc2sc(/C=C/C(=O)O)cc2c1] | >20 | >100 | ND |
| KH-22A | 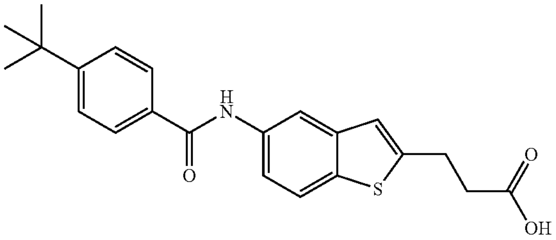 [SMILES: CC(C)(C)c1ccc(C(=O)Nc2ccc3sc(CCC(=O)O)cc3c2)cc1] | 3.83 | ND | 19.76 |
| KH-23A | 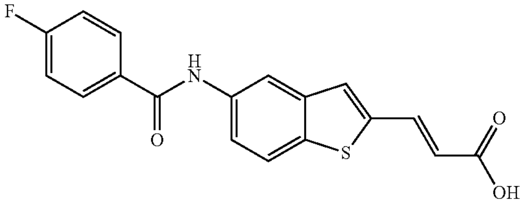 [SMILES: O=C(O)/C=C/c1cc2cc(NC(=O)c3ccc(F)cc3)ccc2s1] | >20 | ND | ND |
| KH-27A | 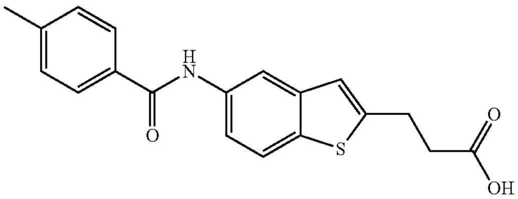 [SMILES: Cc1ccc(C(=O)Nc2ccc3sc(CCC(=O)O)cc3c2)cc1] | >20 | ND | >100 |
| KH-28A | 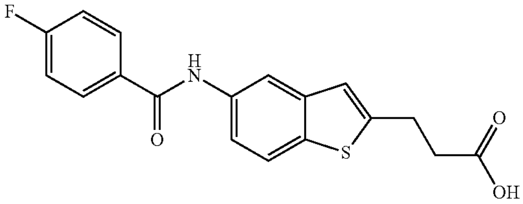 [SMILES: O=C(O)CCc1cc2cc(NC(=O)c3ccc(F)cc3)ccc2s1] | >20 | ND | ND |

TABLE 1-continued
Results of HuR inhibitory activity in FP assay and cytotoxicity assays for compounds of the present technology
| ID | Structure | HuR Ki via FP assay (µM) | Cytotoxicity ($IC_{50}$, µM) MIAPaCa-2 | Cytotoxicity ($IC_{50}$, µM) MDA-MB-231 |
|---|---|---|---|---|
| KH-30A | 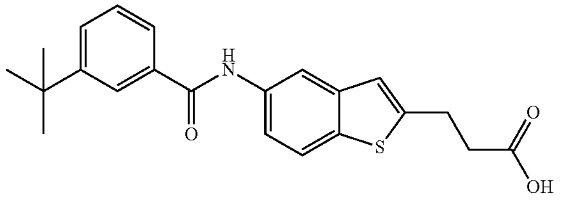 [SMILES: CC(C)(C)c1cccc(C(=O)Nc2ccc3sc(CCC(=O)O)cc3c2)c1] | >20 | ND | >100 |
| KH-31A | 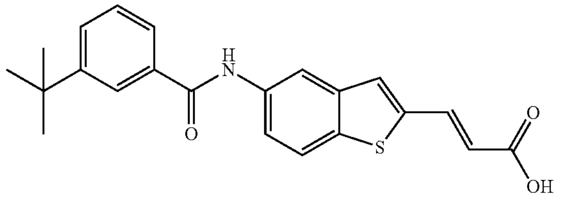 [SMILES: CC(C)(C)c1cccc(C(=O)Nc2ccc3sc(/C=C/C(=O)O)cc3c2)c1] | 2.27 | ND | 95.26 |
| KH-32A | 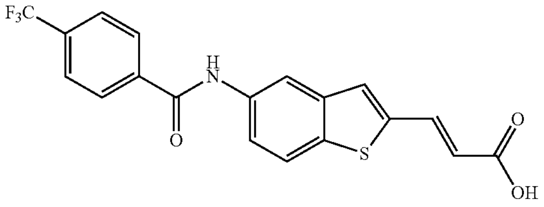 | 1.60 | ND | >100 |
| KH-33A | 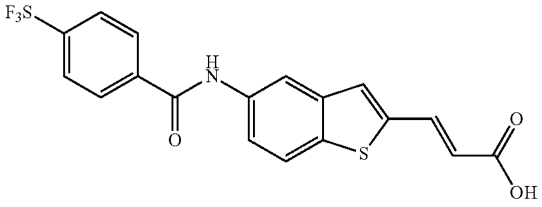 | 1.20 | ND | 50.12 |
| KH-34A | 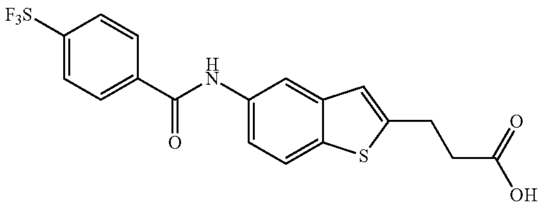 | 5.8 | ND | 48.01 |
| KH-36A | 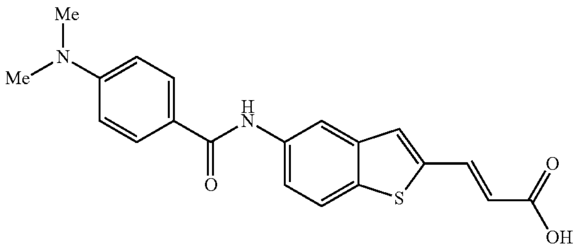 [SMILES: CN(C)c1ccc(C(=O)Nc2ccc3sc(/C=C/C(=O)O)cc3c2)cc1] | 0.12 | ND | >100 |

TABLE 1-continued
Results of HuR inhibitory activity in FP assay and cytotoxicity assays for compounds of the present technology
| ID | Structure | HuR Ki via FP assay (μM) | Cytotoxicity ($IC_{50}$, μM) MIAPaCa-2 | Cytotoxicity ($IC_{50}$, μM) MDA-MB-231 |
|---|---|---|---|---|
| KH-37A | 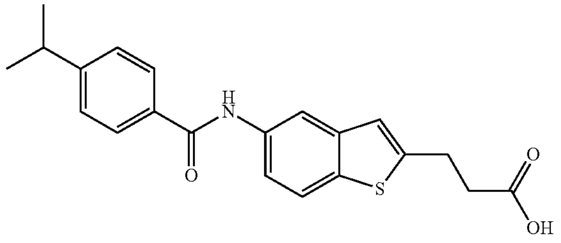 [SMILES: CC(C)c1ccc(C(=O)Nc2ccc3sc(CCC(=O)O)cc3c2)cc1] | >20 | ND | >100 |
| KH-38A | 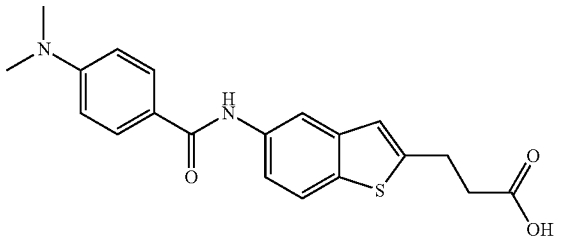 [SMILES: CN(C)c1ccc(C(=O)Nc2ccc3sc(CCC(=O)O)cc3c2)cc1] | >20 | ND | >100 |
| KH-39A | 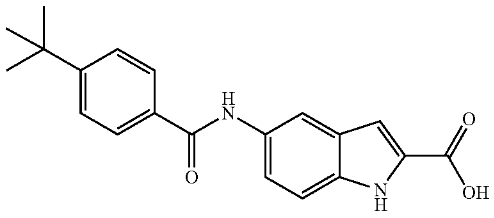 [SMILES: CC(C)(C)c1ccc(C(=O)Nc2ccc3[nH]c(C(=O)O)cc3c2)cc1] | 12.52 | ND | >100 |
| KH-43A | 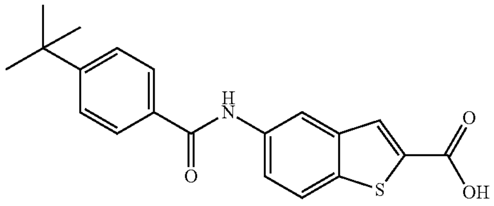 [SMILES: CC(C)(C)c1ccc(C(=O)Nc2ccc3sc(C(=O)O)cc3c2)cc1] | 5.08 | ND | 90.51 |
| KH-46A | 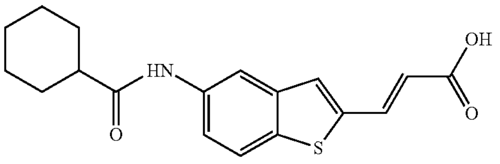 [SMILES: O=C(O)/C=C/c1cc2cc(NC(=O)C3CCCCC3)ccc2s1] | 4.27 | ND | >100 |
| KH-47A | 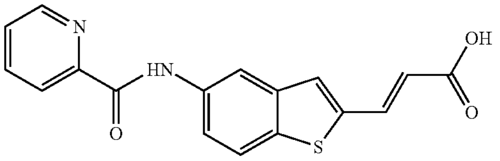 [SMILES: O=C(O)/C=C/c1cc2cc(NC(=O)c3ccccn3)ccc2s1] | 1.81 | ND | 18.18 |

TABLE 1-continued
Results of HuR inhibitory activity in FP assay and cytotoxicity assays for compounds of the present technology
| ID | Structure | HuR Ki via FP assay (µM) | Cytotoxicity ($IC_{50}$, µM) MIAPaCa-2 | Cytotoxicity ($IC_{50}$, µM) MDA-MB-231 |
|---|---|---|---|---|
| KH-48A | 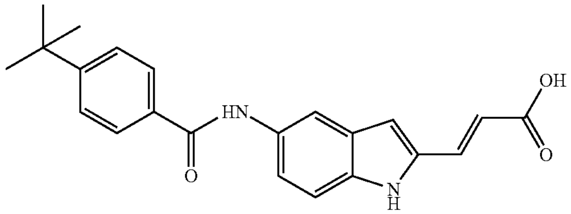 [SMILES: CC(C)(C)c1ccc(C(=O)Nc2ccc3[nH]c(/C=C/C(=O)O)cc3c2)cc1] | 3.35 | ND | >100 |
| KH-52A | 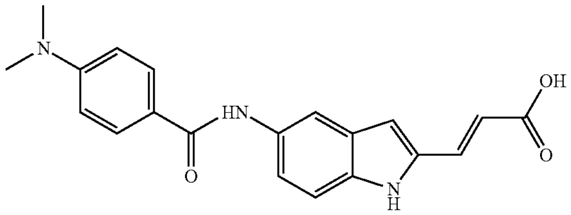 [SMILES: CN(C)c1ccc(C(=O)Nc2ccc3[nH]c(/C=C/C(=O)O)cc3c2)cc1] | 7.76 | ND | >100 |
| KH-56A | 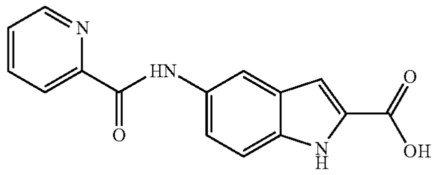 [SMILES: O=C(Nc1ccc2[nH]c(C(=O)O)cc2c1)c1ccccn1] | >20 | ND | >100 |
| KH-57A | 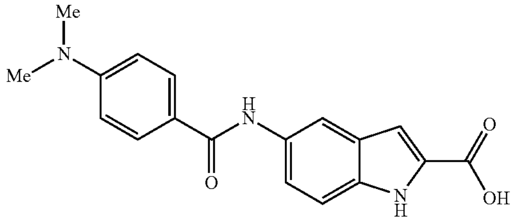 [SMILES: CN(C)c1ccc(C(=O)Nc2ccc3[nH]c(C(=O)O)cc3c2)cc1] | 0.78 | ND | 99.97 |
| KH-58A | 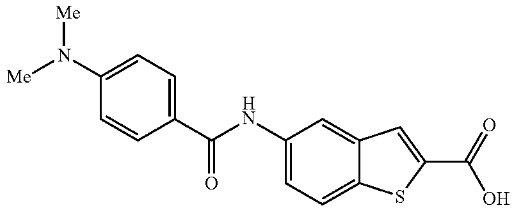 [SMILES: CN(C)c1ccc(C(=O)Nc2ccc3sc(C(=O)O)cc3c2)cc1] | 2.37 | ND | >100 |
| KH-60A | 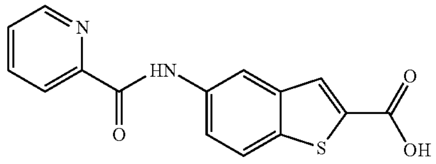 [SMILES: O=C(Nc1ccc2sc(C(=O)O)cc2c1)c1ccccn1] | 1.14 | ND | >100 |

TABLE 1-continued
Results of HuR inhibitory activity in FP assay and cytotoxicity assays for compounds of the present technology
| ID | Structure | HuR Ki via FP assay (μM) | Cytotoxicity ($IC_{50}$, μM) MIAPaCa-2 | MDA-MB-231 |
|---|---|---|---|---|
| KH-19C | 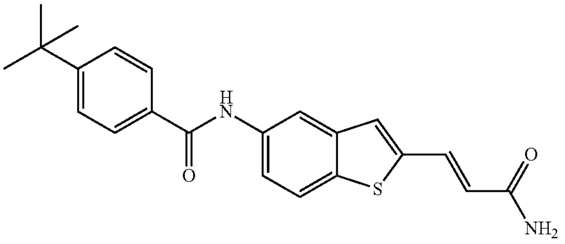 [SMILES: CC(C)(C)c1ccc(C(=O)Nc2ccc3sc(/C=C/C(N)=O)cc3c2)cc1] | 0.6 | ND | 8.676 |
| KH-22C | 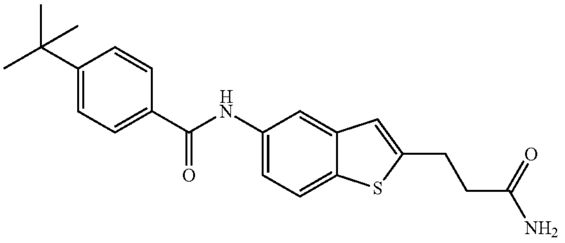 [SMILES: CC(C)(C)c1ccc(C(=O)Nc2ccc3sc(CCC(N)=O)cc3c2)cc1] | 7.0 | ND | 2.868 |
| KH-19E | 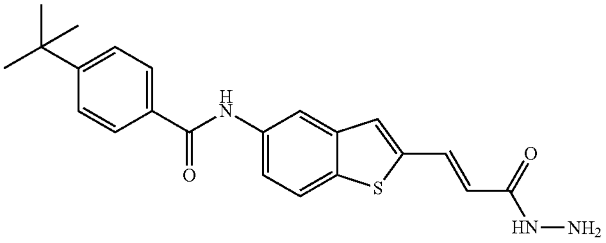 [SMILES: CC(C)(C)c1ccc(C(=O)Nc2ccc3sc(/C=C/C(=O)NN)cc3c2)cc1] | 0.19 | ND | 28.36 |
| KH-22E | 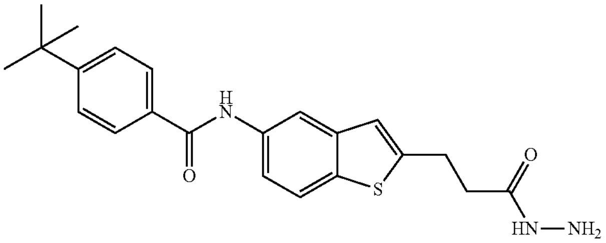 [SMILES: CC(C)(C)c1ccc(C(=O)Nc2ccc3sc(CCC(=O)NN)cc3c2)cc1] | 1.06 | ND | 8.556 |
| KH-29E | 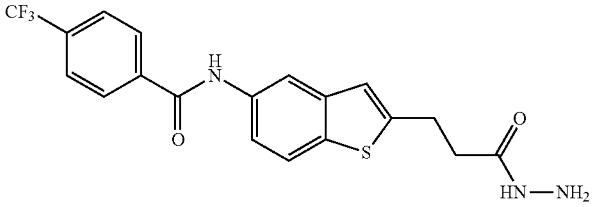 [SMILES: NNC(=O)CCc1cc2cc(NC(=O)c3ccc(C(F)(F)F)cc3)ccc2s1] | 3.32 | ND | 71.18 |
| KH-30E | 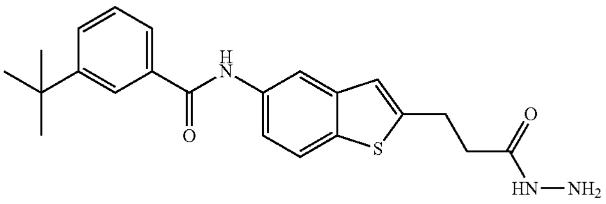 [SMILES: CC(C)(C)c1cccc(C(=O)Nc2ccc3sc(CCC(=O)NN)cc3c2)c1] | 4.19 | ND | 22.66 |

TABLE 1-continued

Results of HuR inhibitory activity in FP assay and cytotoxicity assays for compounds of the present technology

| ID | Structure | HuR Ki via FP assay (μM) | Cytotoxicity ($IC_{50}$, μM) MIAPaCa-2 | MDA-MB-231 |
|---|---|---|---|---|
| KH-37E | 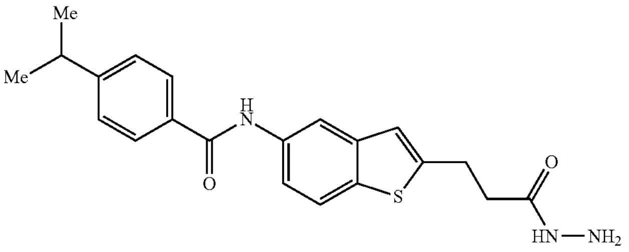 [SMILES: CC(C)c1ccc(C(=O)Nc2ccc3sc(CCC(=O)NN)cc3c2)cc1] | 5.18 | ND | >100 |
| KH-38E | 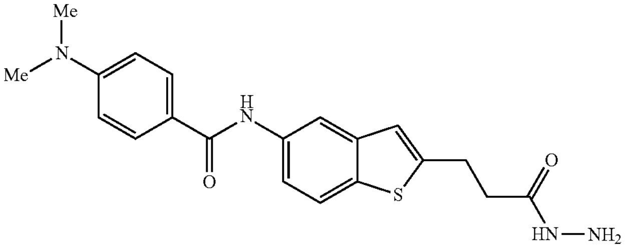 [SMILES: CN(C)c1ccc(C(=O)Nc2ccc3sc(CCC(=O)NN)cc3c2)cc1] | 3.56 | ND | 57.65 |
| KH-39E | 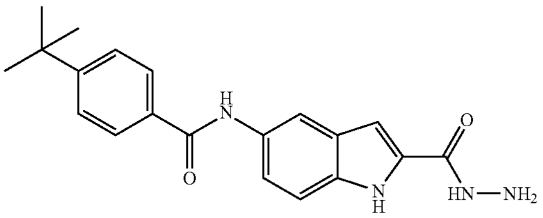 [SMILES: CC(C)(C)c1ccc(C(=O)Nc2ccc3[nH]c(C(=O)NN)cc3c2)cc1] | 1.67 | ND | 13.51 |

"ND" = not yet detemined

TABLE 2

Msi1, Msi2, and LIN28B inhibitory activities of compounds of the present technology in FP assay

| ID | Msi1 (Ki, μM) | Msi2 (Ki, μM) | LIN28B (Ki, μM) |
|---|---|---|---|
| KH-19 | 1.97 | 0.45 (RRM1) | 3.20 |
| KH-20 | >20 | >20 | >20 |
| KH-22 | >20 | >20 | >20 |
| KH-27 | >20 | >20 | >20 |
| KH-29 | >20 | >20 | >20 |
| KH-30 | >20 | >20 | >20 |
| KH-31 | 3.89 | 1.3 (RRM1) | 3 |
| KH-32 | 4.87 | 2.64 (RRM1) | >20 |
| KH-34 | >20 | >20 | >20 |
| KH-36 | ND | 1.5 (RRM1) | 7.1 |
| KH-38 | >20 | >20 | >20 |
| KH-39 | ND | 3.15 (RRM1) | >20 |
| KH-43 | ND | 2.9 (RRM1) | 2.7 |
| KH-46 | ND | >20 | 5.84 |
| KH-47 | ND | >20 | >20 |
| KH-48 | ND | 3.91 (RRM1) | 8.79 |

TABLE 2-continued

Msi1, Msi2, and LIN28B inhibitory activities of compounds of the present technology in FP assay

| ID | Msi1 (Ki, μM) | Msi2 (Ki, μM) | LIN28B (Ki, μM) |
|---|---|---|---|
| KH-52 | ND | >20 | >20 |
| KH-56 | ND | >20 | >20 |
| KH-57 | ND | >20 | >20 |
| KH-58 | ND | 3.35 (RRM1) | 4.57 |
| KH-60 | ND | >20 | >20 |
| KH-19A | 2.24 | 0.28 (RRM1) | >20 |
| KH-20A | >20 | >20 | >20 |
| KH-22A | >20 | >20 | >20 |
| KH-23A | >20 | >20 | >20 |
| KH-27A | >20 | >20 | >20 |
| KH-28A | >20 | >20 | >20 |
| KH-30A | >20 | >20 | >20 |
| KH-31A | 4.60 | 1.36 (RRM1) | >20 |
| KH-32A | 4.36 | 1.68 (RRM1) | >20 |
| KH-33A | 2.63 | 1.03 (RRM1) | >20 |
| KH-34A | >20 | >20 | >20 |
| KH-36A | 0.22 | 0.5 (RRM1) | 1.64 |

TABLE 2-continued

Msi1, Msi2, and LIN28B inhibitory activities of compounds of the present technology in FP assay

| ID | Msi1 (Ki, μM) | Msi2 (Ki, μM) | LIN28B (Ki, μM) |
|---|---|---|---|
| KH-37A | >20 | >20 | >20 |
| KH-38A | >20 | >20 | >20 |
| KH-39A | >20 | 22.01 (RRM1) | >20 |
| KH-43A | ND | 5.25 (RRM1) | >20 |
| KH-46A | ND | >20 | >20 |
| KH-47A | ND | 6.8 (RRM1) | >20 |
| KH-48A | ND | 4.8 (RRM1) | >20 |
| KH-52A | ND | 27.12 (RRM1) | >20 |
| KH-56A | ND | >20 | >20 |
| KH-57A | ND | 2.1 (RRM1) | >20 |
| KH-58A | ND | 6.6 (RRM1) | >20 |
| KH-60A | ND | 4.6 (RRM1) | >20 |
| KH-19C | >20 | 4.83 | >20 |
| KH-22C | >20 | >20 | >20 |
| KH-19E | >20 | >20 | >20 |
| KH-22E | >20 | >20 | >20 |
| KH-29E | >20 | >20 | >20 |
| KH-30E | >20 | >20 | >20 |
| KH-37E | >20 | >20 | >20 |
| KH-38E | >20 | >20 | >20 |
| KH-39E | ND | ND | >20 |

"ND" = not yet determined

TABLE 3

Illustrative cytotoxicity of compounds of the present technology in exemplary colon cancer cell lines.

| ID | HCT116 ($IC_{50}$, μM) | HCT116 β/W ($IC_{50}$, μM) | RKO ($IC_{50}$, μM) | SW480 ($IC_{50}$, μM) |
|---|---|---|---|---|
| KH-19 | 2.22 | 2.63 | 4.48 | 5.14 |
| KH-19A | >100 | 80.61 | 78.49 | >100 |
| KH-19B | >100 | 84.61 | 13.37 | 95.89 |
| KH-36 | 5.05 | 4.00 | 5.74 | 4.89 |
| KH-36A | 98.53 | 99.88 | 62.89 | >100 |
| KH-36B | >100 | >100 | >100 | >100 |

Figure 4A:
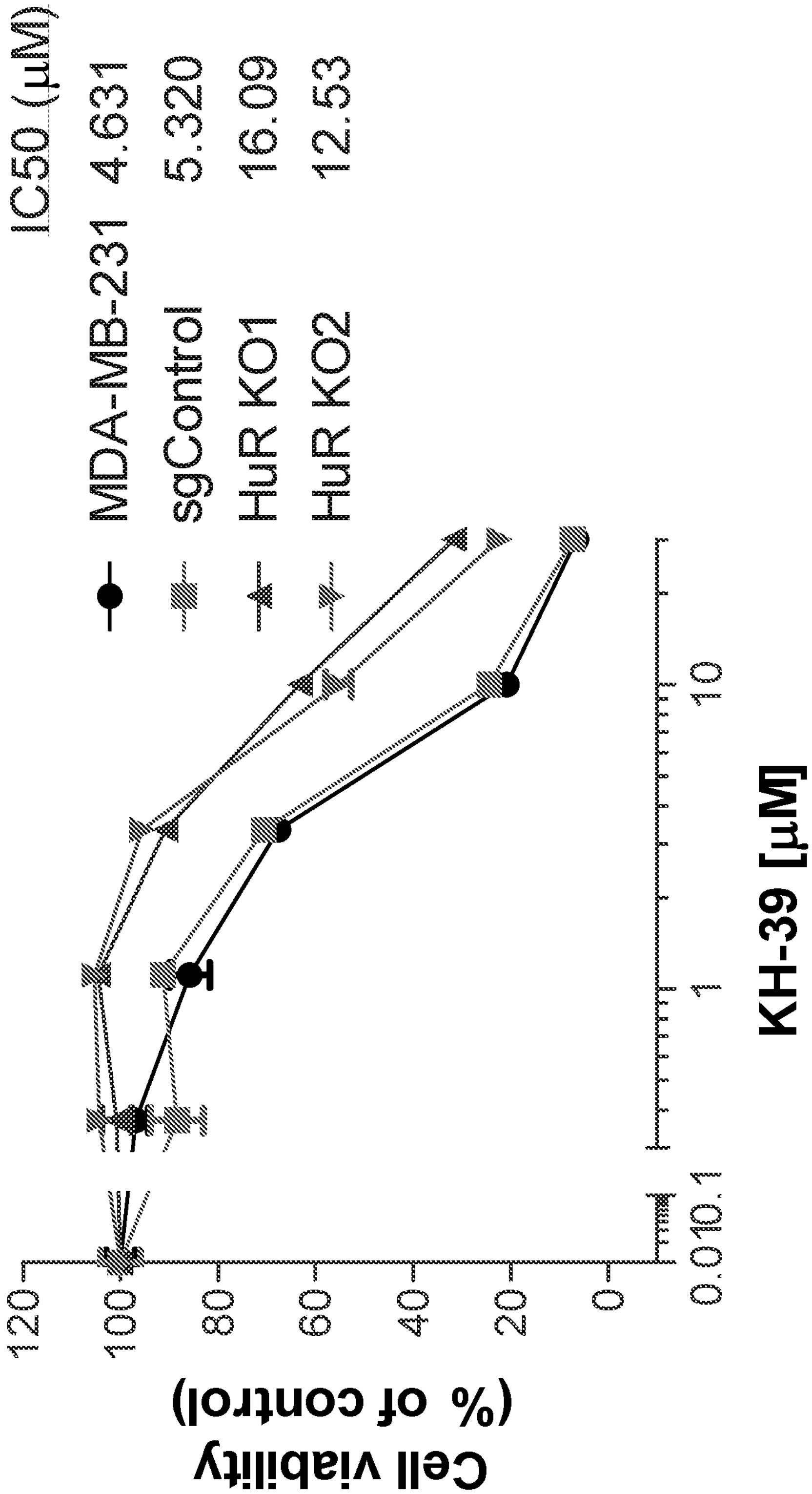
FIGS. 4A-B illustrate the results of studies showing the cytotoxicity of compounds of the present technology —KH-39 (FIG. 4A) and KH-58 (FIG. 4B)—against MDA-MB-231 cells, two clones with HuR knockout (HuR KO1 and HuR KO2), and the vector control cells (sgControl).
Figure 4B:
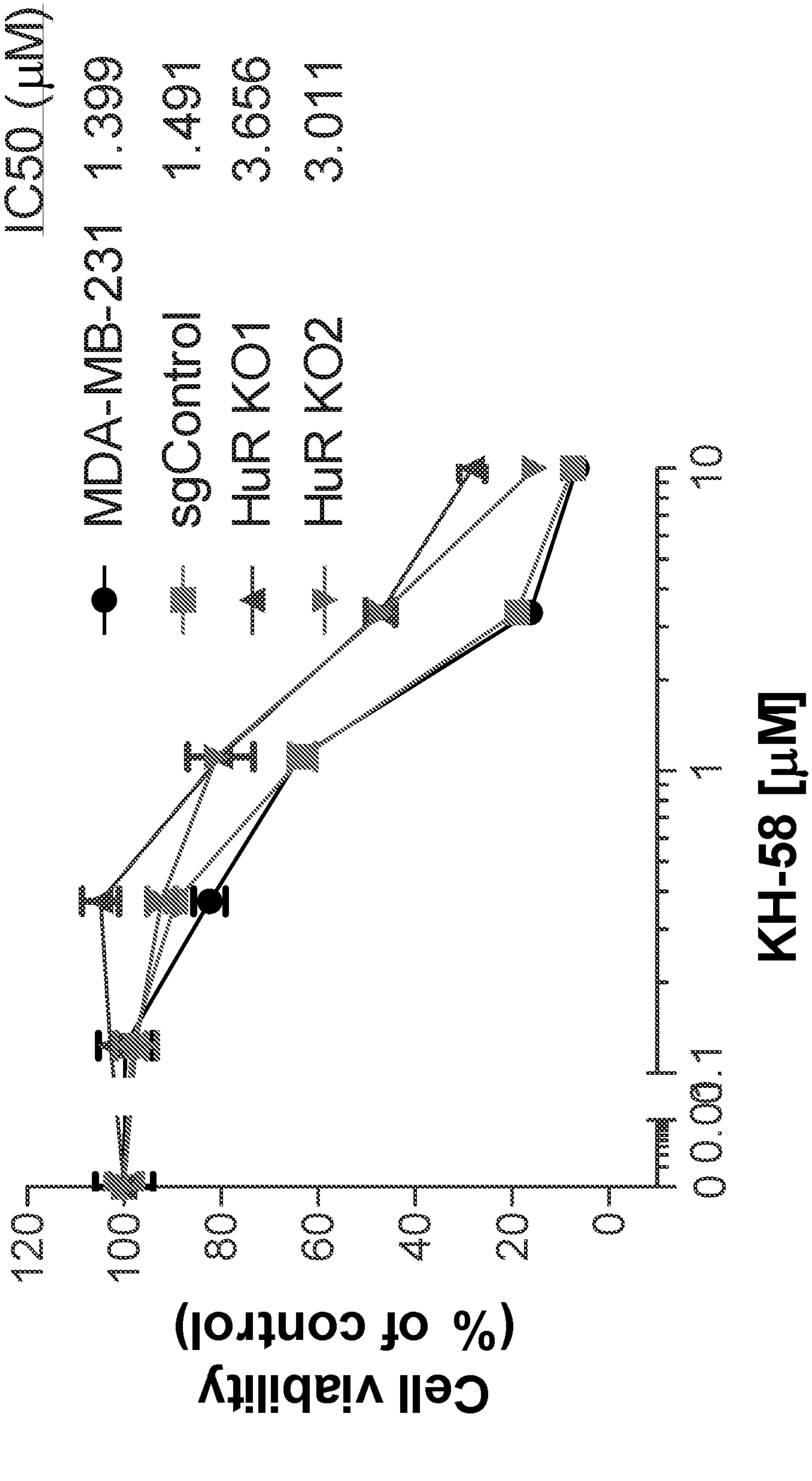

The cytotoxicity of KH-39 and KH-58 against HuR knockout clones was probed by the same assay as described above. FIGS. 4A-B illustrate the results, showing the cytotoxicity of KH-39 (FIG. 4A) and KH-58 (FIG. 4B) against MDA-MB-231 cells, two clones with HuR knockout (HuR KO1 and HuR KO2), and the vector control cells (sgControl). The results illustrate that the two HuR KO clones were less sensitive to both compounds as compared to parental cells and vector control cells, with two to three folds higher $IC_{50}$ values versus the parental cells and vector control cells.

Surface Plasmon Resonance ("SPR") Validation

A BiaCore 3000 instrument will be used to further validate certain findings from the FP assay and will be used on compounds of the present technology. BiaCore 3000 is a SPR-based, high performance research system available for label free studies of biomolecule interactions in real time. Thus, such studies will provide both equilibrium data and kinetic parameters of queried interactions. Both the full length HuR protein as well as its fragments RRM1 and RRM1/2 will be immobilized in separate chambers on a Biacore sensor chip CM5, and then compounds of interest (such as compounds of the present technology) will be injected at a series of concentrations as soluble analytes. Curves will be determined from the experimentally observed curves by successive subtractions of signals obtained for the reference surface and signals for the running buffer injected under the same conditions as the compounds of interest. The data will provide the association/dissociation characteristics of specific interactions of compounds of interest with HuR and its fragments.

Inhibition of Endogenous HuR-mRNA Interaction of HuR-Inhibitors

Two pull-down assays will be further used to illustrate the inhibition of the HuR-mRNA interaction by compounds of the present technology.

Figure 5:
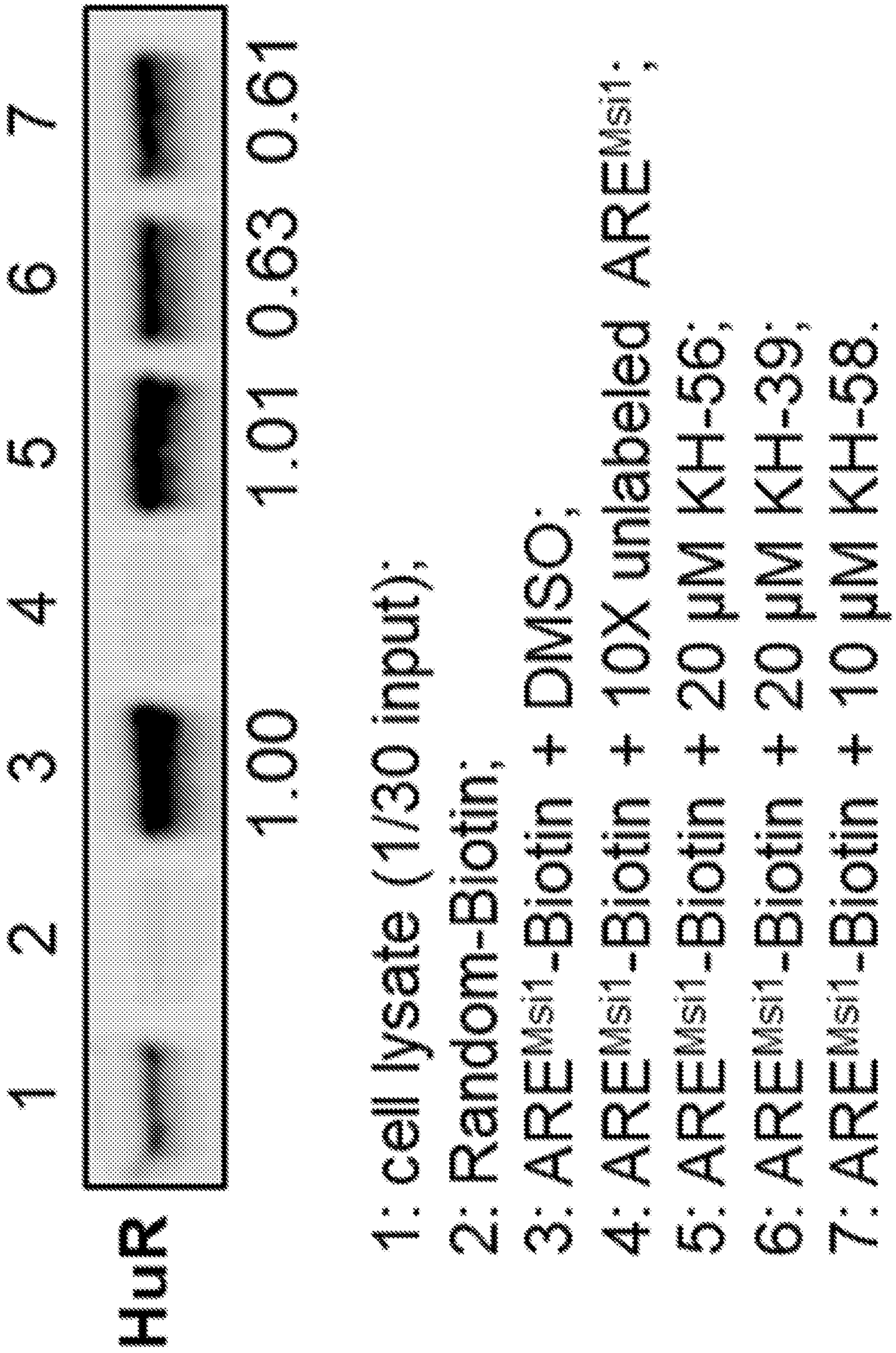
FIG. 5 illustrates the results of a RNA immunoprecipitation (RNA-IP) assay with exemplary compounds of the present technology, according to the working examples.

Pull-down Assay #1—RNA Immunoprecipitation (RNA-IP): Cells with HuR overexpression will be treated with compounds, then the cell cytoplasmic lysates were collected using NE-PER Nuclear and Cytoplasmic Extraction Kit (Thermo Scientific), and subsequently to the cell cytoplasmic lysates were added the biotinylated target ARE oligo from Msi1 mRNA ($ARE^{Msi1}$-Biotin). Following this, streptavidin beads were added to pull down HuR protein bound to $ARE^{Msi1}$-Biotin. Unlabeled target AREs used as positive control. Compounds of the present technology block the HuR pull-down by the biotinylated ARE oligo, illustrating inhibition of the HuR-mRNA interaction. For example, using 20 μM KH-39, 20 μM KH-56, and 10 μM KH-58 in such a RNA-IP assay provided the data illustrated in FIG. 5. The numbers immediately below the pictured bands in FIG. 5 are calculated by diving the band intensity of the particular sample by the band intensity of the DMSO treated sample (entry 3). FIG. 5 shows that 20 μM KH-39 and 10 μM KH-58 block $ARE^{Msi1}$-Biotin mediated pull-down of HuR protein; KH-56 at the concentration used in this particular assay did not show pull-down of HuR protein. The numbers immediately below the pictured bands in FIG. 5 are calculated by diving the band intensity of the particular sample by the band intensity of the DMSO treated sample (entry 3).

Figure 6:
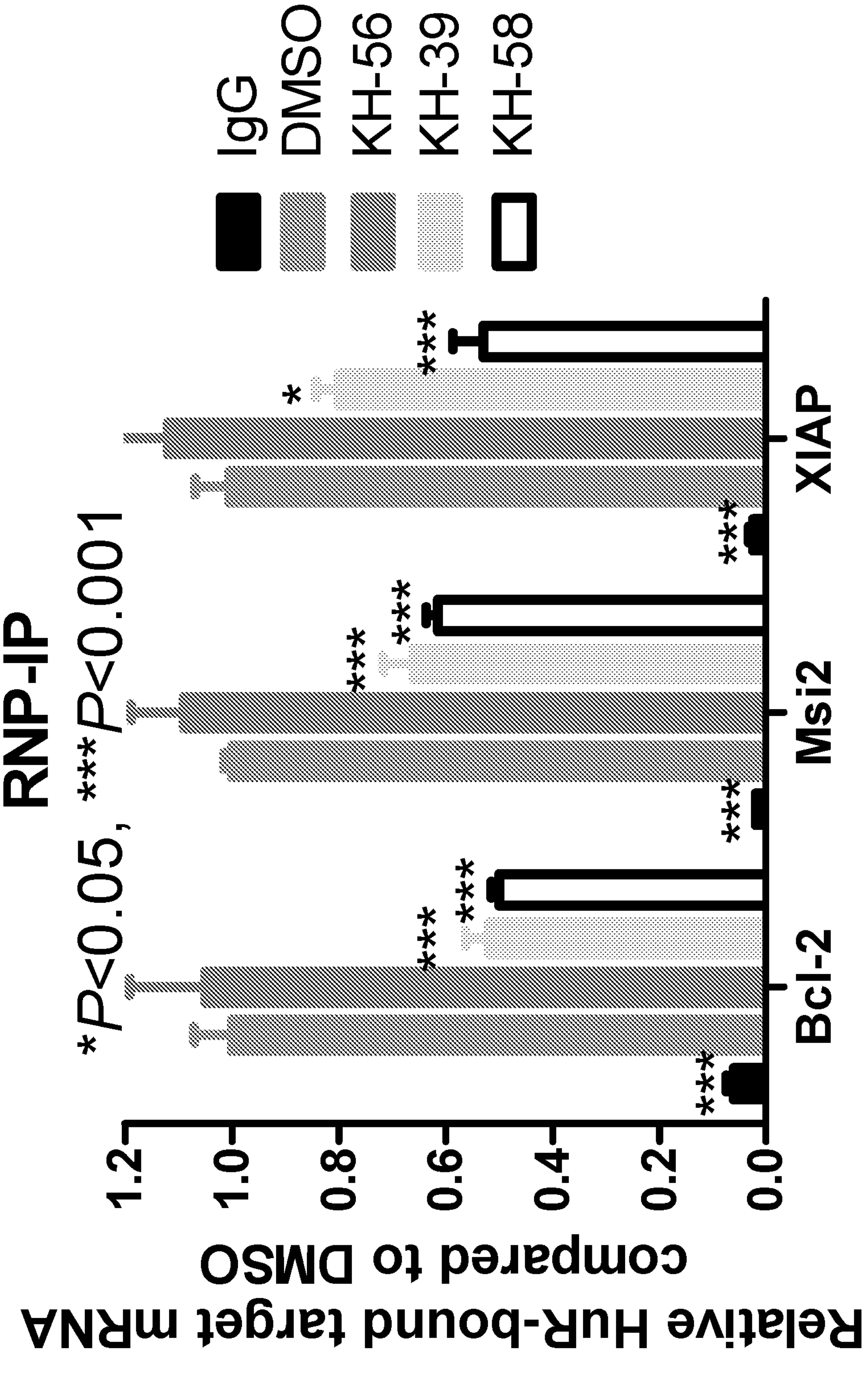
FIG. 6 illustrates the results of a ribonucleoprotein immunoprecipitation (RNP—IP) assay with exemplary compounds of the present technology (KH-39, KH-56, and KH-58) and target mRNAs in MDA-MB-231 cells, according to the working examples.

Pull-down Assay #2—Ribonuleoprotein Immunoprecipitation (RNP—IP): Cells with HuR overexpression were treated with compounds, then the cell cytoplasmic lysates collected using NE-PER Nuclear and Cytoplasmic Extraction Kit (Thermo Scientific), then the cell cytoplasmic lysates incubated with anti-HuR antibody, and subsequently Protein G agarose beads (from Roche) added to pull down HuR protein. The HuR-bound target mRNAs pulled down were measured by qRT-PCR using a reported method (Ji, Q., et al., *MicroRNA miR-*34 *inhibits human pancreatic cancer tumor-initiating cells*. PLoS One, 2009. 4(8): p. e6816, incorporated herein by reference). Mouse IgG will be used as negative control. Compounds of the present technology block the target mRNAs pulled down by HuR antibody. For example, using 10 μM KH-39, 10 μM KH-56, and 5 μM KH-58 in such an RNP—IP assay with target mRNAs in MDA-MB-231 cells provided the data illustrated in FIG. 6, showing that KH-39 and KH-58 at least partially block HuR pull-down of target mRNAs in MDA-MB-231 cells. While KH-56 at the concentration utilized did not provide results statistically distinguishable from vehicle control (see FIG. 6), this is consistent with the results provided in Table 1—that while KH-56 is cytotoxic against MDA-MB-231 cells, KH-56 is less potent against MDA-MB-231 cells than both KH-39 and KH-58.

Inhibition of HuR Target mRNA Stability and Protein Levels of HuR-Inhibitors

Figure 7A:
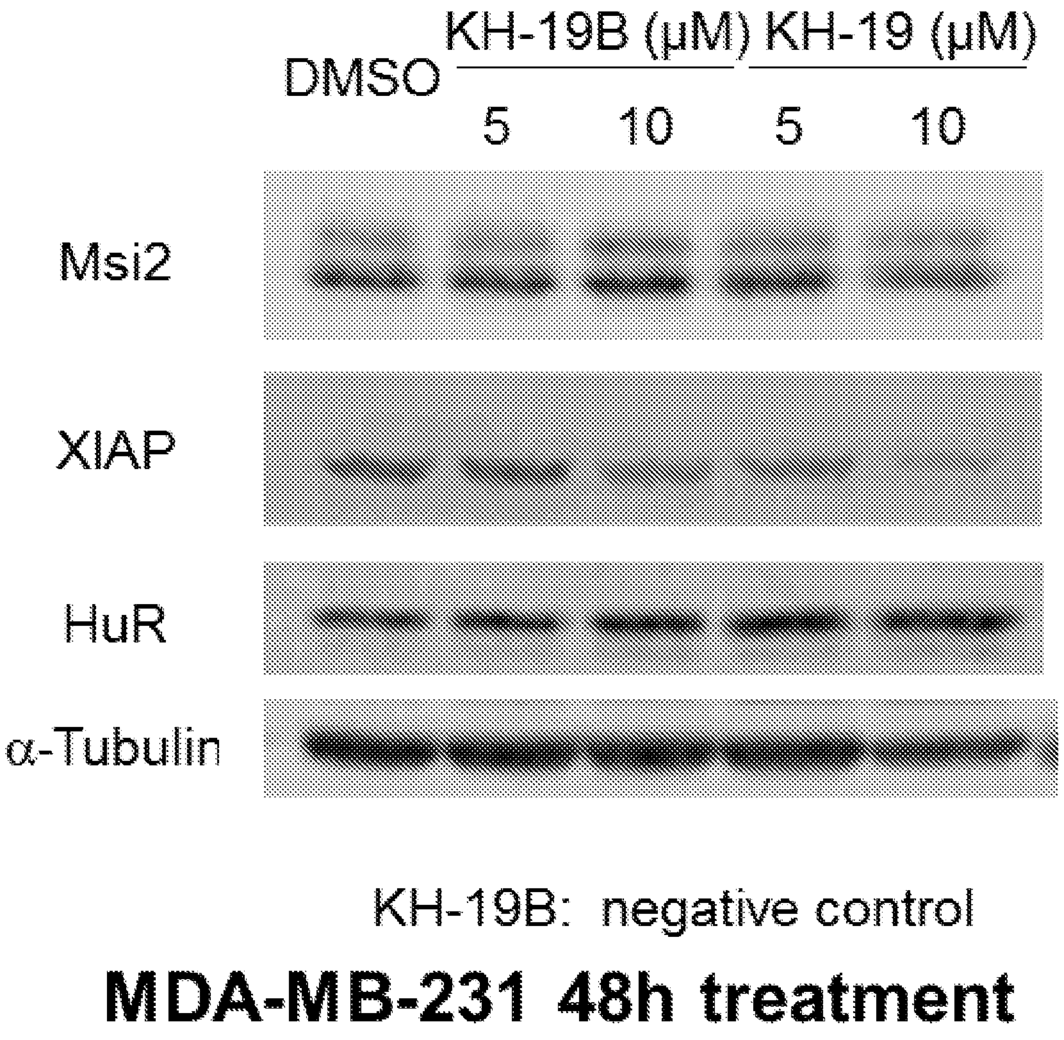
FIGS. 7A-B provide the results of Western blot analysis illustrating that a compound of the present technology (KH-19) decreases the protein levels of HuR targets in MDA-MB-231 cells (FIG. 7A) and is involved in cell death mechanisms by inducing PARP cleavage, LC3 conversion, and RIP3 activation (FIG. 7B).
Figure 7B:
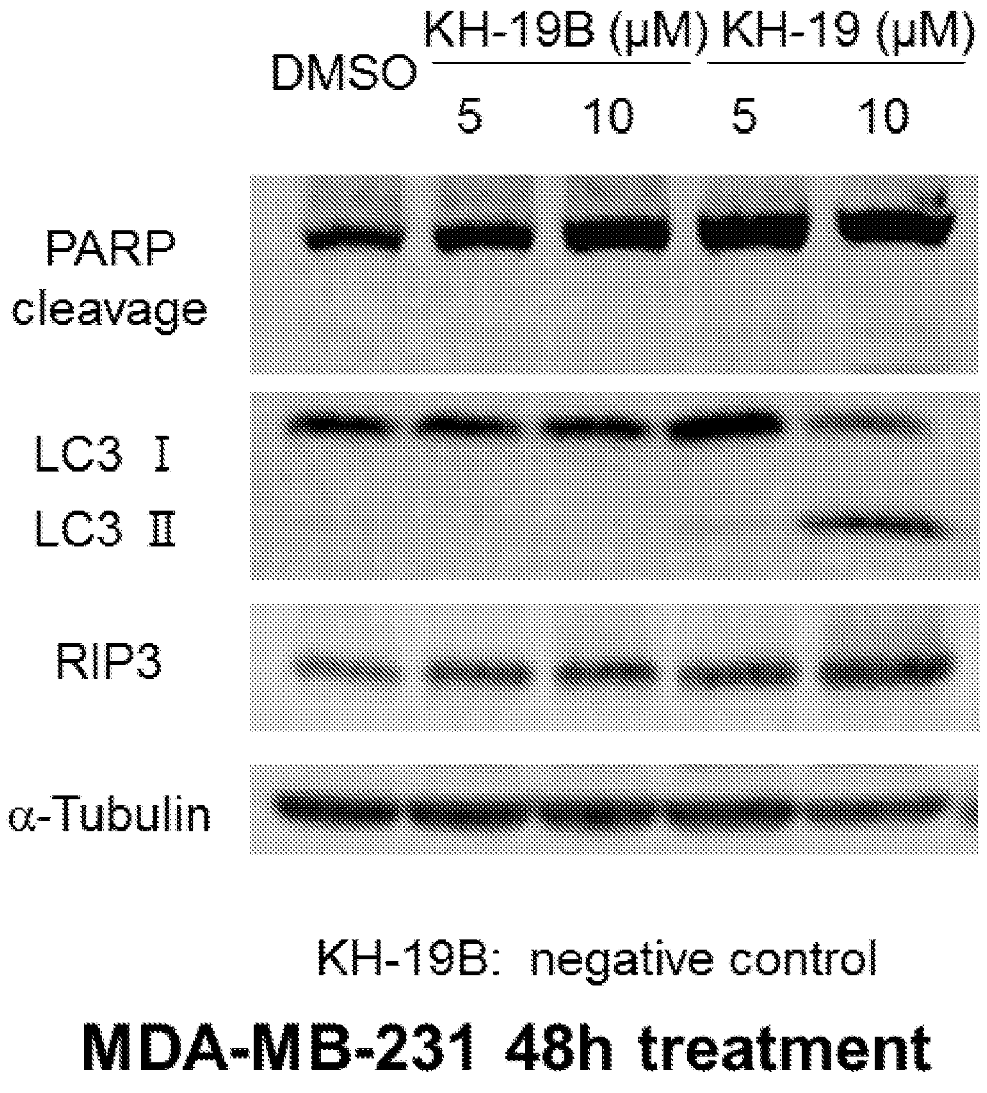

As HuR promotes stability of its target mRNAs, it is expected that HuR-inhibitors will block HuR function and shorten the half-life ($t_{1/2}$) of target mRNAs. mRNA stability will be determined via quantitative real-time PCR (qRT-PCR) after co-treatment of compounds of the present technology and Actinomycin D (a transcription inhibitor). Because HuR also increases the translation of target mRNAs, the effect of compounds of the present technology on protein levels of HuR targets was probed by Western blot analysis. FIGS. 7A-B show that KH-19 decreased the protein levels of HuR targets in MDA-MB-231 cells (FIG. 7A) and also induced cell death through apoptosis, autophagy and necroptosis by inducing PARP cleavage, LC3 conversion, and RIP3 activation, respectively (FIG. 7B). Notably, these properties were not exhibited by negative control KH-19B.

Inhibition of Cancer Cell Metastasis

Figure 8:
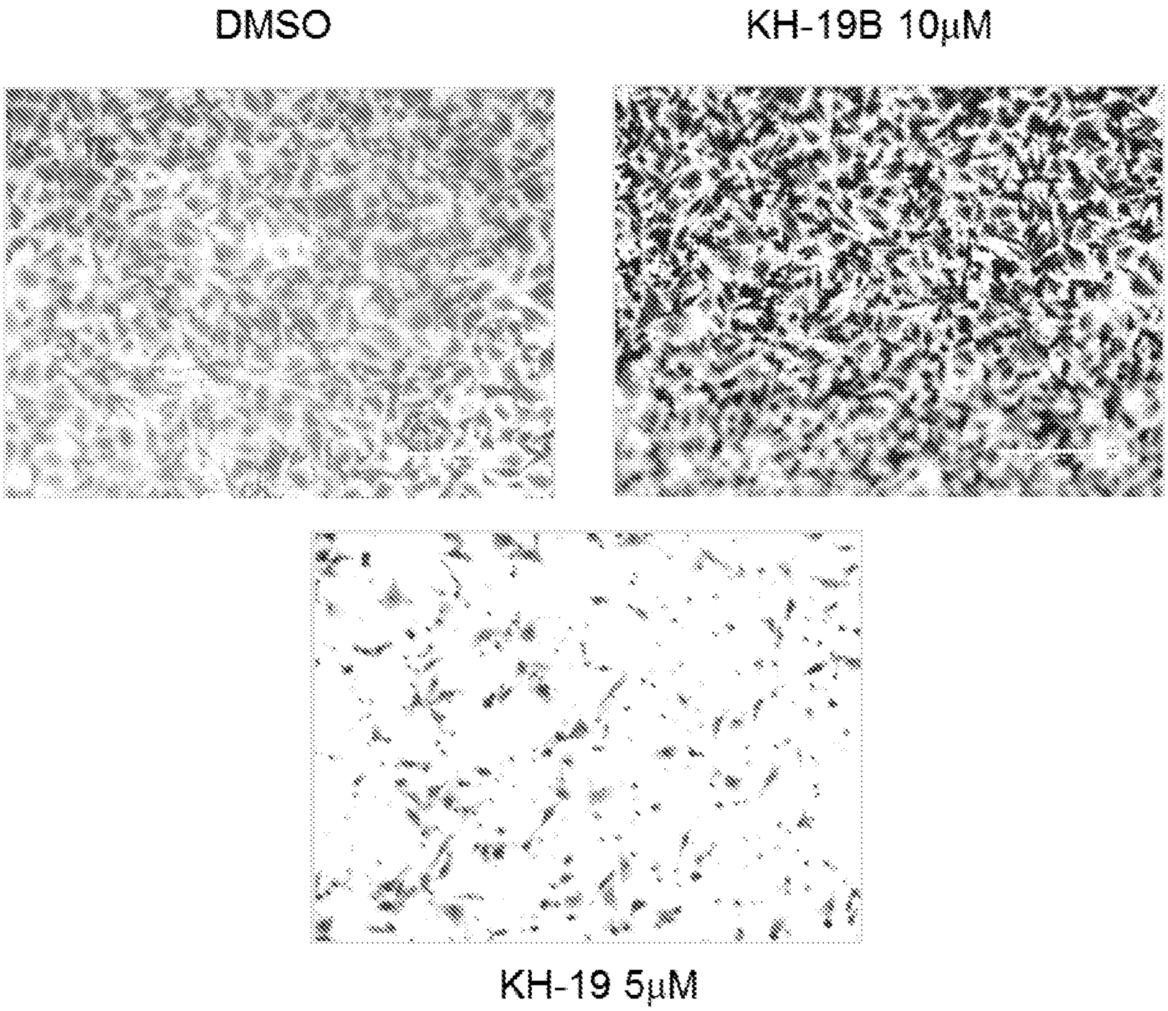
FIG. 8 provides the results of anti-metastatic experiments on MDA-MB-231 cells with a compound of the present technology (KH-19) versus DMSO as well as negative control KH-19B.
Figure 9:
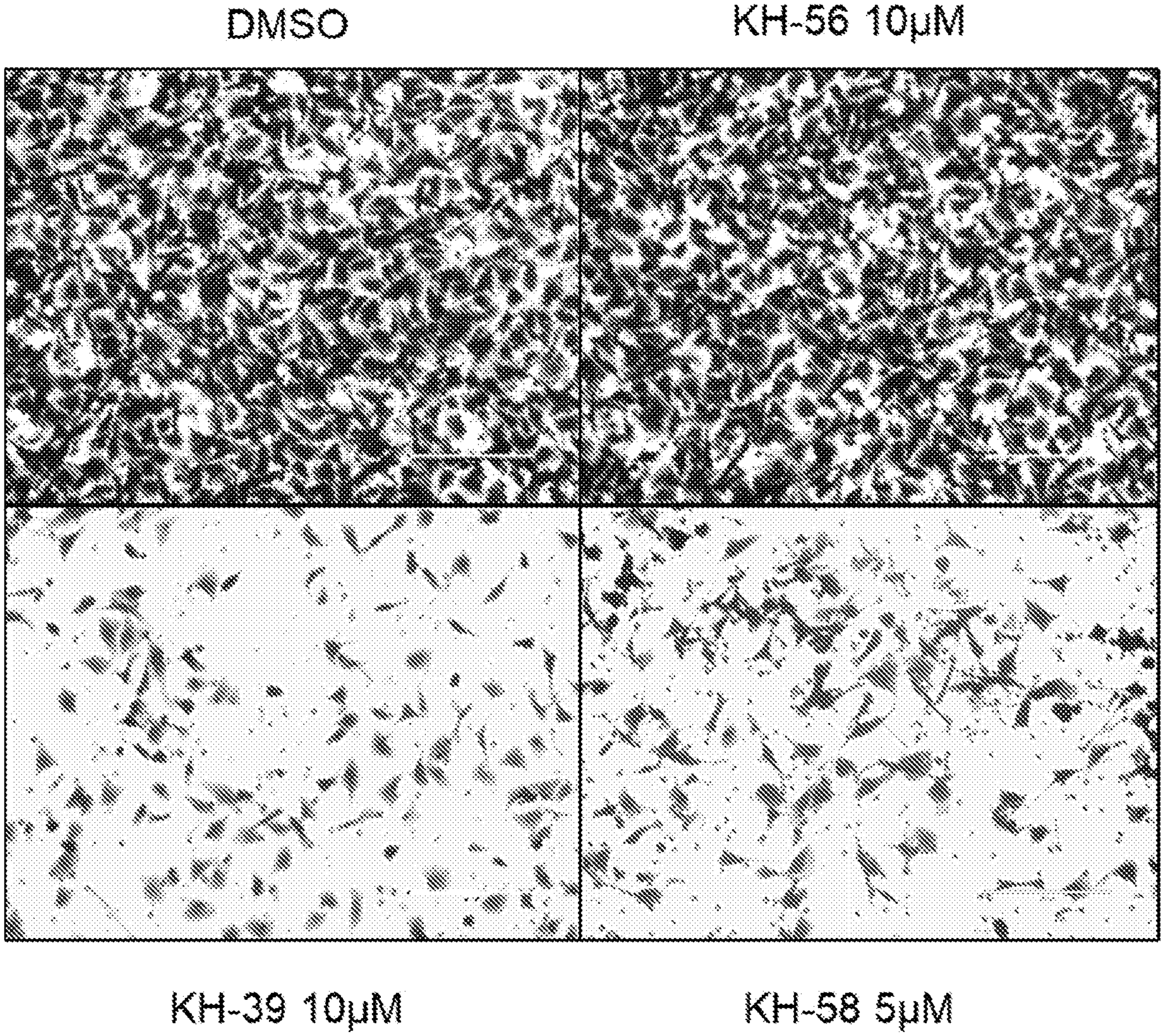
FIG. 9 provides the results of anti-metastatic experiments on MDA-MB-231 cells with certain concentrations of compounds of the present technology (10 μM KH-39, 10 μM KH-56, and 5 μM KH-58) versus DMSO as a control.

To examine the anti-metastatic effect of compounds of the present technology, an invasion assay using Matrigel Invasion Chambers coated with Matrigel Matrix was performed. To perform the assays, MDA-MB-231 cells pretreated with compounds for 24 hours are added to the chambers and then incubated for 20 hours. Cells that remained on the upper surface of the chamber are completely removed with a cotton swab. Cells that emigrated or invaded through the membrane/Matrigel to the bottom of the chamber were fixed and stained with 0.2% crystal violet and photographed. FIG. 8 provides the results of such experiments with KH-19, illustrating that KH-19 inhibited MDA-MB-231 cell invasion while negative control KH-19B did not (concentrations indicated in FIG. 8). FIG. 9 provides the results of such experiments using 10 μM KH-39, 10 μM KH-56, and 5 μM KH-58, where 10 μM KH-39 and 5 μM KH-58 clearly inhibited MDA-MB-231 cell invasion whereas 10 μM KH-56 (which, per Table 1, is less potent against MDA-MB-231 cells than KH-39 and KH-58) did not provide a statistically significant difference in the image as compared to the DMSO control.

In Vivo Anti-Tumor Activity

Initially, the maximum tolerated dose (MTD) will be determined. MTD studies will be conducted as a series of doses and schedule on groups of 3 mice per dose per schedule. Single-dose MTD will be determined first, followed by multi-dose MTD using a schedule that would be used for efficacy studies. Gross necropsies will be performed on all animals as well as selective pathology assessment, including those euthanized, moribund, found dead, or at termination. Liver, heart, kidneys, and other organs will be examined histologically for abnormalities resulting from drug toxicity.

Xenograft and orthotopic models of cancer cell lines with HuR overexpression will be used to test the in vivo therapeutic potential of compounds of the present technology. A person of ordinary skill in the art is well apprised of cancer cell lines with HuR overexpression, as exemplified by references 2-12 cited herein in the "References" section. Tumor models will be established as described in Xu, L., et al., (−)–*Gossypol enhances response to radiation therapy and results in tumor regression of human prostate cancer*. Mol Cancer Ther, 2005. 4(2): p. 197-205.35 Briefly, 4-6 week old athymic NCr-nu/nu mice or 8-10-week-old NOD/SCID mice will be inoculated subcutaneously on both sides of flanks with 0.1 ml of a cell suspension of 1-5×$10^6$ tumor cells. Tumors will be allowed to grow to approximately 100 $mm^3$, when the blood vessel supplies to the tumor are established. Each group will contain at least 5 animals with at least 10 tumors across the five animals. Animals will be given compounds or vehicle i.v., i.p. or q.o.d.×2-3 weeks as described in Xu, L., et al., *Systemic p53 gene therapy of cancer with immunolipoplexes targeted by anti-transferrin receptor scFv*. Mol Med, 2001. 7(10): p. 723-34 and Xu, L., et al., *Self-assembly of a virus-mimicking nanostructure system for efficient tumor-targeted gene delivery*. Hum Gene Ther, 2002. 13(3): p. 469-81.[36, 37]. Compound doses will be less than their predetermined MTD. The tumor sizes and animal body weights will be measured twice a week. The end points for assessing anti-tumor activity will be according to NCI standard procedures[38, 35]. All animal experiments will be carried out according to the protocol approved by the Institutional Animal Use and Care Committee at the University of Kansas.

Figure 10:
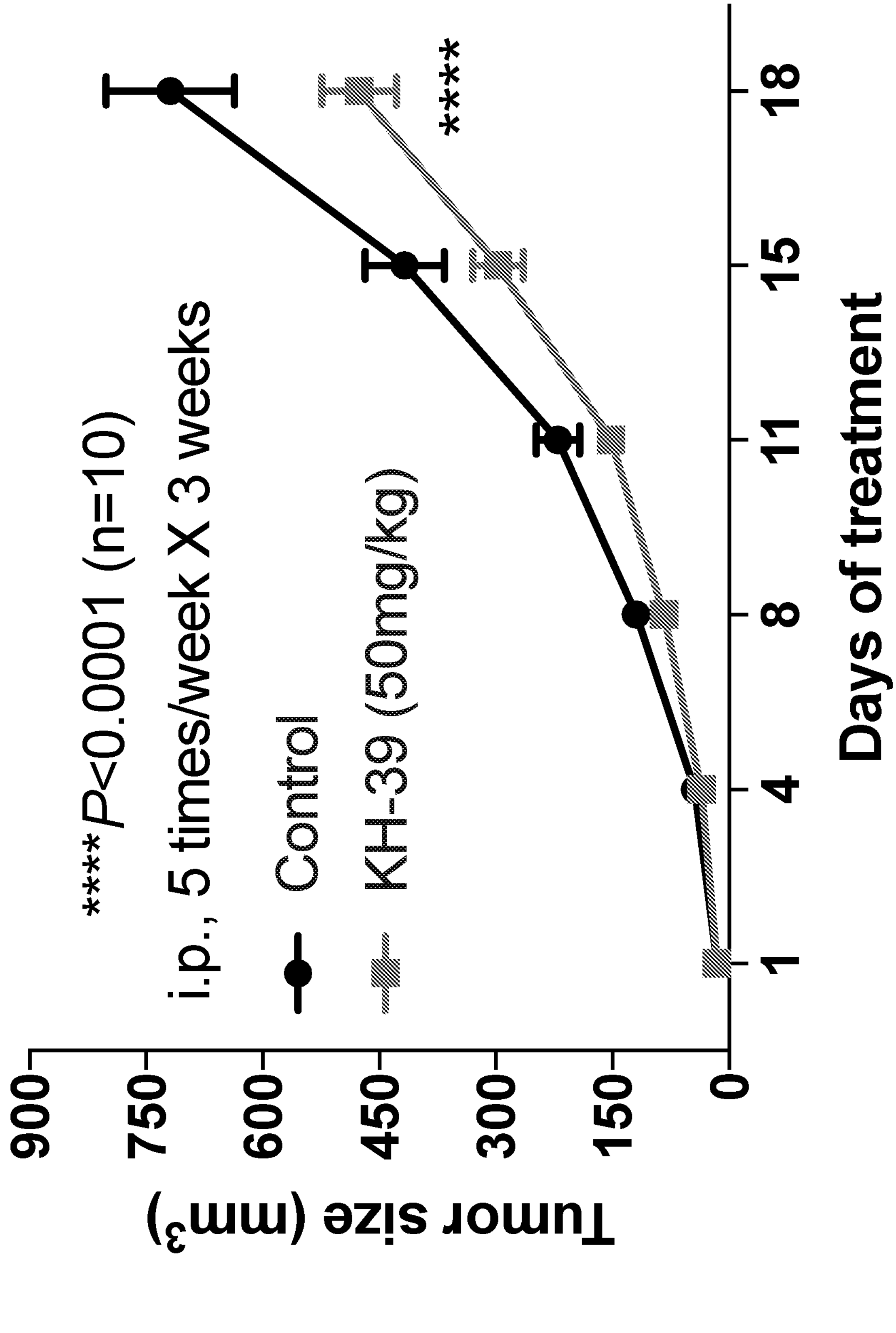
FIG. 10 illustrates the in vivo antitumor activity of an exemplary compound of the present technology (KH-39) in a mouse xenograft model with tumors arising from a subclone generated from MDA-MB-231 and that formed lung metastasis in mice (subclone referred to as "2LMP"), according to the working examples.
Figure 11:
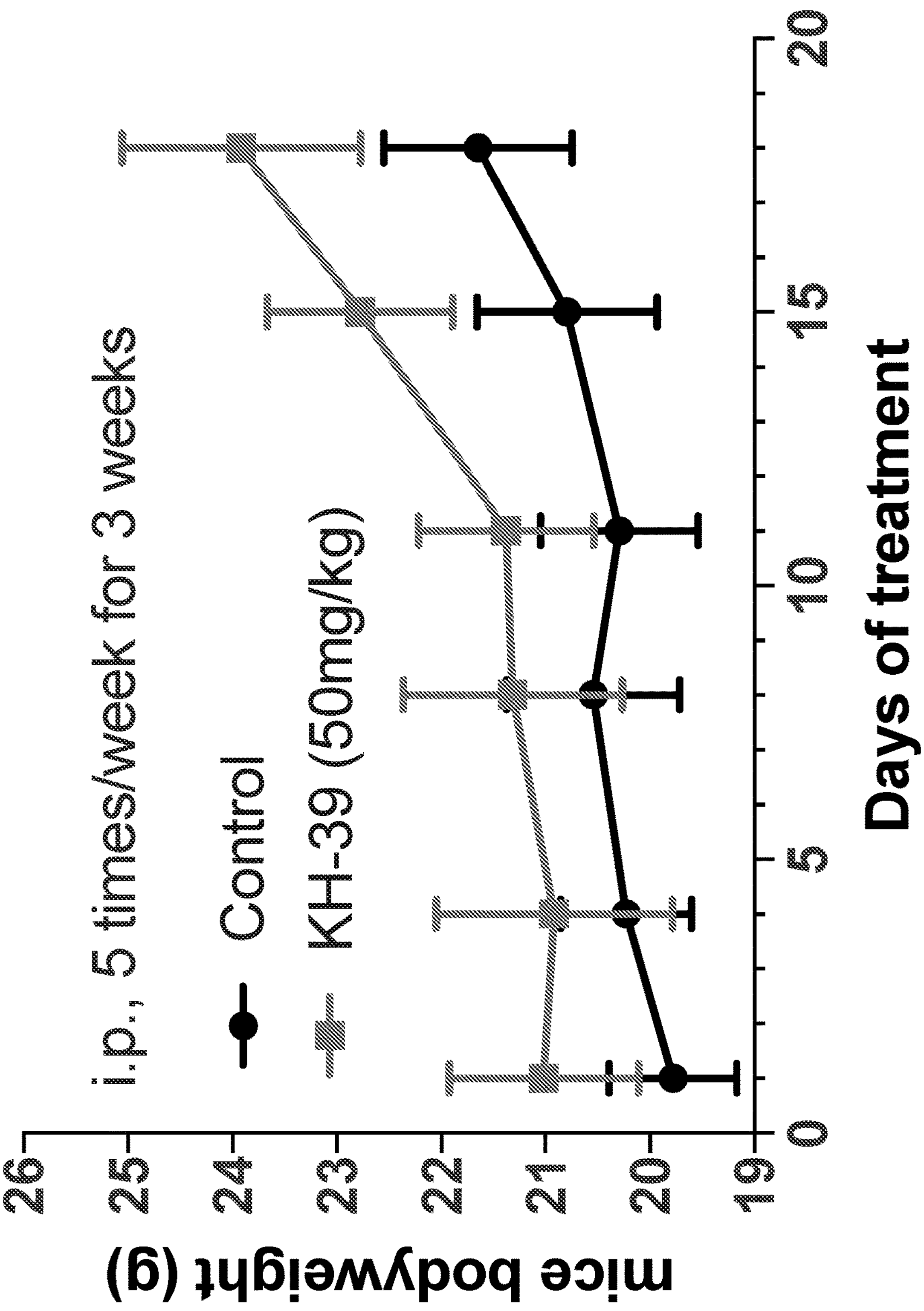
FIG. 11 provides the bodyweight gain of mice in the mouse 2LMP xenograft model that provided the data for FIG. 10, according to the working examples.

Based on preliminary results evidencing that the Ki indicated in the FP assay correlates with in vivo anti-tumor activity, it is expected that compounds of the present technology will significantly decrease tumor growth as compared to the vehicle control in xenograft models ($P<0.001$). By way of an illustrative example, the activity of a compound of the present technology (KH-39) against a cancer xenograft model was performed in mice with tumors arising from a particular cell line—a 2LMP subclone that was generated from MDA-MB-231 and that formed lung metastasis in mice. The 2LMP subclone was kindly gifted by Dr. Marc Lippman. The results of this study are provided in FIGS. 10-11, where FIG. 10 shows that KH-39 significantly decreased tumor growth after three-week treatment as compared to the vehicle control (**$P<0.0001$, n=10), and FIG. 11** illustrates that mice in KH-39 treated group gain bodyweight with similar trend to those in vehicle control group, indicating that KH-39 is well-tolerated in vivo.

Chemo-Sensitization and Overcoming Chemo-Resistance Via Compounds of the Present Technology HuR promotes the translation of several target mRNAs that encode proteins involved in cancer treatment resistance, as discussed in U.S. Pat. Appl. No. 63/001,631 filed Mar. 30, 2020 (incorporated herein by reference) as well as in the relevant literature. Accordingly, studies utilizing compounds of the present technology are expected to illustrate that compounds of the present technology may be administered to overcome acquired chemo-resistance as well as be used in combination with a chemotherapeutic compound (e.g., docetaxel or doxorubicin) to sensitize cancer cell lines (including chemo-resistance cancer cell lines) to chemotherapy.

Figure 12:
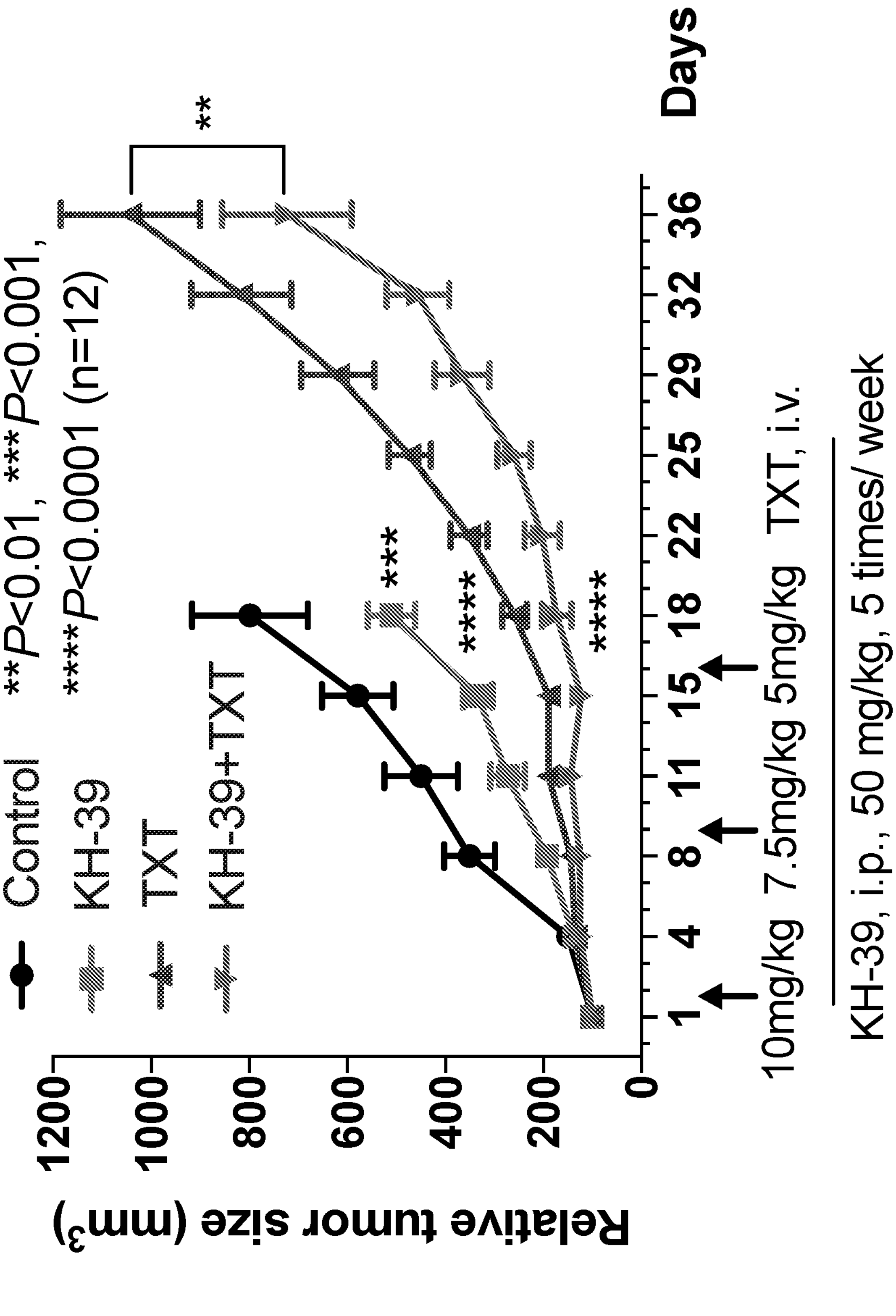
FIG. 12 illustrates the in vivo antitumor activity in a MDA-MB-231 mouse xenograft model for mice receiving one of the following administration regimes: KH-39, docetaxel (TXT), a combination of KH-39 and docetaxel (KH-39+TXT), and vehicle control, according to the working examples. As shown by FIG. 12, relative tumor sizes in three treated groups after three-week treatment were all significantly smaller than those in control group (*$P<0.001$, $P<0.0001$, n=12); at the end of study, relative tumor sizes in the combination group (KH-39+TXT) were significantly smaller than those in the group treated with docetaxel alone ($P<0.01$, n=12).

Cytotoxicity assays (as described earlier in this disclosure) for various cancer cell lines will also be performed utilizing concentrations of a compound of the present technology that are below the lethal threshold for the compound for the particular cancer (a "sub-lethal concentration") in combination with a chemotherapeutic compound (e.g., docetaxel or doxorubicin) to illustrate compounds of the present technology sensitize cancer cell lines to chemotherapy. By way of illustration in an in vivo model, in vivo antitumor efficacy of KH-39 was examined in combination with docetaxel (a first-line chemotherapy for human breast cancer) in a MDA-MB-231 mouse xenograft model. For this, tumor-bearing female athymic mice were provided according to the protocols described earlier in the present disclosure and were randomized into four groups. One group of mice was treated with KH-39 (i.p. 50 mg/kg, 5 times per week), one group with docetaxel (TXT; i.v. at the dosages and time intervals indicated in FIG. 12), one group with a combination of KH-39 and TXT (KH-39 i.p. 50 mg/kg, 5 times per week and TXT i.v. at the dosages and time intervals indicated in FIG. 12), and one group of mice as the vehicle control. FIG. 12 illustrates the results, providing the tumor growth curves for each group. As shown by FIG. 12, relative tumor sizes in three treated groups after three-week treatment were all significantly smaller than those in control group (*P<0.001, P<0.0001, n=12); at the end of study, relative tumor sizes in the combination group (KH-39+TXT) were significantly smaller than those in the group treated with docetaxel alone (P<0.01, n=12). Thus, these results indicate that compounds of the present technology alone are effective in treating tumors, but also that using a compound of the present technology in combination with chemotherapeutic sensitizes the tumor cells to the chemotherapeutic.

To further mimic clinical conditions and assess overcoming acquired chemo-resistance via compounds of the present technology, cytotoxicity assays will be performed to assess the chemo-resistance of the chemoresistant cell lines and then used assess the sensitivity of such chemo-resistant cell lines to compounds of the present technology. Chemoresistant cell lines may be acquired or may be produced—for example, docetaxel-resistant and doxorubicin-resistant MDA-MB-231 cells may be generated by continuous exposure of cells to increasing concentrations of docetaxel (TXT) or doxorubicin (DXR). It is expected that the results will demonstrate that the compounds of the present technology are effective against chemo-resistant cancers and overcome acquired chemo-resistance.

Further, in vivo xenograft models of chemoresistant cell lines (as provided in this disclosure for other cancel cell lines) are likewise expected to demonstrate that the compounds of the present technology are effective against chemo-resistant cancers and overcome acquired chemo-resistance

REFERENCES

1. Brennan, C. M. and J. A. Steitz, *HuR and mRNA stability*. Cell Mol Life Sci, 2001. 58(2): p. 266-77.
2. Lopez de Silanes, I., et al., *Role of the RNA-binding protein HuR in colon carcinogenesis*. Oncogene, 2003. 22(46): p. 7146-54.
3. Nabors, L. B., et al., *HuR, a RNA stability factor, is expressed in malignant brain tumors and binds to adenine- and uridine-rich elements within the 3' untranslated regions of cytokine and angiogenic factor mRNAs*. Cancer Res, 2001. 61(5): p. 2154-61.
4. Dixon, D. A., et al., *Altered expression of the mRNA stability factor HuR promotes cyclooxygenase-2 expression in colon cancer cells*. J Clin Invest, 2001. 108(11): p. 1657-65.
5. Young, L. E., et al., *The mRNA binding proteins HuR and tristetraprolin regulate cyclooxygenase 2 expression during colon carcinogenesis*. Gastroenterology, 2009. 136 (5): p. 1669-79.
6. Yoo, P. S., et al., *Tissue microarray analysis of 560 patients with colorectal adenocarcinoma: high expression of HuR predicts poor survival*. Ann Surg Oncol, 2009. 16(1): p. 200-7.
7. Niesporek, S., et al., *Expression of the ELAV-like protein HuR in human prostate carcinoma is an indicator of disease relapse and linked to COX-2 expression*. Int J Oncol, 2008. 32(2): p. 341-7.
8. Barbisan, F., et al., *Overexpression of ELAV-like protein HuR is associated with increased COX-2 expression in atrophy, high-grade prostatic intraepithelial neoplasia, and incidental prostate cancer in cystoprostatectomies*. Eur Urol, 2009. 56(1): p. 105-12.
9. Heinonen, M., et al., *Prognostic role of HuR in hereditary breast cancer*. Clin Cancer Res, 2007. 13(23): p. 6959-63.
10. Denkert, C., et al., *Overexpression of the embryonic-lethal abnormal vision-like protein HuR in ovarian carcinoma is a prognostic factor and is associated with increased cyclooxygenase 2 expression*. Cancer Res, 2004. 64(1): p. 189-95.
11. Costantino, C. L., et al., *The role of HuR in gemcitabine efficacy in pancreatic cancer: HuR Up-regulates the expression of the gemcitabine metabolizing enzyme deoxycytidine kinase*. Cancer Res, 2009. 69(11): p. 4567-72.
12. Wang, J., et al., *The expression of RNA-binding protein HuR in non-small cell lung cancer correlates with vascular endothelial growth factor-C expression and lymph node metastasis*. Oncology, 2009. 76(6): p. 420-9.
13. Abdelmohsen, K. and M. Gorospe, *Posttranscriptional regulation of cancer traits by HuR*. Wiley Interdiscip Rev RNA, 2010. 1(2): p. 214-29.
14. Srikantan, S. and M. Gorospe, *HuR function in disease*. Front Biosci, 2012. 17: p. 189-205.
15. Wang, J., et al., *Multiple Functions of the RNA-Binding Protein HuR in Cancer Progression, Treatment Responses and Prognosis*. Int J Mol Sci, 2013. 14(5): p. 10015-41.
16. Abdelmohsen, K., et al., *miR-519 suppresses tumor growth by reducing HuR levels*. Cell Cycle, 2010. 9(7): p. 1354-9.
17. Fialcowitz-White, E. J., et al., *Specific protein domains mediate cooperative assembly of HuR oligomers on AU-rich mRNA-destabilizing sequences*. J Biol Chem, 2007. 282(29): p. 20948-59.
18. Wang, H., et al., *The structure of the ARE-binding domains of Hu antigen R (HuR) undergoes conformational changes during RNA binding*. Acta Crystallogr D Biol Crystallogr, 2013. 69(Pt 3): p. 373-80.
19. Doller, A., J. Pfeilschifter, and W. Eberhardt, *Signalling pathways regulating nucleo-cytoplasmic shuttling of the mRNA-binding protein HuR*. Cell Signal, 2008. 20(12): p. 2165-73.
20. Zhu, Z., et al., *Cytoplasmic HuR expression correlates with P-gp, HER-2 positivity, and poor outcome in breast cancer*. Tumour Biol, 2013.
21. Barker, A., et al., *Sequence requirements for RNA binding by HuR and AUF1*. J Biochem, 2012. 151(4): p. 423-37.
22. Filippova, N., et al., *The RNA-binding protein HuR promotes glioma growth and treatment resistance*. Mol Cancer Res, 2011. 9(5): p. 648-59.
23. Durie, D., et al., *RNA-binding protein HuR mediates cytoprotection through stimulation of XIAP translation*. Oncogene, 2011. 30(12): p. 1460-9.
24. Vo, D. T., et al., *The oncogenic RNA-binding protein Musashi 1 is regulated by HuR via mRNA translation and stability in glioblastoma cells*. Mol Cancer Res, 2012. 10(1): p. 143-55.
25. Lebedeva, S., et al., *Transcriptome-wide analysis of regulatory interactions of the RNA-binding protein HuR*. Mol Cell, 2011. 43(3): p. 340-52.
26. Choudhury, N. R., et al., *Tissue-specific control of brain-enriched miR-7 biogenesis*. Genes Dev, 2013. 27(1): p. 24-38.
27. Wang, L., et al., *ATDC TRIM29 Phosphorylation by ATM/MAPKAP Kinase 2 Mediates Radioresistance in Pancreatic Cancer Cells*. Cancer Research, 2014. 74(6): p. 1778-1788.

28. Deng, L., et al., *microRNA100 inhibits self-renewal of breast cancer stem-like cells and breast tumor development*. Cancer Research, 2014.
29. Ginestier, C., et al., *ALDH1 Is a Marker of Normal and Malignant Human Mammary Stem Cells and a Predictor of Poor Clinical Outcome*. Cell Stem Cell, 2007. 1(5): p. 555-567.
30. Al-Hajj, M., et al., *Prospective identification of tumorigenic breast cancer cells*. Proc Natl Acad Sci USA, 2003. 100(7): p. 3983-8.
31. Ishimaru, D., et al., *Regulation of Bcl-2 expression by HuR in HL60 leukemia cells and A431 carcinoma cells*. Mol Cancer Res, 2009. 7(8): p. 1354-66.
32. Ratti, A., et al., *A role for the ELAV RNA-binding proteins in neural stem cells: stabilization of Msi1 mRNA*. J Cell Sci, 2006. 119(Pt 7): p. 1442-52.
33. Wu, X., et al., *Identification and Validation of Novel Small Molecule Disruptors of HuR-mRNA Interaction*. ACS Chem Biol, 2015.
34. Mills, N. L., A. A. Shelat, and R. K. Guy, *Assay Optimization and Screening of RNA-Protein Interactions by AlphaScreen*. J Biomol Screen, 2007. 12(7): p. 946-55.
35. Xu, L., et al., (−)-*Gossypol enhances response to radiation therapy and results in tumor regression of human prostate cancer*. Mol Cancer Ther, 2005. 4(2): p. 197-205.
36. Xu, L., et al., *Systemic p53 gene therapy of cancer with immunolipoplexes targeted by anti-transferrin receptor scFv*. Mol Med, 2001. 7(10): p. 723-34.
37. Xu, L., et al., *Self-assembly of a virus-mimicking nanostructure system for efficient tumor-targeted gene delivery*. Hum Gene Ther, 2002. 13(3): p. 469-81.
38. Corbett, T. H., *Transplantable syngeneic rodent tumors*. Tumor Models in Cancer Research, ed. B. A. Teicher. 2002, Totowa: Humana Press. pp41-71.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound according to Formula I (I)

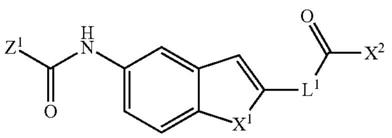

or a pharmaceutically acceptable salt thereof, wherein $Z^1$ is aryl, heteroaryl, or cycloalkyl;

$L^1$ is absent, —$CH_2$—, —$CH_2$—$CH_2$—, or —CH=CH—;

$X^1$ is O, NH, or S; and $X^2$ is OH, $NH_2$, NH—OH, NH—$NH_2$, or O—($C_1$-$C_6$ alkyl).

B. The compound of Paragraph A, wherein $Z^1$ is

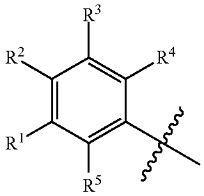 , 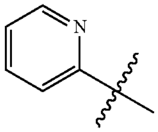 , or 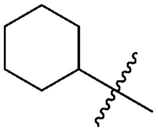 , $R^4$, and $R^5$ are each independently H, halo, hydroxy, amino, cyano, trifluoromethyl, thiol, alkylthio, sulfoxide, sulfone, nitro, pentafluorosulfanyl, carboxylate, amide, ester, $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, or aryloyloxy group, where any two adjacent $R^1$, $R^2$, $R^3$, $R^4$, and $R^5$ may join to form a 5-membered alkyl, heteroalkyl, aryl or heteroaryl.

C. The compound of Paragraph A or Paragraph B, where the compound is of Formula IA (IA)

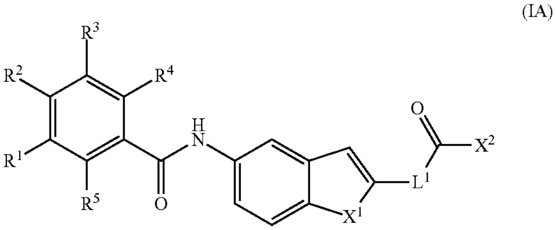

or a pharmaceutically acceptable salt thereof, wherein $R^1$, $R^2$, $R^3$, $R^4$, and $R^5$ are each independently H, halo, hydroxy, amino, cyano, trifluoromethyl, thiol, alkylthio, sulfoxide, sulfone, nitro, pentafluorosulfanyl, carboxylate, amide, ester, $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, or aryloyloxy group, where any two adjacent $R^1$, $R^2$, $R^3$, $R^4$, and $R^5$ may join to form a 5-membered alkyl, heteroalkyl, aryl or heteroaryl, and provided that at least one of $R^1$, $R^2$, $R^3$, $R^4$, and $R^5$ is not H.

D. The compound of any one of Paragraphs A-C, wherein $R^1$, $R^2$, $R^3$, $R^4$, and $R^5$ are each independently H, halo, hydroxy, amino, cyano, trifluoromethyl, thiol, nitro, pentafluorosulfanyl, or $C_1$-$C_6$ alkyl, where any two adjacent $R^1$, $R^2$, $R^3$, $R^4$, and $R^5$ may join to form a 5-membered or 6-membered alkyl or aryl, and provided that at least one of $R^1$, $R^2$, $R^3$, $R^4$, and $R^5$ is not H.

E. The compound of any one of Paragraphs A-D, wherein $R^1$, $R^2$, $R^3$, $R^4$, and $R^5$ are each independently H, halo, amino, trifluoromethyl, nitro, pentafluorosulfanyl, or $C_1$-$C_4$ alkyl, where any two adjacent $R^1$, $R^2$, $R^3$, $R^4$, and $R^5$ may join to form a 5-membered or 6-membered alkyl or aryl, and provided that at least one of $R^1$, $R^2$, $R^3$, $R^4$, and $R^5$ is not H.

F. The compound of any one of Paragraphs A-E, wherein the compound is of Formula IB (IB)

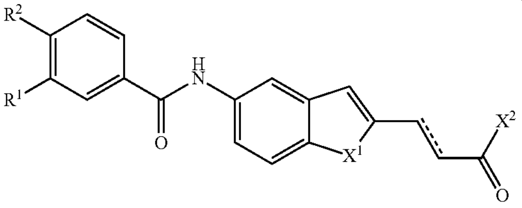

or a pharmaceutically acceptable salt thereof, wherein - - - - - - is a single bond or a double bond; and provided that at least one of $R^1$ and $R^2$ is not H.

G. The compound of any one of Paragraphs A-F, wherein $X^1$ is S.

H. The compound of any one of Paragraphs A-G, wherein $L^1$ is —CH=CH— in Formula I, $L^1$ is —CH=CH— in Formula IA, or - - - - - - a double bond in Formula IB.

I. The compound of any one of Paragraphs A-H, wherein $X^2$ is OH, $NH_2$, NH—OH, or NH—$NH_2$.

J. A composition comprising a compound of any one of Paragraphs A-I and a pharmaceutically acceptable carrier.

K. A pharmaceutical composition comprising an effective amount of a compound of any one of Paragraphs A-I for treating a hyperproliferative disease with HuR overexpression.

L. The pharmaceutical composition of Paragraph K, wherein the hyperproliferative disease with HuR overexpression is a colon cancer, a prostate cancer, a breast cancer, a brain cancer, an ovarian cancer, a pancreatic cancer, or a lung cancer.

M. The pharmaceutical composition of Paragraph K or Paragraph L, wherein the pharmaceutical composition further comprises a pharmaceutically acceptable carrier.

N. A method comprising administering a compound of any one of Paragraphs A-I to a subject suffering from a hyperproliferative disease with HuR overexpression or a pharmaceutical composition of any one of Paragraphs K-M to a subject suffering from a hyperproliferative disease with HuR overexpression.

O. The method of Paragraph N, wherein the method comprises administering an effective amount of the compound, wherein the effective amount is an amount effective to treat the hyperproliferative disease with HuR overexpression.

P. The method of Paragraph N or Paragraph O, wherein the method comprises administering a first amount of the compound and administering a second amount of one or more therapeutic agents, wherein the first amount and second amount combined are effective to treat the hyperproliferative disease with HuR overexpression.

Q. The method of Paragraph P, wherein the therapeutic agent is a chemotherapeutic compound, radiation, or both.

R. The method of Paragraph P or Paragraph Q, wherein the therapeutic agent comprises docetaxel, doxorubicin, or both.

S. The method of any one of Paragraphs K—R, wherein the hyperproliferative disease with HuR overexpression is a colon cancer, a prostate cancer, a breast cancer, a brain cancer, an ovarian cancer, a pancreatic cancer, or a lung cancer.

Other embodiments are set forth in the following claims, along with the full scope of equivalents to which such claims are entitled.

The invention claimed is:

1. A compound according to Formula I (I)

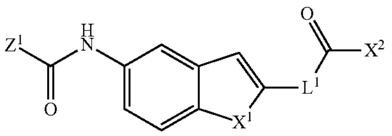

or a pharmaceutically acceptable salt thereof, wherein $Z^1$ is

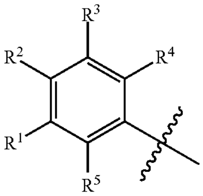

or

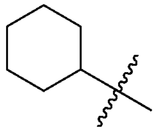

;

$R^1$, $R^2$, $R^3$, $R^4$, and $R^5$ are each independently H, halo, —$NR^{75}R^{76}$, cyano, trifluoromethyl, thiol, alkylthio, sulfoxide, sulfone, nitro, pentafluorosulfanyl, carboxylate, amide, ester, $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, or aryloyloxy group, where any two adjacent $R^1$, $R^2$, $R^3$, $R^4$, and $R^5$ may join to form a 5-membered alkyl, heteroalkyl, aryl, or heteroaryl;

$R^{75}$ and $R^{76}$ are each independently alkenyl, alkynyl, cycloalkyl, aryl, aralkyl, heterocyclylalkyl, heterocyclyl, or unsubstituted alkyl;

L' is —$CH_2$—, —$CH_2$—$CH_2$—, or —CH═CH—;

$X^1$ is O, NH, or S; and $X^2$ is OH, $NH_2$, NH—OH, NH—$NH_2$, or O—($C_1$-$C_6$ alkyl).

2. The compound of claim 1, where the compound is of Formula IA (IA)

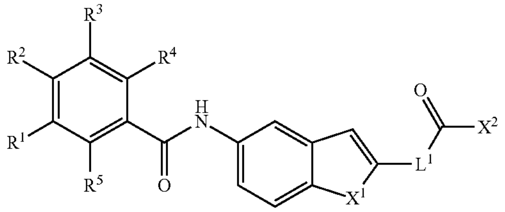

or a pharmaceutically acceptable salt thereof, provided that at least one of $R^1$, $R^2$, $R^3$, $R^4$, and $R^5$ is not H.

3. The compound of claim 2, wherein $R^1$, $R^2$, $R^3$, $R^4$, and $R^5$ are each independently H, halo, —$NR^{75}R^{76}$, cyano, trifluoromethyl, thiol, nitro, pentafluorosulfanyl, or $C_1$-$C_6$ alkyl, where any two adjacent $R^1$, $R^2$, $R^3$, $R^4$, and $R^5$ may join to form a 5-membered or 6-membered alkyl or aryl, and provided that at least one of $R^1$, $R^2$, $R^3$, $R^4$, and $R^5$ is not H.

4. The compound of claim 2, wherein $R^1$, $R^2$, $R^3$, $R^4$, and $R^5$ are each independently H, halo, —$NR^{75}R^{76}$, trifluoromethyl, nitro, pentafluorosulfanyl, or $C_1$-$C_4$ alkyl, where any two adjacent $R^1$, $R^2$, $R^3$, $R^4$, and $R^5$ may join to form a 5-membered or 6-membered alkyl or aryl, and provided that at least one of $R^1$, $R^2$, $R^3$, $R^4$, and $R^5$ is not H.

5. The compound of claim 2, wherein $X^1$ is S.

6. The compound of claim 2, wherein $L^1$ is —CH═CH—.

7. The compound of claim 2, wherein $X^2$ is OH, $NH_2$, NH—OH, or NH—$NH_2$.

8. The compound of claim 1, wherein $R^1$ is —$N(CH_3)_2$, trifluoromethyl, pentafluorosulfanyl, or tert-butyl; and $R^2$, $R^3$, $R^4$, and $R^5$ are each independently H.

9. The compound of claim 1, wherein the compound is of Formula IB (IB)

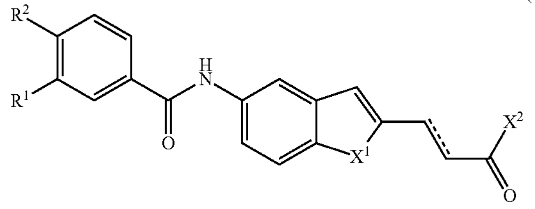

or a pharmaceutically acceptable salt thereof, wherein ═══ is a single bond or a double bond; and provided that at least one of $R^1$ and $R^2$ is not H.

10. The compound of claim 9, wherein $R^1$ is —$N(CH_3)_2$, trifluoromethyl, pentafluorosulfanyl, or tert-butyl;

$R^2$ is H; and $X^2$ is $NH_2$, NH—OH, or NH—$NH_2$.

11. The compound of claim 9, wherein $R^1$ and $R^2$ are each independently H, halo, —$NR^{75}R^{76}$, cyano, trifluoromethyl, thiol, nitro, pentafluorosulfanyl, or $C_1$-$C_6$ alkyl, provided that at least one of $R^1$ and $R^2$ is not H.

12. The compound of claim 9, wherein $R^1$ and $R^2$ are each independently H, halo, —$NR^{75}R^{76}$, trifluoromethyl, nitro, pentafluorosulfanyl, or $C_1$-$C_4$ alkyl, provided that at least one of $R^1$ and $R^2$ is not H.

13. The compound of claim 9, wherein $X^1$ is S.

14. The compound of claim 9, wherein ------ is a double bond.

15. The compound of claim 9, wherein $X^2$ is OH, $NH_2$, NH—OH, or NH—$NH_2$.

16. The compound of claim 1, wherein $R^2$ is —$N(CH_3)_2$, trifluoromethyl, pentafluorosulfanyl, or tert-butyl; and $R^1$, $R^3$, $R^4$, and $R^5$ are each independently H.

17. A compound according to Formula IA (IA)

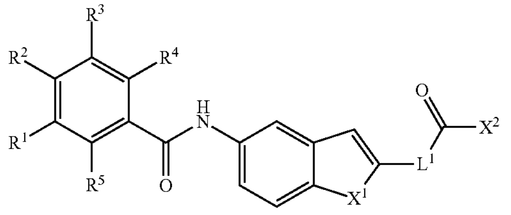

or a pharmaceutically acceptable salt thereof, wherein $R^2$ is tert-butyl;

$R^1$, $R^3$, $R^4$, and $R^5$ are each independently H;

$L^1$ is absent;

$X^1$ is O, NH, or S; and $X^2$ is $NH_2$, NH—OH, or NH—$NH_2$.

18. The compound of claim 17, wherein $X^1$ is O or NH.

19. A composition comprising a compound of claim 1 and a pharmaceutically acceptable carrier.

* * * * *